(12) United States Patent
Tuna et al.

(10) Patent No.: US 11,214,618 B2
(45) Date of Patent: Jan. 4, 2022

(54) LAG-3 BINDING MEMBERS

(71) Applicant: F-star Beta Limited, Cambridge (GB)

(72) Inventors: Mihriban Tuna, Cambridge (GB); Francisca Wollerton Van Horck, Cambridge (GB); Katy Louise Everett, Cambridge (GB); Miguel Gaspar, Cambridge (GB); Matthew Kraman, Cambridge (GB); Katarzyna Kmiecik, Cambridge (GB); Natalie Fosh, Cambridge (GB)

(73) Assignee: F-star Therapeutics Limited, Cambridge (GB)

( * ) Notice: Subject to any disclaimer, the term of this patent is extended or adjusted under 35 U.S.C. 154(b) by 421 days.

(21) Appl. No.: 16/311,596

(22) PCT Filed: Jun. 20, 2017

(86) PCT No.: PCT/EP2017/065052
§ 371 (c)(1),
(2) Date: Dec. 19, 2018

(87) PCT Pub. No.: WO2017/220555
PCT Pub. Date: Dec. 28, 2017

(65) Prior Publication Data
US 2019/0330344 A1    Oct. 31, 2019

Related U.S. Application Data

(60) Provisional application No. 62/352,470, filed on Jun. 20, 2016.

(51) Int. Cl.
*C07K 16/28* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *C07K 16/2866* (2013.01); *C07K 16/2896* (2013.01); *A61K 2039/505* (2013.01); *A61K 2039/5152* (2013.01); *C07K 2317/31* (2013.01); *C07K 2317/33* (2013.01); *C07K 2317/34* (2013.01); *C07K 2317/526* (2013.01); *C07K 2317/53* (2013.01); *C07K 2317/73* (2013.01); *C07K 2317/74* (2013.01); *C07K 2317/76* (2013.01); *C07K 2317/92* (2013.01); *C07K 2318/20* (2013.01)

(58) Field of Classification Search
None
See application file for complete search history.

(56) References Cited

U.S. PATENT DOCUMENTS

| 3,909,459 | A  | 9/1975  | Friese et al. |
| 3,967,230 | A  | 6/1976  | Kamigaito et al. |
| 4,004,183 | A  | 1/1977  | Oki et al. |
| 6,380,664 | B1 | 4/2002  | Pollner |
| 9,567,399 | B1 | 2/2017  | Campbell et al. |
| 9,617,338 | B1 | 4/2017  | Campbell et al. |
| 10,090,646 | B2 | 10/2018 | Takaoka et al. |
| 10,205,305 | B2 | 2/2019  | Uegaki et al. |
| 2003/0030355 | A1 | 2/2003 | Honda |
| 2009/0055944 | A1 | 2/2009 | Korman et al. |
| 2012/0276104 | A1 | 11/2012 | Woisetschlager |
| 2015/0214697 | A1 | 7/2015 | Yoshida et al. |
| 2015/0259420 | A1* | 9/2015 | Triebel .................. A61P 35/00 424/136.1 |
| 2016/0043531 | A1 | 2/2016 | Firstenberg et al. |
| 2018/0175592 | A1 | 6/2018 | Uegaki et al. |
| 2019/0202920 | A1 | 7/2019 | Tuna et al. |
| 2019/0256602 | A1 | 8/2019 | Campbell et al. |
| 2019/0338049 | A1 | 11/2019 | Tuna et al. |
| 2021/0139590 | A1 | 5/2021 | Tuna et al. |
| 2021/0238299 | A1 | 8/2021 | Pechouckova et al. |

FOREIGN PATENT DOCUMENTS

| EP | 2407487 A1 | 1/2012 |
| EP | 2546268 A1 | 1/2013 |
| EP | 2905030 A1 | 8/2015 |
| JP | S51-046628 A | 4/1976 |
| JP | 2003-022886 A | 1/2003 |
| JP | 2012-500006 A | 1/2012 |
| JP | 2017-010741 A | 1/2017 |
| WO | WO 2006/072620 A1 | 7/2006 |
| WO | WO 2009/000006 A1 | 12/2008 |

(Continued)

OTHER PUBLICATIONS

Goding et al., "Combination of adoptive cell transfer, anti-PD-L1 and anti-LAG-3 antibodies for the treatment of recurrent tumors: better with more." *OncoImmunology* vol. 2, No. 8, pp. e25050-1-e25050-3 (Oct. 22, 2013).

Kraman et al., "A LAG-3/PD-L1 bispecific antibody inhibits tumor growth in two syngeneic colon carcinoma models." Retrieved from http://www.f-star.com/media/73722/A-LAG-3-PD-L1-bispecific-antibody-inhibits-tumour-growth-in-two-syngeneic-colon-carcinoma-models.pdf, 1 page (document marked Nov. 9-13, 2016).

Lundqvist et al., "31st Annual Meeting and Associated Programs of the Society for Immunotherapy of Cancer (SITC 2016): Part One." *Journal for Immunotherapy of Cancer*, vol. 4, No. 1, p. 74, abstract P124. (Nov. 16, 2016).

Vilgelm et al., "Combinatorial approach to cancer immunotherapy: strength in numbers." *Journal of Leukocyte Biology* vol. 100, No. 2, pp. 275-290 (published online Jun. 2, 2016).

(Continued)

*Primary Examiner* — Nelson B Moseley, II
(74) *Attorney, Agent, or Firm* — Wolf, Greenfield & Sacks, P.C.

(57) ABSTRACT

The present invention relates to specific binding members which bind to lymphocyte-activation gene 3 (LAG-3). The specific binding members preferably comprise a LAG-3 antigen-binding site which may be located in two or more structural loops of a CH3 domain of the specific binding member. The specific binding members of the invention find application, for example, in cancer therapy.

20 Claims, 7 Drawing Sheets

Specification includes a Sequence Listing.

(56) References Cited

FOREIGN PATENT DOCUMENTS

| WO | WO 2009/132876 A1 | 11/2009 |
|---|---|---|
| WO | WO 2010/019570 A2 | 2/2010 |
| WO | WO 2014/008218 A1 | 1/2014 |
| WO | WO 2014/140180 A1 | 9/2014 |
| WO | WO 2015/048312 A1 | 4/2015 |
| WO | WO 2015/138920 A1 | 9/2015 |
| WO | WO 2015/198312 A1 | 12/2015 |
| WO | WO 2015/200119 A1 | 12/2015 |
| WO | WO 2016/028672 A1 | 2/2016 |
| WO | WO 2016/177802 A1 | 11/2016 |
| WO | WO 2016/185016 A1 | 11/2016 |
| WO | WO 2016/200782 A1 | 12/2016 |
| WO | WO 2017/009456 A1 | 1/2017 |
| WO | WO 2017/015560 A2 | 1/2017 |
| WO | WO 2017/025498 A1 | 2/2017 |
| WO | WO 2017/052241 A1 | 3/2017 |
| WO | WO 2017/062888 A1 | 4/2017 |
| WO | WO 2017/077085 A2 | 5/2017 |
| WO | WO 2017/087589 A2 | 5/2017 |
| WO | WO 2017/087901 A2 | 5/2017 |
| WO | WO 2017/123650 A2 | 7/2017 |
| WO | WO 2017/182672 A1 | 10/2017 |
| WO | WO 2017/220569 A1 | 12/2017 |
| WO | WO 2017/220990 A9 | 12/2017 |
| WO | WO 2018/017673 A1 | 1/2018 |
| WO | WO 2018/056821 A1 | 3/2018 |
| WO | WO 2019/025545 A1 | 2/2019 |

OTHER PUBLICATIONS

[No Author Listed] Abstract for CHI Immuno-Oncology Summit Europe. Mar. 18-22, 2019. 1 page. PDR303.

[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.

[No Author Listed] F-Star Modular Bispecific Antibodies. Summary for ATLAS deck. Presented at JP Morgan. Jan. 2017. 1 page. PDR159.

[No Author Listed] First-in-Class bispecific antibodies for cancer immunotherapy. Presentation at Takeda. Dec. 13, 2016. 24 pages. PDR160.

[No Author Listed], Pipeline Overview: F-star is developing a pipeline of bispecific antibodies focused on oncology and immuno-oncology. F-Start website update. Sep. 2016. 2 pages. PDR126.

Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.

Asgarov et al., A new anti-mesothelin antibody targets selectively the membrane-associated form. MAbs. Apr. 2017;9(3):567-577. doi: 10.1080/19420862.2017.1288770.

Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.

Berg et al., Biochemistry. 5th ed. New York. 2002. Accessible at https://www.ncbi.nlm.nih.gov/books/NBK22358/section5.5. Accessed Jun. 9, 2021. 4 pages.

Bernett et al., Abstract P122: Multiple bispecific checkpoint combinations enhance T cell activity. J Immunother Cancer. 2016;4(Suppl 1):P122. 2 pages.

Bernett et al., Multiple bispecific checkpoint combinations enhance T cell activity. Xencor Poster Presentation. 2016. 1 page.

Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.

Borlak et al., Immune-mediated liver injury of the cancer therapeutic antibody catumaxomab targeting EpCAM, CD3 and Fc? receptors. Oncotarget. May 10, 2016;7(19):28059-74. doi: 10.18632/oncotarget.8574.

Brewis, Development of an anti-PD-L1 Fcab. Presentation. Human Antibodies and Hybrodomas Conference. Oct. 22, 2018. PDR 312.

Brewis, Identification of a PD-L1 binding Fcab: a potent inhibitor of immunosuppressive signals. Abstract. Huamn Antibodies and Hybridomas 2018. Jun. 11, 2018. 1 page. PDR282.

Brewis, The use of bispecific antibodies to modulate anti-tumour immune responses. Oral Presentation at ELRIG-Research and Innovation. Mar. 29, 2017. 33 pages. PDR177.

Brewis, The use of bispecific antibodies to modulate anti-tumour immune responses. Oral Presentation at PEPtalk. Jan. 12, 2017. 26 pages. PDR163.

Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.

Burova et al., Abstract P195: A novel anti-human LAG-3 antibody in combination with anti-human PD-1 (REGN2810) shows enhanced anti-tumor activity in PD-1 × LAG-3 dual-humanized mice and favorable pharmacokinetic and safety profiles in cynomolgus monkey. J Immunother Cancer. 2016;4(Suppl 1):P195. 2 pages.

Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.

Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.

Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

Chiu et al., Antibody Structure and Function: The Basis for Engineering Therapeutics. Antibodies (Basel). Dec. 3, 2019;8(4):55. doi: 10.3390/antib8040055.

Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.

Davies, Analytical challenges for next generation biologies. Oral Presentation at Waters Biopharma Mini-Seminar. May 24, 2017. 20 pages. PDR191.

Davies, Bispecific Antibodies: New Opportunities for Novel Therapies. Oral Presentation at Bioprocess UK 2016. Nov. 26, 2016. 14 pages. PDR 135.

Davies, Overcoming the Manufacturing Challenges for Bisepcific mAbs. Oral Presentation at 5th Annual Cell Culture and Bioprocessing Congress. Nov. 6, 2016. 16 pages. PDR142.

Davies, Overcoming the Manufacturing Challenges for Bisepcific mAbs. Oral Presentation at Biopronet 3rd Annual Scientific Symposium. Oct. 20, 2016. 16 pages. PDR136.

Daxini et al., Vasculitis associated with immune checkpoint inhibitors—a systematic review. Clin Rheumatol. Sep. 2018;37(9):2579-2584. doi: 10.1007/s10067-018-4177-0. Epub Jun. 19, 2018.

Demeure et al., T Lymphocytes infiltrating various tumour types express the MHC class II ligand lymphocyte activation gene-3

(56) References Cited

OTHER PUBLICATIONS (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: A LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.
Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.
Doody, In vivo Efficacy of bispecific antibodies targeting two immmune-modulatory receptors. Oral Presentation at PEGS Europe. Nov. 4, 2016. 16 pages. PDR144.
Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.
Everett et al., Abstract PR06: A LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.
Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.
F-STAR, First-in-Class Bispecific Antibodies for Cance Immunotherapy. Jul. 2016. Presentation. 14 pages. PDR119.
Fiehler, Development of an anti-PD-L1 Fcab. Presentation. European Antibody Congress. Oct. 29, 2018. 26 pages. PDR312.
Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.
Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.
Gliddon, Pushing all the buttons: innovating in immuno-oncology with mAb. Oral Presentation at Phacilitate Immunotherapy World 2017. Jan. 18, 2017. 11 pages. PDR165.
Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.
Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.
Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.
Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.
Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.
Hid Cadena et al., Checks and Balances in Autoimmune Vasculitis. Front Immunol. Feb. 22, 2018;9:315. doi: 10.3389/fimmu.2018.00315.
Horn et al., CD3×PDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.
Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilites. Oct. 17-20, 2015. Orlando, FL. doi: 10.1158/1557-3265.OVCA15-PR03. Published Jan. 2016. 8 pages.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.
Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.
Jochems et al., Analyses of functions of an anti-PD-L1/TGF?R2 bispecific fusion protein (M7824). Oncotarget. Sep. 8, 2017;8(43):75217-75231. doi: 10.18632/oncotarget.20680.
Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.
Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.
Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.
Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.
Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).
Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.
Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.
Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.
Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.
Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.
Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.
Kraman et al., A LAG-3/PD-L1 bispecific antibody inhibits tumour growth in two syngeneic coon carcinoma models. Poster 3005.

(56) References Cited

OTHER PUBLICATIONS

Poster Presentation. Keystome Symposium—Biobetters and Next-Generation Biologies. Jan. 22-26, 2017. 1 page. PDR164.

Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.

La Motte-Mohs et al., Abstract 3217: MGD013, a bispecific PD-1 × LAG-3 Dual-Affinity Re-Targeting (DART®) protein with T-cell immunomodulatory activity for cancer treatmentR. AACR 107th Annual Meeting. Apr. 16-20, 2016. New Orleans, LA. Doi: 10.1158/1538-7445.AM2016-3217. 8 pages.

La Motte-Mohs et al., MGD013, a bispecific PD-1 × LAG-3 Dual-Affinity Re-Targeting (DART®) protein with T-cell immunomodulatory activity for cancer treatment. Poster Presentation. 2016. http://ir.macrogenics.com/events.cfm. 1 page.

Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.

Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.

Lee et al., 4-1BB and OX40 dual costimulation synergistically stimulate primary specific CD8 T cells for robust effector function. J Immunol. Sep. 1, 2004;173(5):3002-12. doi: 10.4049/jimmunol. 173.5.3002.

Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.

Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.

Lobner et al., Engineered IgG1-Fc—one fragment to bind them all. Immunol Rev. Mar. 2016;270(1):113-31. doi: 10.1111/imr.12385.

Lobner et al., Two-faced Fcab prevents polymerization with VEGF and reveals thermodynamics and the 2.15 Åcrystal structure of the complex. MAbs. Oct. 2017;9(7):1088-1104. doi: 10.1080/19420862. 2017.1364825. Epub Aug. 17, 2017.

McCourt et al., KY1055; a novel ICOS/PD-L1 bispecific antibody, enhance T cell activation and delivers potent monotherapy anti-tumour response in vivo. Abstract. CIMT 2018. Feb. 28, 2018. 1 page. PDR245.

McCourt et al., KY1055; a novel ICOS/PD-L1 bispecific antibody, enhance T cell activation and delivers potent monotherapy anti-tumour response in vivo. Poster Presentation. CIMT Conference. May 9, 2018. 1 page. PDR 264.

McCourt et al., KY1055; a novel ICOS/PD-L1 bispecific antibody, enhance T cell activation and delivers potent monotherapy anti-tumour response in vivo. Presentation. CIMT Conference. May 9, 2018. 13 pages. PDR265.

Michaelson et al., Anti-tumor activity of stability-engineered IgG-like bispecific antibodies targeting TRAIL-R2 and LTbetaR. MAbs. Mar.-Apr. 2009;1(2):128-41. doi: 10.4161/mabs.1.2.7631. Epub Mar. 11, 2009.

Munoz-Olaya, Development of an anti-PD-L1Fcab. Presentation. PEGS Lisbon. Nov. 16, 2018. 24 pages. PDR321.

Nalivaiko et al., A Recombinant Bispecific CD20×CD95 Antibody With Superior Activity Against Normal and Malignant B-cells. Mol Ther. Feb. 2016;24(2):298-305. doi: 10.1038/mt.2015.209. Epub Nov. 19, 2015.

Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.

Powles et al., MPDL3280A (anti-PD-L1) treatment leads to clinical activity in metastatic bladder cancer. Nature. Nov. 27, 2014;515(7528):558-62. doi: 10.1038/nature13904.

Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol. 1101244. Epub Aug. 31, 2011.

Ramelet et al., Beneficial outcome of combination therapy with 4-1BB targeting antibody. Eur J Cancer. Nov. 29, 2016;69(Suppl 1):S96-S97.

Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.

Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.

Sallin et al., The anti-lymphoma activities of anti-CD137 monoclonal antibodies are enhanced in Fc?RIII(−/−) mice. Cancer Immunol Immunother. Sep. 2014;63(9):947-58. doi: 10.1007/s00262-014-1567-2. Epub Jun. 14, 2014.

Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.

Shindo et al., Combination immunotherapy with 4-IBB activation and PD-1 blockade enhances antitumor efficacy in a mouse model of subcutaneous tumor. Anticancer Res. Jan. 2015;35(1):129-36.

Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.

Tuna, Identification of a PD-L1 binding FCAB: a potent inhibitor of immunosuppressive signals. Abstract. European Antibody Congress. May 3, 2018. 1 page. PDR270.

Tuna, The use of bispecific antibodies to modulate anti-tumour immune responses. Oral Presentation at 10th Annual Proteins and Antibodies Congress. Apr. 24, 2017. 26 pages. PDR183.

Vanamee et al., Structural principles of tumor necrosis factor superfamily signaling. Sci Signal. Jan. 2, 2018;11(511):eaao4910. doi: 10.1126/scisignal.aao4910. 12 pages.

Weismann, A LAG-3/PD-L1 Bispecific Antibody Inhibits Tumour Growth In Two Syngeneic Colon Carcinoma Models. International Conference on Human and Translational Immunology. Rhodes, Greece. Sep. 16-21, 2016. Presentation. 6 pages. PDR128.

Wherry, T cell exhaustion. Nat Immunol. Jun. 2011;12(6):492-9. doi: 10.1038/ni.2035.

Wilton, KY1055, a bispecific mAb2 targeting ICOS and PD-L1. Presentation. Feb. 21, 2018. 17 pages. PDR238.

Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.

Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.

Workman et al., Negative regulation of T cell homeostasis by lymphocyte activation gene-3 (CD223). J Immunol. Jan. 15, 2005;174(2):688-95. doi: 10.4049/jimmunol.174.2.688.

Workman et al., The CD4-related molecule, LAG-3 (CD223), regulates the expansion of activated T cells. Eur J Immunol. Apr. 2003;33(4):970-9. doi: 10.1002/eji.200323382.

Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.

Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.

(56) References Cited

OTHER PUBLICATIONS

Wydro, Bispecific antibodies: new opportunities for novel therapies. Oral Presentation at 7th Annual Biologies Symposium. Mar. 1, 2017. 24 pages. PDR172.

Wykes et al., Immune checkpoint blockade in infectious diseases. Nat Rev Immunol. Feb. 2018;18(2):91-104. doi: 10.1038/nri.2017.112. Epub Oct. 9, 2017.

Xu et al., In vitro characterization of five humanized OKT3 effector function variant antibodies. Cell Immunol. Feb. 25, 2000;200(1):16-26.

Zhang et al., Structural basis of a novel PD-L1 nanobody for immune checkpoint blockade. Cell Discov. Mar. 7, 2017;3:17004. doi: 10.1038/celldisc.2017.4.

* cited by examiner

Figure 1

A. CH3 (AB and CD regions)

| | | 1.4 | 1.3 | 1.2 | 1.1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 35 | 36 | 37 | 38 | 39 | 40 | 41 | 42 | 43 | 44 | 45 | 45.1 | 45.2 | 45.3 | 45.4 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | AB | | | | | | | | | | | | | | | | | | | | | | | | | | | CD | | | | | | | | |
| FS18-7-9 | | G | Q | Q | R | E | P | Q | V | Y | T | L | P | P | S | W | D | E | P | W | G | E | D | V | S | L | T | C | L | V | K | G | F | Y | P | S | D | I | A | V | E | W | E | S | N | G | Q | P | E | N | N | Y | K | T |
| FS18-7-32 | | | | | | | | | | | | | | | | | | | | | | | | | | | | | | | | | | | | | E | | | | | | | | | | | | | | | | | |
| FS18-7-33 | | | | | | | | | | | | | | | | | | | | | | | | | | | | | | | | | | | | | | | | | | | | | | | | | | D | | | | |
| FS18-7-36 | | | | | | | | | | | | | | | | | | | | | | | | | | | | | | | | | | | | | | | | | | | | | | | Y | | | I | E | | | |
| FS18-7-58 | | | | | | | | | | | | | | | | | | | | | | | | | | | | | | | | | | | | | | | | | | | | | | | I | | | W | F | | | |
| FS18-7-62 | | | | | | | | | | | | | | | | | | | | | | | | | | | | | | | | | | | | | | | | | | | | | | | Y | A | | Y | | | | |
| FS18-7-65 | | | | | | | | | | | | | | | | | | | | | | | | | | | | | | | | | | | | | | | | | | | | | | | K | K | | E | | | | |
| FS18-7-78 | | | | | | | | | | | | | | | | | | | | | | | | | | | | | | | | | | | | | | | | | | | | | | | V | | | L | | V | | |
| FS18-7-88 | | | | | | | | | | | | | | | | | | | | | | | | | | | | | | | | | | | | | | | | | | | | | | | Y | | | D | | | | |
| FS18-7-95 | | | | | | | | | | | | | | | | | | | | | | | | | | | | | | | | | | | | | | | | | | | | | | | | Q | | | | | | |

B. CH3 (EF region)

| | | 81 | 82 | 83 | 84 | 84.1 | 84.2 | 84.3 | 84.4 | 85.4 | 85.3 | 85.2 | 85.1 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 112 | 113 | 114 | 115 | 116 | 117 | 118 | 119 | 120 | 121 | 122 | 123 | 124 | 125 | 129 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | | | | | | | | | | | | |
| FS18-7-9 | | T | P | P | V | L | D | S | D | G | S | F | F | L | Y | S | K | L | T | V | P | Y | D | R | W | V | W | P | D | E | F | S | C | S | V | M | H | E | A | L | H | N | H | Y | T | Q | K | S | L | S | L | S | P | G |
| FS18-7-32 | | | | | | | | | | | | | | | | | | | | | | | | | | | | | | | | | | | | | | | | | | | | | | | | | | | | | | |
| FS18-7-33 | | | | | | | | | | | | | | | | | | | | | | | | | | | | | | | | | | | | | | | | | | | | | | | | | | | | | | |
| FS18-7-36 | | | | | | | | | | | | | | | | | | | | | | | | | | | | | | | | | | | | | | | | | | | | | | | | | | | | | | |
| FS18-7-58 | | | | | | | | | | | | | | | | | | | | | | | | | | | | | | | | | | | | | | | | | | | | | | | | | | | | | | |
| FS18-7-62 | | | | | | | | | | | | Y | | | | | | | | | | | | | | | | | | | | | | | | | | | | | | | | | | | | | | | | | |
| FS18-7-65 | | | | | | | | | | | | | | | | | | | | | | | | | | | | | | | | | | | | | | | | | | | | | | | | | | | | | | |
| FS18-7-78 | | | | | | | | | | | | | | | | | | | | | | | | | | | | | | | | | | | | | | | | | | | | | | | | | | | | | | |
| FS18-7-88 | | | | | | | | | | | | | | | | | | | | | | | | | | | | | | | | | | | | | | | | | | | | | | | | | | | | | | |
| FS18-7-95 | | | | | | | | | | | | | | | | | | | | | | | | | | | | | | | | | | | | | | | | | | | | | | | | | | | | | | |

Figure 1

| Fcab | Identity to FS18-7-9 |
|---|---|
| FS18-7-32 | 99.1% |
| FS18-7-33 | 99.1% |
| FS18-7-36 | 99.1% |
| FS18-7-58 | 96.2% |
| FS18-7-62 | 98.1% |
| FS18-7-65 | 97.2% |
| FS18-7-78 | 97.2% |
| FS18-7-88 | 97.2% |
| FS18-7-95 | 97.2% |

LAG-3 BINDING MEMBERS

CROSS REFERENCE TO RELATED APPLICATIONS

This is the U.S. National Stage of International Application No. PCT/EP2017/065052, filed Jun. 20, 2017, which was published in English under PCT Article 21(2), which in turn claims the benefit of U.S. Provisional Application No. 62/352,470 filed on 20 Jun. 2016, which is hereby incorporated by reference in its entirety.

RELATED APPLICATIONS

The present case is related to U.S. 62/352,470 filed on 20 Jun. 2016, the contents of which are hereby incorporated by reference in their entirety.

FIELD OF THE INVENTION

The present invention relates to specific binding members which bind to lymphocyte-activation gene 3 (LAG-3). The specific binding members preferably comprise a LAG-3 antigen-binding site which may be located in two or more structural loops of a CH3 domain of the specific binding member. The specific binding members of the invention find application, for example, in cancer therapy.

BACKGROUND TO THE INVENTION

Lymphocyte Activation Gene-3 (LAG-3; CD223) is a member of the Ig superfamily, and is genetically and structurally related to CD4 (though with only 20% sequence identity). Like CD4, LAG-3 binds to MHC crass II molecules but with higher affinity than CD4 ($K_D$=60 nM). LAG-3 is expressed on activated T cells, NK cells, pDCs, B cells, γδ T cells and participates in immune suppression, particularly through persistent strong expression in a percentage of regulatory T cells (Tregs) (Liang et al, 2008).

The LAG-3 gene is located on human chromosome 12, adjacent to the CD4 gene, and spans 8 exons. There are five alternative transcripts, two of which generate protein products: a full length transmembrane protein and an alternatively spliced soluble monomeric form. The full-length transcript encodes a 525 amino acid protein with a molecular weight of 70 kDa and has functional activity, while the soluble form appears not to bind MHC class II molecules and its function is unknown. Human full-length LAG-3 protein has 93% sequence identity to *Macaca fascicularis* (cynomolgus monkey) LAG-3 and 70% sequence identity to *Mus musculus* (house mouse) LAG-3.

LAG-3 is a transmembrane protein with four extracellular Ig-like domains (D1-D4), and a cytoplasmic portion responsible for LAG-3 signalling. The cytoplasmic domain has an EP (giutamic acid/proline) motif that associates with LAG-3-associated protein (LAP) as well as a KIEELE motif thought to be required for LAG-3 modulation of T cell function. Reports on the role of the EP motif suggest that it may be responsible for trafficking of LAG-3 to the T cell surface membrane (Bae et al, 2014), or may be directly responsible for modulating downstream signalling of STAT5 during T cell activation (Durham et. al, 2014), or possibly both.

The immuno-suppressive mechanism of LAG-3 on T cells is thought to be driven by cross-linking of LAG-3 on activated T cells resulting in decreased calcium flux and IL-2 release during T cell activation (Huard et al, 1997). On Antigen Presenting Cells (APCs), binding to MHC II molecules by LAG-3 positive regulatory T cells causes decreased IL-12 secretion and down regulation of CD86 (Liang et al, 2008), a "secondary signal" of activation, resulting in T cell anergy from improper activation and/or reduced antigen presentation by the APCs. LAG-3 knock out mouse models are viable, with only mild lympho-hyperproliferation (Workman et al, 2003), indicating that LAG-3 acts as a modest immune "brake".

This suppressive interaction between LAG-3 and MHC class II has also been proposed to occur between Tregs and CD4 positive T cells (Sega et al, 2014). Tregs supress the immune response either by release of suppressive cytokines (such as IL-10 and TGFβ), manipulation of inflammatory metabolism (such as CD73 catabolised adenosine), regulating APC maturation, or direct interaction between regulatory T cells and effector T cells. There is evidence in humans that MHC class II positive Tregs are more suppressive than MHC class II negative Tregs (Baecher-Allen et al, 2006) and actively suppress the immune response through direct interaction with LAG-3 expressed on effector T cells. While LAG-3 negative Tregs can suppress conventional T cell proliferation, LAG-3 negative CD4 and CD8 T cells are resistant to Treg immune suppression. This process was described to occur between human T cells through a process known as trogacytosis (Sega et al, 2014) whereby Tregs not only prevent APC maturation but also acquire MHC class II to suppress primed LAG-3 positive CD4 T cells.

LAG-3 expression is also a marker of repeated antigen stimulation. In cancer, T cells commonly adopt an "exhausted" phenotype, involving expression of immuno-suppressors such as PD-1, CTLA-4, TIM-3, and LAG-3 (Wherry et al, 2011), where the cells have a general inability to properly proliferate and secrete chemokines in response to antigen. Inhibition of these immune-suppressors lowers the immune threshold and (re-)enables a proper anti-cancer response by the T cells. In preclinical models, this has been borne out using antagonist antibodies against LAG-3, CTLA-4 and PD-1 where a decrease in tumour burden was seen. LAG-3 inhibition by antagonistic antibodies is thought to reactivate the immune response in the tumour microenvironment, where expression of LAG-3 on CD4 positive T cells and CD8 positive T cells is associated with an exhausted phenotype, and LAG-3 expression on Tregs is associated with potent immuno-suppressive capabilities. Antibodies blocking LAG-3 increase T effector cell proliferation, cytokine production, cytotoxicity, and decrease Treg suppressor activity leading to a decrease in tumour growth.

In human tumours, increased expression of LAG-3 was found on tumour-infiltrating lymphocytes (TILs) from human renal cell carcinomas and other tumours, such as melanomas and lymphomas (Demeure et al, 2001; Wolchock et al, 2013). Importantly, LAG-3 is also closely correlated with T cell dysfunction in patients with chronic viral infection (Workman et al, 2005) and cancer (Workman et al, 2003), LAG-3 has also been identified as a surface marker for tumour-infiltrating Tregs in a variety of human cancers (Camisachi et al. 2010; Gandhi et al, 2006).

Monoclonal antibodies to human LAG-3 are in clinical development to abrogate immune suppression and potentially enhance antigen presentation in cancers (solid and haematological malignancies).

LAG-525 and IMP-701 (Novartis AG), are human antibodies against LAG-3 and have advanced to Phase II and I clinical studies, respectively, in kidney cancer (Renal Cell Cancer); Non-Small Cell Lung Cancer (NSCLC); Nasopharyngeal Cancer; Colorectal Cancer; Melanoma; Gastric Cancer and Adenocarcinoma of the Gastroesophageal Junction.

Anti-LAG-3 antibody BMS-986016 (Bristol-Myers Squibb Company), is currently in Phase I clinical testing for Ovarian Cancer; NSCLC; Colorectal Cancer; Cervical Cancer; Melanoma; Gastric Cancer; Bladder Cancer; Head And Neck Cancer Squamous Cell Carcinoma; Renal Cell Carcinoma and in Phase II studies in NSCLC; Relapsed Chronic Lymphocytic Leukemia (CLL); Refractory Chronic Lymphocytic Leukemia (CLL); Melanoma; Non-Hodgkin Lymphoma; Hodgkin Lymphoma; Diffuse Large B-Cell Lymphoma; Indolent Lymphoma; Mantle Cell Lymphoma; Refractory Multiple Myeloma; and Relapsed Multiple Myeloma as either monotherapy or as part of combination therapies.

Further antibodies against LAG-3 are also in preclinical development.

However, few anti-LAG-3 therapies are currently in clinical testing and none have been approved for therapy so there remains a need to develop additional molecules which target LAG-3, which can be used in the context of cancer therapy.

Statements of Invention

Following an extensive screening and affinity maturation programme, the present inventors were able to identify ten specific binding members comprising a binding site specific for LAG-3 in the CH3 domain of the molecule. These molecules were shown to have a high affinity for both human and cynomolgus LAG-3. The high affinity for human LAG-3 is expected to be advantageous in the treatment of e.g. cancers containing tumour-infiltrating lymphocytes (TILS; expressing LAG-3 in human patients, while the high affinity for cynomolgus LAG-3, which is comparable to the affinity for human LAG-3, is expected to be useful in the evaluation of the properties of the specific binding members in cynomolgus monkey disease models. The reason for this is that the results obtained are more likely to be predictive of the effects of the specific binding member in human patients than when a molecule which has a higher variability in its affinity for human and cynomolgus LAG-3 is tested in cynomolgus monkey models.

The specific binding members were also shown to have high activity in a T cell activation assay, which is expected to be predictive of improved efficacy in human patients through enhanced inhibition of LAG-3.

Surrogate murine versions of the specific binding members which bind to murine LAG-3 were also prepared by the inventors and shown to be capable of significantly inhibiting tumour growth in a syngeneic mouse model of cancer when the specific binding member further comprised a CDR-based antigen-binding site for a second tumour antigen. Based on the similar mechanism of action of mouse and human LAG-3 in the tumour environment, murine studies that show efficacy in diminishing tumour burden are expected to translate into clinical therapeutic benefits in human cancer patients. Based on these data, it is therefore expected that the specific binding members will find application in methods of treating cancers expressing LAG-3 in human patients.

Thus, in a first aspect the present invention provides a specific binding member which binds to lymphocyte-activation gene 3, and comprising a LAG-3 antigen-binding site located in a CH3 domain of the specific binding member.

The LAG-3 binding site preferably comprises the amino acid sequences WDEPWGED (SEQ ID NO: 1) and PYDRWVWPDE (SEQ ID NO: 3). The amino acid sequence WDEPWGED is preferably located in a first structural loop of the CH3 domain of the specific binding member and the amino acid sequence PYDRWVWPDE is preferably located in a second structural loop of the CH3 domain.

For example, the LAG-3 antigen-binding site may be located in a structural loop region of a CH3 domain of the specific binding member, wherein the structural loop region preferably comprises two or more structural loops, and wherein the LAG-3 binding site preferably comprises the amino acid sequences WDEPWGED (SEQ ID NO: 1) and PYDRWVWPDE (SEQ ID NO: 3).

As a further example, the LAG-antigen-binding site may be engineered into two or more structural loops of a CH3 domain of the specific binding member, wherein the LAG-3 binding site preferably comprises the amino acid sequences WDEPWGED (SEQ ID NO: 1) and PYDRWVWPDE (SEQ ID NO: 3).

As mentioned above, the sequences of the LAG-3 binding site are preferably located in two or more structural loops of the CH3 domain of the specific binding member. In a preferred embodiment the LAG-3 antigen-binding site comprises the amino acid sequence set forth in SEQ ID NO: 1 in the AB loop, and the amino acid sequence set forth in SEQ ID NO: 3 in the EF loop of the CH3 domain.

The amino acid sequence set forth in SEQ ID NO: 1 is preferably located at residues 11 to 18 of the CH3 domain; and/or the amino acid sequence set forth in SEQ ID NO: 3 is located at residues 92 to 101 of the CH3 domain; wherein the amino acid residue numbering is according to the ImMunoGeneTics IMGT) numbering scheme.

The LAG-3 antigen-binding site of the specific binding member may further comprise one of the following sequences, preferably in the CD loop of the CH3 domain of the specific binding member:

```
                            (SEQ ID NOS 2, 8 and 18)
    (i)   SNGQPENNY;

(SEQ ID NO: 13)
    (ii)  SNGQPEDNY;

(SEQ ID NO: 23)
    (iii) SNGYPEIEF;

(SEQ ID NO: 28)
    (iv)  SNGIPEWNY;

(SEQ ID NO: 33)
    (v)   SNGYAEYNY;

(SEQ ID NO: 38)
    (vi)  SNGYKEENY;

(SEQ ID NO: 43)
    (vii) SNGVPELNV;
    or (SEQ ID NO: 48)
    (viii) SNGYQEDNY.
```

Preferably, the LAG-3 antigen-binding site of the specific binding member further comprises one of the following sequences, preferably in the CD loop of the CH3 domain of the specific binding member: the amino acid sequence set forth in SEQ ID NO: 2, 28, or 38 in the CD loop of the CH3 domain. More preferably, the LAG-3 antigen-binding site of the specific binding member further comprises the amino acid sequence set forth in SEQ ID NO: 2 in the CD loop of the CH3 domain.

The amino acid sequence set forth in SEQ ID NO: 2, 8, 13, 18, 23, 28, 33, 38, 43, or 48 is preferably located at residues 43 to 78 of the CH3 domain of the specific binding member, wherein the residues are numbered according to the IMGT numbering scheme.

The sequence of the CH3 domain of the specific binding member, other the sequences of the LAG-3 antigen-binding site, is not particularly limited. Preferably, CH3 domain is a human immunoglobulin G domain, such as a human IgG1, IgG2, IgG3, or IgG4 CH3 domain, most preferably a human IgG1 CH3 domain. The sequences of human IgG1, IgG2, IgG3, or IgG4 CH3 domains are known in the art.

In a preferred embodiment, the specific binding member comprises the CH3 domain set forth in SEQ ID NO: 5, 10, 15, 20, 25, 30, 35, 40, 45, or 50, more preferably the CH3 domain set forth in SEQ ID NO: 5, 30, or 40, most preferably the CH3 domain set forth in SEQ ID NO: 5. Alternatively, the specific binding member may comprise a CH3 domain with an amino acid sequence which has at least 70%, at least 75%, at least 80%, at least 85%, at least 90%, at least 95%, at least 96%, at least 97%, at least 98%, or at least 99% sequence identity to SEQ ID NO: 5, 10, 15, 20, 25, 30, 35, 40, 45, or 50, preferably SEQ ID NO: 5, 30, or 40, more preferably SEQ ID NO: 5.

The specific binding member may further comprise a CH2 domain. The CH2 domain is preferably located at the N-terminus of the CH3 domain, as in the case in a human IgG molecule. The CH2 domain of the specific binding member is preferably the CH2 domain of human IgG1, IgG2, IgG3, or IgG4, more preferably the CH2 domain of human IgG1. The sequences of human IgG domains are known in the art. In a preferred embodiment, the specific binding member comprises an IgG CH2 domain with the sequence set forth in SEQ ID NO: 53, or a CH2 domain with an amino acid sequence which has at least 70%, at least 75%, at least 80%, at least 85%, at least 90%, at least 95%, at least 96%, at least 97%, at least 98%, or at least 99% sequence identity to SEQ ID NO: 53.

In a preferred embodiment, the specific binding member comprises the sequence set forth in SEQ ID NO: 6, 7, 11, 12, 16, 17, 21, 22, 26, 27, 31, 32, 36, 37, 41, 42, 46, 47, 51, or 52, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 6, 7, 11, 12, 16, 17, 21, 22, 26, 27, 31, 32, 36, 37, 41, 42, 46, 47, 51, or 52. More preferably, the specific binding member comprises the sequence set forth in SEQ ID NO: 6, 7, 31, 32, 41, or 42, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 6, 7, 31, 32, 41, or 42. Yet more preferably, the specific binding member comprises the sequence set forth in SEQ ID NO: 6 or 7, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 6 or 7.

Preferably, the specific binding member comprises an immunoglobulin hinge region, or part thereof, at the N-terminus of the CH2 domain. The immunoglobulin hinge region allows the two CH2-CH3 domain sequences to associate and form a dimer. Preferably, the hinge region, or part thereof, is a human IgG1, IgG2, IgG3 or IgG4 hinge region, or part thereof. More preferably, the hinge region, or part thereof, is an IgG1 hinge region, or part thereof. The sequence of the human IgG1 hinge region is shown in SEQ ID NO: 57. A suitable truncated hinge region which may form part of specific binding member is shown in SEQ ID NO: 58. This hinge region was present in the Fcab molecules tested in the Examples, whereas a full length hinge region was present in mock mAb$^2$ format. Thus, the specific binding member preferably comprises an immunoglobulin hinge region, or part thereof, at the N-terminus of the CH2 domain, wherein the hinge region has the sequence set forth in SEQ ID NO: 57 or SEQ ID NO: 58, or wherein the hinge region has an amino acid sequence which has at least 70%, at least 75%, at least 80%, at least 85%, at least 90%, at least 95%, at least 96%, at least 97%, at least 98%, or at least 99% sequence identity to the sequence set forth in SEQ ID NO: 57 or 58. Alternatively, the specific binding member may comprises an immunoglobulin hinge region, or part thereof, at the N-terminus of the CH2 domain, wherein the hinge region comprises the sequence set forth in SEQ ID NO: 57, or a fragment thereof, wherein said fragment comprises at least five, at least six, at least seven, at least eight, at least nine or more, at least ten, at least eleven, at least twelve, at least thirteen, or at least fourteen of the amino acid residues of SEQ ID NO: 57.

In addition to the LAG-3 antigen binding site in the CH3 domain of the specific binding member, the specific binding member may further comprise one or more additional antigen-binding sites to create a bi- or multi-specific molecule. Preferably, the specific binding member comprises a CDR-based antigen-binding site. CDR-based antigen binding sites are found in naturally-occurring immunoglobulin molecules and their structure is well-known in the art. Where the specific binding member comprises a CDR-based antigen binding site, the specific binding member is preferably an antibody molecule. The antibody molecule is not particularly limited, provided that it comprises a CH3 domain as herein defined and a CDR-based antigen binding site. In a preferred embodiment, the antibody molecule is a human immunoglobulin G molecule, such as a human IgG1, IgG2, IgG3 or IgG4 molecule, more preferably a human IgG1 molecule. The sequences of human immunoglobulin G molecules are known in the art and introducing a CH3 domain or CH3 domain sequence as disclosed here into such a molecule would not present any difficulty to the skilled person.

Where the specific binding member comprises one or more CDR-based antigen binding sites, the CDR-based antigen binding site preferably binds to a molecule which is an immune system modulator. Examples of immune system modulators include immunomodulatory receptors and ligands of immunomodulatory receptors. Preferably, the CDR-based antigen binding site binds to an immune system inhibitor or activator, most preferably an immune system inhibitor. Examples of preferred immune system inhibitors are: cytotoxic T-lymphocyte-associated protein 4 (CTLA-4), T cell immunoglobulin and mucin-domain containing-3 (TIM-3), CD73, and Colony stimulating factor 1 receptor (CSF-1R). In certain embodiments, the CDR-based antigen-binding site is not a binding site for PD-L1.

The specific binding member may further be conjugated to an immune system modulator, cytotoxic molecule, radioisotope, or detectable label. The immune system modulator may be cytotoxic molecule is a cytokine.

The present invention also provides a nucleic acid encoding a specific binding member or antibody molecule of the invention, as well as a vector comprising such a nucleic acid.

A recombinant host cell comprising a nucleic acid or the vector of the invention is also provided. Such a recombinant host cell may be used to produce a specific binding member of the invention. Thus, also provided is a method of producing a specific binding member or antibody molecule of the invention, the method comprising culturing the recombinant host cell under conditions for production of the specific binding member or antibody molecule. The method may further comprise a step of isolating and/or purifying the specific binding member or antibody molecule.

The specific binding members and antibodies of the present invention are expected to find application in therapeutic applications, in particular therapeutic applications in humans, such as cancer treatment. Thus, also provided is a pharmaceutical composition comprising a specific binding member or antibody molecule according to the invention and a pharmaceutically acceptable excipient.

The present invention also provides a specific binding member or antibody molecule of the invention, for use in a method of treating cancer in a patient. Also provided is a method of treating cancer in a patient, wherein the method comprises administering to the patient a therapeutically effective amount of a specific binding member or antibody molecule according to the invention. Further provided is the use of a specific binding member or antibody molecule according to the invention for use in the manufacture of a medicament for the treatment of cancer in a patient. A patient, as referred to herein, is preferably a human patient. The treatment may further comprise administering an anti-tumour vaccine and/or a chemotherapeutic agent to the patient.

The present inventors have shown that treatment of TILs with a specific binding member according to the present invention comprising a LAG-3 antigen-binding site located in a CH3 domain of the specific binding member, in combination with an anti-PD-L1 antibody results in reduced LAG-3 expression by the TILs. The reduction in LAG-3 expression is expected to reduce the inhibitory effect of LAG-3 and thereby allow the TILs to overcome exhaustion. Once the TILs become activated, it is expected that they will be able to recognise neo-antigens expressed by the tumour and mount a response against it, thereby reducing the tumour burden.

The specific binding member of the invention may therefore be administered to a patient in combination with a second specific binding member which binds to PD-L1, such as an antibody molecule which binds to PD-L1.

Thus, in a further aspect, the present invention relates to a specific binding member, or antibody molecule of the invention, for use in a method of treating cancer in a patient, wherein the method comprises administering the specific binding member, or antibody molecule of the invention, and a second specific binding member which binds to PD-L1 to the patient.

The present invention also relates to a specific binding member which binds to PD-L1 for use in a method of treating cancer in a patient, wherein the method comprises administering specific binding member and a specific binding member, or antibody molecule of the invention to the patient.

The invention further relates to a method of treating cancer in a patient, wherein the method comprises administering a therapeutically effective amount of a specific binding member, or antibody molecule, according to the invention and a second specific binding member which binds to PD-L1 to the patient. Also provided is the use of a specific binding member or antibody molecule according to the invention for the manufacture of a medicament for the treatment of cancer in a patient, wherein the treatment comprises administering the specific binding member, or antibody molecule, according to the invention and a second specific binding member which binds to PD-L1 to the patient.

The specific binding member, or antibody molecule of the invention and the specific binding member which binds to PD-L1 may be administered to the patient simultaneously, separately, or sequentially.

In this context, the specific binding member, or antibody molecule of the invention, may not comprise a CDR-based antigen binding site for a second antigen. The specific binding member, or antibody molecule of the invention, may therefore only bind to LAG-3.

The specific binding member which binds PD-L1 may be antibody molecule, or fragment thereof. Antibody molecules which bind PD-L1 are known in the art. The antibody molecule may be human or humanised. The antibody molecule is preferably a monoclonal antibody molecule. Examples of antibody molecules are the immunoglobulin isotypes, such as immunoglobulin G, and their isotypic subclasses, such as IgG1, IgG2, IgG3 and IgG4, as well as fragments thereof. The specific binding member which binds PD-L1 does not comprise a LAG-3 antigen-binding site.

BRIEF DESCRIPTION OF THE FIGURES

FIG. 1A shows a sequence alignment of the nine Fcabs identified following the second affinity maturation, FS18-7-32; FS18-7-33; FS18-7-36; FS18-7-58; FS18-7-62; FS18-7-65; FS18-7-78; FS18-7-88; and FS18-7-95, against the parental Fcab, FS18-7-9. The sequence identity of each of these Fcabs with the sequence of the parental Fcab, FS18-7-9, is shown in FIG. 1B.

DETAILED DESCRIPTION

Figure 2:
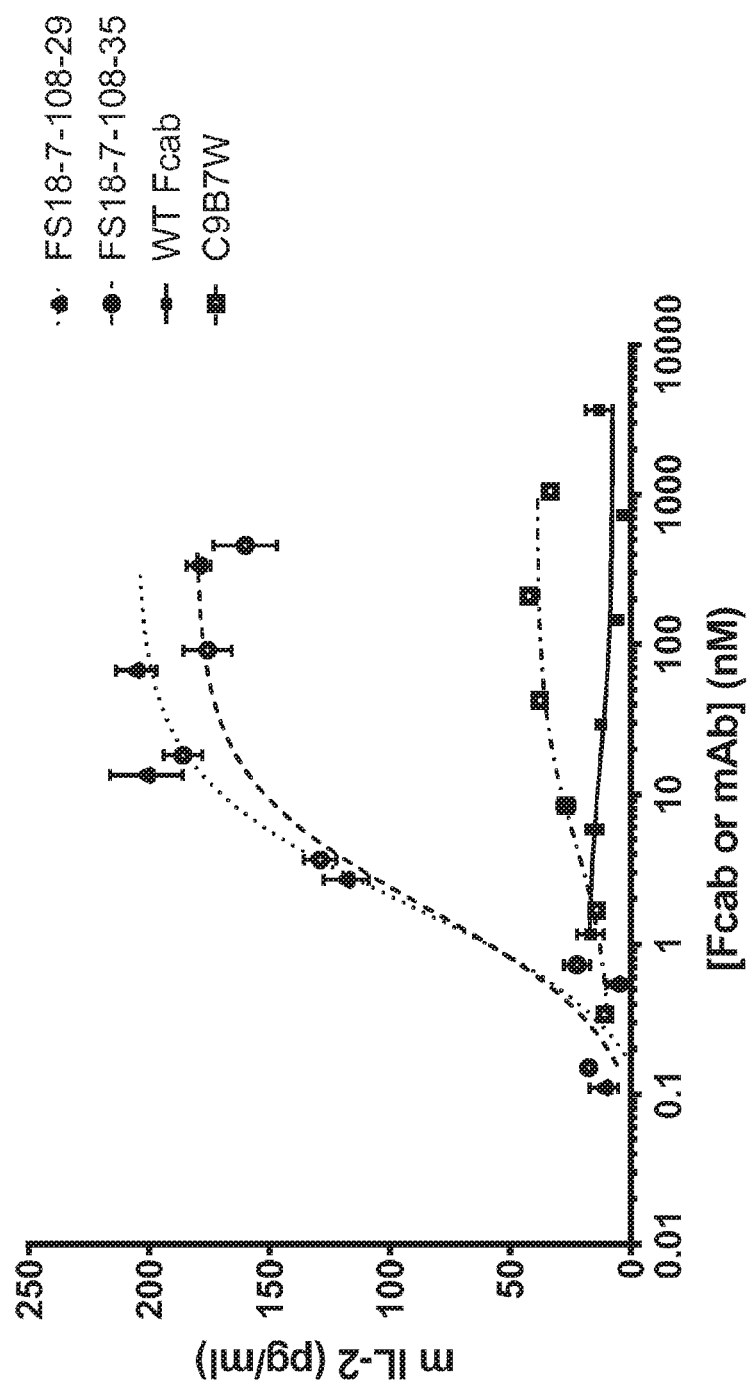
FIG. 2 shows that the surrogate anti-mouse LAG-3 Fcabs inhibit mouse LAG-3 leading to release of mIL-2 in a DO11.10 T-cell activation assay. The benchmark anti-mouse LAG-3 mAb, C9B7W, shows an increase in mIL-2 release, however the maximal release was significantly less than that of the anti-mouse LAG-3 Fcabs. The WT Fcab showed no activity in this assay.

The present invention relates to specific binding members which bind to LAG-3. Specifically, the specific binding members of the present invention comprise a LAG-3 antigen binding site located in a constant domain of the specific binding member. The term "LAG-3" may refer to human LAG-3, murine LAG-3, and/or cynomolgus monkey LAG-3, unless the context requires otherwise. Preferably the term "LAG-3" refers to human LAG-3.

The term "specific binding member" describes an immunoglobulin, or fragment thereof, comprising a constant domain, preferably a CH3 domain, comprising a LAG-3 antigen-binding site. Preferably, the specific binding member comprises a CH2 and CH3 domain, wherein the CH2 or CH3 domain, preferably the CH3 domain, comprises a LAG-3 antigen-binding site. In a preferred embodiment, the specific binding member further comprises an immunoglobulin hinge region, or part thereof, at the N-terminus of the CH2 domain. Such a molecule is also referred to as an antigen-binding Fc fragment, or Fcab™, herein. The specific binding member may be partly or wholly synthetically produced.

The term "specific binding member", as used herein, thus includes fragments, provided said fragments comprise a LAG-3 antigen binding site located in a constant domain, such as a CH1, CH2, or CH3 domain, preferably a CH3 domain, of the specific binding member. Unless the context requires otherwise, the term "specific binding member", as used herein, is thus equivalent to "specific binding member or fragment thereof".

In a preferred embodiment, the specific binding member is an antibody molecule. The term "antibody molecule" encompasses fragments of antibody molecules, provided such fragments comprise a constant domain, such as a CH1, CH2, or CH3 domain, preferably a CH3 domain, comprising a LAG-3 antigen-binding site. The antibody molecule may be human or humanised. The antibody molecule is preferably a monoclonal antibody molecule. Examples of antibody molecules are the immunoglobulin isotypes, such as immunoglobulin G, and their isotypic subclasses, such as IgG1, IgG2, IgG3 and IgG4, as well as fragments thereof.

It is possible to take monoclonal and other antibodies and use techniques of recombinant DNA technology to produce other antibodies or chimeric molecules which retain the specificity of the original antibody. Such techniques may involve introducing the CDRs, or variable regions, into a different immunoglobulin. Introduction of the CDRs of one immunoglobulin into another immunoglobulin is described for example in EP-A-184187, GB 2188638A or EP-A-239400. Similar techniques could be employed for the relevant constant domain sequences providing the LAG-3 antigen binding site. Alternatively, a hybridoma or other cell producing a specific binding member may be subject to genetic mutation or other changes, which may or may not alter the binding specificity of antibodies produced.

As antibodies can be modified in a number of ways, the term "specific binding member" should be construed as covering antibody fragments, derivatives, functional equivalents and homologues of antibodies, whether natural or wholly or partially synthetic. An example of an antibody fragment comprising a CH3 domain is an Fc domain of an antibody. An example of an antibody fragment comprising both CDR sequences and CH3 domain is a minibody, which comprises an scFv joined to a CH3 domain (Hu et al. (1996), Cancer Res., 56(13):3055-61).

The specific binding member of the present invention binds to LAG-3. Binding in this context may refer to specific binding. The term "specific" may refer to the situation in which the specific binding member will not show any significant binding to molecules other than its specific binding partner(s), here LAG-3. The term "specific" is also applicable where the specific binding member is specific for particular epitopes, such as epitopes on LAG-3, that are carried by a number of antigens in which case the specific binding member will be able to bind to the various antigens carrying the epitope.

LAG-3 shares 40% sequence identity with CD4, its most closely related protein. The present inventors tested the FS18-7-9 Fcab, which comprises the amino acid sequences set forth in SEQ ID NOs 1 to 3, for binding to CD4. The FS18-7-9 Fcab showed no binding to CD4, demonstrating that the specific binding member binds LAG-3 specifically. Thus, in a preferred embodiment, the LAG-3 binding site of a specific binding member of the present invention does not bind, or does not show any significant binding, to CD4.

A specific binding member of the invention preferably comprises a LAG-3 antigen binding site. The LAG-3 antigen binding site is located in a constant domain of the specific binding member, such as a CH1, CH2, CH3 or CH4 domain. Preferably, the LAG-3 antigen binding site is located in the CH3 domain of the specific binding member. The LAG-3 binding site preferably comprises the amino acid sequences WDEPWGED (SEQ ID NO: 1) and PYDRWVWPDE. (SEQ ID NO: 3). These sequences were present in all of the lead anti-LAG-3 Fcab clones identified by the present inventors following an extensive screening and characterisation program as described in the examples.

The amino acid sequences set forth in SEQ ID NOs 1 and 2 are preferably located in structural loops of the constant domain of the specific binding member. The introduction of sequences into the structural loop regions of antibody constant domains to create new antigen-binding sites is described, for example, in WO2006/072620 and WO2009/132876.

The structural loops of antibody constant domains include the AB, CD and EF loops. In the CH3 domain, the AB, CD, and EF loops are located at residues 11-18, 43-78 and 92-101 of the CH3 domain, where the amino acid residue numbering is according to the ImMunoGeneTics (IMGT) numbering scheme. The amino acid sequence set forth in SEQ ID NO: 1 is preferably located in the AB loop of the constant domain. The amino acid sequence set forth in SEQ ID NO: 3 is preferably located in the EF loop of the constant domain. More preferably, the amino acid sequence set forth in SEQ ID NO: 1 is located at residues 11 to 18 of the CH3 domain; and/or the amino acid sequence set forth in SEQ ID NO: 3 is located at residues 92 to 101 of the CH3 domain, wherein the amino acid residue numbering is according to the IMGT numbering scheme.

In addition, the specific binding member preferably comprises the amino acid sequence set forth in SEQ ID NO: 2, 8, 13, 18, 23, 28, 33, 38, 43, or 48, more preferably SEQ ID NO: 2, 28, or 38, yet more preferably SEQ ID NO: 2, in a structural loop of a constant domain of the specific binding member. The structural loop is preferably the CD loop and the constant domain is preferably the CH3 domain. The amino acid sequence set forth in SEQ ID NO: 2, 8, 13, 18, 23, 28, 33, 38, 43, or 48 is preferably located at residues 43 to 78 of the CH3 domain, wherein the amino acid residue numbering is according to the IMGT numbering scheme.

A specific binding member of the invention may further comprise a glutamic acid residue (E) at position 36 and/or a tyrosine residue (Y) at position 85.2 of the CH3 domain (as shown in FIG. 1A), wherein the amino acid residue numbering is according to the IMGT numbering scheme. In particular, a specific binding member which comprises the CD structural loop region set forth in SEQ ID NO: 8 preferably further comprises a glutamic acid residue (E) at position 36 of the CH3 domain. Similarly, a specific binding member which comprises the CD structural loop region set forth in SEQ ID NO: 18 preferably further comprises a tyrosine residue (Y) at position 85.2 of the CH3 domain.

In a preferred embodiment, the specific binding member of the invention comprises a CH3 domain which comprises, has, or consists of the sequence set forth in SEQ ID NO: 5, 10, 15, 20, 25, 30, 35, 40, 45, or 50, preferably a CH3 domain with the sequence set forth in SEQ ID NO: 5, 30, or 40, more preferably, a CH3 domain with the sequence set forth in SEQ ID NO: 5.

The specific binding member of the invention may comprise a CH3 domain which comprises, has, or consists of the sequence set forth in SEQ ID NO: 5, 10, 15, 20, 25, 30, 35, 40, 45, or 50, wherein the CH3 domain sequence further comprises a lysine residue (K) at the immediate C-terminus of the sequence shown in SEQ ID NO: 5, 10, 15, 20, 25, 30, 35, 40, 45, or 50. Thus, for example, the specific binding member of the invention may comprise a CH3 domain which comprises, has, or consists of the sequence set forth in SEQ ID NO: 5 with a lysine residue at the C-terminus of the sequence shown in SEQ ID NO: 5. The sequence of such a CH3 domain would then be as follows:

```
                                            (SEQ ID NO: 135)
GQPREPQVYTLPPSWDEPWGEDVSLTCLVKGFYPSDIAVEWESNGQPENN
YKTTPPVLDSDGSFFLYSKLTVPYDRWVWPDEFSCSVMHEALHNHYTQKS
LKSPGK
```

In addition, the specific binding member of the invention may comprise a CH2 domain of an immunoglobulin G molecule, such as a CH2 domain of an IgG1, IgG2, IgG3, or IgG4 molecule. Preferably the specific binding member of the invention comprises a CH2 domain of an IgG1 molecule. The CH2 domain may have the sequence set forth in SEQ ID NO: 53.

The CH2 domain of the specific binding member may comprise a mutation to reduce or abrogate binding of the CH2 domain to one or more Fcγ receptors, such as FcγRI, FcγRIIa, FcγRIIb, FcγRIII and/or to complement. CH2 domains of human IgG domains normally bind to Fcγ receptors and complement and the inventors postulate that reduced binding to Fcγ receptors will reduce the antibody-dependent cell-mediated cytotoxicity (ADCC) and reduced binding to complement will reduce the complement-dependent cytotoxicity (CDC) activity of the specific binding member. Mutations for reduce or abrogate binding of the CH2 domain to one or more Fcγ receptors and complement are known and include the "LALA mutation" described in Bruhns, et al. (2009) and Xu et al. (2000). Thus, the specific binding member may comprise a CH2 domain, wherein the CH2 domain comprises alanine residues at positions 4 and 5 of the CH2 domain, wherein the numbering is according to the MGT numbering scheme. For example, the specific binding member comprises an IgG1 CH2 domain which comprises, has, or consists of the sequence set forth in SEQ ID NO: 54.

A specific binding member according to the present invention may comprise a second antigen-binding site, preferably a CDR-based antigen binding site. The term "CDR-based antigen binding site" refers to the antigen-binding site of a specific binding member variable region which is composed of six CDR residues.

The second antigen-binding site is preferably specific for a tumour antigen. More preferably, the second antigen-binding site may bind to a molecule which is an immune system modulator, such as an immunomodulatory receptor or a ligand for an immunomodulatory receptor. For example, the second antigen-binding site may bind to a molecule which is an immune system inhibitor or activator, preferably an immune system inhibitor. Examples of immune system inhibitors include cytotoxic T-lymphocyte-associated protein 4 (CTLA-4), T cell immunoglobulin and mucin-domain containing-3 (TIM-3), and Colony stimulating factor 1 receptor (CSF1R).

The antibody molecules against a given antigen, such as a tumour antigen, and determination of the CDR sequences of such an antibody molecule, is well within the capabilities of the skilled person and many suitable techniques are known in the art. Furthermore, antibodies, including the CDR sequences, against various immune system modulators are known in the art. Thus, the skilled person would have no difficulty in preparing a specific binding member comprising in addition to a LAG-3 binding site as described herein a CDR-based antigen-binding site for a second antigen.

The specific binding members of the present invention may also comprise variants of the structural loop, CH3 domain, CH2 domain, CH2 and CH3 domain, CDR, VH domain, VL domain, light chain or heavy chain sequences disclosed herein. Suitable variants can be obtained by means of methods of sequence alteration, or mutation, and screening. In a preferred embodiment, a specific binding member comprising one or more variant sequences retains one or more of the functional characteristics of the parent specific binding member, such as binding specificity and/or binding affinity for LAG-3. For example, a specific binding member comprising one or more variant sequences preferably binds to LAG-3 with the same affinity, or a higher affinity, than the (parent) specific binding member. The parent specific binding member is a specific binding member which does not comprise the amino acid substitution(s), deletion(s), and/or insertion(s) which have been incorporated into the variant specific binding member.

For example, a specific binding member of the invention may comprise a structural loop, CH3 domain, CH2 domain, CH2 and CH3 domain, CDR, VH domain, VL domain, light chain or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a structural loop, CH3 domain, CH2 domain, CH2 and CH3 domain, CDR, VH domain, VL domain, light chain or heavy chain sequence disclosed herein.

In a preferred embodiment, the specific binding member of the invention comprises a CH3 domain sequence which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH3 domain sequence set forth in SEQ ID NO: 4, 5, or 135.

In a further preferred embodiment, the specific binding member of the invention comprises a CH3 and CH2 domain sequence, which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 and CH3 domain sequence set forth in SEQ ID NO: 6 or 7.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

A specific binding member of the invention may also comprise a structural loop, CH3 domain, CH2 domain, CH2 and CH3 domain, CDR, VH domain, VL domain, light chain or heavy chain sequence which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a structural loop, CH3 domain, CH2 domain, CH2 and CH3 domain, CDR, VH domain, VL domain, light chain or heavy chain sequence disclosed herein. In particular, alterations may be made in one or more framework regions of the specific binding member.

In a preferred embodiment, the specific binding member of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NO: 4, 5, or 135.

In a further preferred embodiment, the specific binding member of the invention comprises a CH3 and CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 and CH3 domain sequence set forth in SEQ ID NO: 6 or 7.

Also contemplated is a specific binding member which competes with a specific binding member of the invention for binding to LAG-3, or which binds to the same epitope on LAG-3 as a specific binding member of the invention, wherein the specific binding member preferably comprises a LAG-3 antigen binding site located in a CH3 domain of the specific binding member. Methods for determining competition for an antigen by two antibodies are known in the art. For example, competition of binding to en antigen by two antibodies can be determined using BIAcore. Methods for mapping the epitope bound by an antibody are similarly known in the art.

The specific binding member of the invention preferably binds to LAG-3 with an affinity ($K_D$) of $1 \times 10^{-9}$ M or an affinity which is greater. For example, the specific binding member of the invention may bind to LAG-3 with an affinity ($K_D$) of $8 \times 10^{-10}$ M, or an affinity which is greater.

The binding affinity of a specific binding member to a cognate antigen, such as LAG-3 can be determined by surface plasmon resonance (SPR), for example. The binding affinity of a specific binding member to a cognate antigen, such as LAG-3, expressed on a cell surface can be determined by flow cytometry.

Fcabs have a smaller binding interface than monoclonal antibodies as the binding sites of Fcabs form a relatively compact antibody fragment with two binding sites situated in close proximity. In contrast, the Fab arms of a typical mAb are separated by a flexible hinge region. The two antigen binding sites of an Fcab are also spatially close to each other, as compared with those of a typical mAb. Based on this smaller binding interface and reduced flexibility of the two binding sites it was surprising that the anti-LAG-3 Fcabs were able to bind to and inhibit LAG-3 with similar affinity and potency as a monoclonal antibody benchmark.

The specific binding member of the present invention is preferably capable of binding to LAG-3 expressed on the surface of a cell. The cell is preferably a cancer cell.

Where the specific binding member comprises a second antigen-binding site, such as CDR-based antigen binding site, specific for a second antigen, the specific binding member is preferably capable of simultaneously binding to LAG-3 and the second antigen. Preferably, the specific binding member is capable of simultaneously binding to LAG-3 and the second antigen, wherein the LAG-3 and the second antigen are expressed on the surface of a single cell, or on the surface of two separate cells.

The specific binding member of the invention may bind to human LAG-3, murine LAG-3, and/or cynomolgus monkey LAG-3. Preferably, the specific binding member of the invention binds to human LAG-3.

In one embodiment, the specific binding member of the invention is not a specific binding member, such as an antibody molecule, which comprises an antigen binding site, such as a CDR-based antigen-binding site, for PD-L1.

In certain examples, the specific binding member of the invention is not a specific binding member, such as an antibody molecule, which comprises (i) a CDR-based antigen binding site for PD-L1; and (ii) a LAG-3 antigen binding site located in a CH3 domain of the specific binding member.

In a further example, the specific binding member of the invention is not a specific binding member, such as an antibody molecule, which binds to PD-L1 and LAG-3, wherein the antibody molecule comprises:

(i) a CDR-based antigen binding site for PD-L1; and
(ii) a LAG-3 antigen binding site located in a CH3 domain of the antibody molecule, wherein the LAG-3 binding site comprises the amino acid sequences WDEPWGED (SEQ ID NO: 1) and PYDRWVWPDE, (SEQ ID NO: 3), and wherein the amino acid sequence WDEPWGED is located in a first structural loop of the CH3 domain and the amino acid sequence PYDRWVWPDE is located in a second structural loop of the CH3 domain. The specific binding member of the present invention may be conjugated to a therapeutic agent or detectable label. In this case, the specific binding member may be referred to as a conjugate. For example, the specific binding member may be conjugated to an immune system modulator, cytotoxic molecule, radioisotope, or detectable label. The immune system modulator or cytotoxic molecule may be a cytokine. The detectable label may be a radioisotope, e.g. a non-therapeutic radioisotope.

The specific binding member may be conjugated to the therapeutic agent or detectable label, by means of a peptide bond or linker, i.e. within a fusion polypeptide comprising said therapeutic agent or detectable label and the specific binding member or a polypeptide chain component thereof. Other means for conjugation include chemical conjugation, especially cross-linking using a bifunctional reagent (e.g.

employing DOUBLE-REAGENTS™ Cross-linking Reagents Selection Guide, Pierce).

The specific binding member and the therapeutic agent or detectable label may thus be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example the specific binding member and therapeutic or diagnostic agent may be covalently linked. For example by peptide bonds (amide bonds). Thus, the specific binding member and therapeutic or diagnostic agent may be produced (secreted) as a single chain polypeptide.

The invention also provides isolated nucleic acids encoding the antibodies molecules of the invention. The skilled person would have no difficulty in preparing such nucleic acids using methods well-known in the art. An isolated nucleic acid may be used to express the specific binding member of the invention, for example, by expression in a bacterial, yeast, insect or mammalian host cell. A preferred host cell is a mammalian cell such as a CHO, HEK or NS0 cell. The nucleic acid will generally be provided in the form of a recombinant vector for expression.

The isolated nucleic acid may, for example, comprise the sequence set forth in SEQ ID NO: 136, 4, 9, 14, 19, 24, 29, 34, 39, 44, or 49, which encode the CH3 domains of FS18-7-9 (CHO codon optimised nucleotide sequence), FS18-7-9 (HEK293-expressed nucleotide sequence), FS18-7-32, FS18-7-33, FS18-7-36, FS18-7-58, FS18-7-62, FS18-7-65, FS18-7-78, FS18-7-88, and FS18-7-95, respectively.

In vitro host cells comprising such nucleic acids and vectors are part of the invention, as is their use for expressing the specific binding members of the invention, which may subsequently be purified from cell culture and optionally formulated into a pharmaceutical composition. The present invention thus further provides a method of producing the specific binding member of the invention, comprising culturing the recombinant host cell of the invention under conditions for production of the specific binding member. Methods for culturing suitable host cells as mentioned above are well-known in the art. The method may further comprise isolating and/or purifying the specific binding member. The method may also comprise formulating the specific binding member into a pharmaceutical composition, optionally with a pharmaceutically acceptable excipient or other substance as described below.

LAG-3 is known to be expressed on cells of the immune system. In particular, LAG-3 is known to be expressed on exhausted T cells within the tumour environment, and a limited number of cancer cells. In addition, the present inventors have shown that the use of a specific binding member which binds to LAG-3 is effective in suppressing tumour growth in syngeneic mouse models of cancer.

Thus, a specific binding member of the invention may be used in a method of treating cancer in a patient. The patient is preferably a human patient.

Cells of the cancer to be treated using the specific binding member of the invention may express LAG-3, e.g. on their cell surface. In one embodiment, cells of the cancer to be treated may have been determined to express LAG-3, e.g. on their cell surface. For example, B cell lymphomas have been shown to express LAG-3 on their cell surface. Methods for determining the expression of an antigen on a cell surface are known in the art and include, for example, flow cytometry.

Example 3 below shows that the specific binding members of the present invention can be used to treat tumours with high levels of LAG-3-expressing immune cells, such as LAG-3-expressing TILs, in mice. Thus, in addition, or alternatively, tumours of the cancer to be treated using the specific binding members of the invention may comprise LAG-3 expressing immune cells. LAG-3 expressing immune cells, such as LAG-3 expressing TILs, are present between tumour cells in many cancers. In one embodiment, tumours of the cancer to be treated using the specific binding member of the invention have been determined to contain LAG-3 expressing immune cells. Methods for determining the presence of LAG-3 expressing immune cells in a tumour or in the periphery of the tumour are known in the art.

A cancer to be treated using a specific binding member of the invention may be selected from the group consisting of Hodgkin's lymphoma, non-Hodgkin's lymphoma (such as diffuse large B-cell lymphoma, follicular lymphoma, indolent non-Hodgkin's lymphoma, mantle cell lymphoma), ovarian cancer, prostate cancer, colorectal cancer, fibrosarcoma, renal cell carcinoma, melanoma, pancreatic cancer, breast cancer, glioblastoma multiforme, lung cancer (such as non-small cell lung cancer), head and neck cancer (such as head and neck squamous cell carcinoma), stomach cancer (gastric cancer), bladder cancer, cervical cancer, uterine cancer, vulvar cancer, testicular cancer, penile cancer, leukemia (such as chronic lymphocytic leukemia, myeloid leukemia, acute lymphoblastoid leukaemia, or chronic lymphoblastoid leukaemia), multiple myeloma, squamous cell cancer, testicular cancer, esophageal cancer (such as adenocarcinoma of the gastroesophageal junction), Kaposi's sarcoma, and central nervous system (CNS) lymphoma, hepatocellular carcinoma, nasopharyngeal cancer, Merkel cell carcinoma, and mesothelioma. Tumours of these cancers are known, or expected, to contain immune cells, such as TILs, expressing LAG-3.

Treatment of renal cell carcinoma, lung cancer (such as non-small cell lung cancer), nasopharyngeal cancer, colorectal cancer, melanoma, stomach cancer (gastric cancer), esophageal cancer (such as adenocarcinoma of the gastroesophageal junction), ovarian cancer, cervical cancer, bladder cancer, head and neck cancer (such as head and neck squamous cell carcinoma), leukemia (such as chronic lymphocytic leukemia, Hodgkin's lymphoma, non-Hodgkin's lymphoma (such as diffuse large B-cell lymphoma, indolent non-Hodgkin's lymphoma, mantle cell lymphoma), and multiple myeloma using anti-LAG-3 antibodies has been investigated in clinical trials and shown promising results. Thus, the cancer to be treated using the specific binding members of the present invention may be a renal cell carcinoma, lung cancer (such as non-small cell lung cancer), nasopharyngeal cancer, colorectal cancer, melanoma, stomach cancer (gastric cancer), esophageal cancer (such as adenocarcinoma of the gastroesophageal junction), ovarian cancer, cervical cancer, bladder cancer, head and neck cancer (such as head and neck squamous cell carcinoma), leukemia (such as chronic lymphocytic leukemia, Hodgkin's lymphoma, non-Hodgkin's lymphoma (such as diffuse large B-cell lymphoma, indolent non-Hodgkin's lymphoma, mantle cell lymphoma), or multiple myeloma.

Preferred cancers for treatment using the specific binding members of the present invention are lung cancer (such as non-small-cell lung cancer), bladder cancer, head and neck cancer (squamous cell carcinoma of the head and neck), diffuse large B cell lymphoma, gastric cancer, pancreatic cancer and hepatocellular carcinoma. Tumours of these cancers are known to comprise LAG-3 expressing immune cells and to express PD-L1 either on their cell surface or to comprise immune cells expressing PD-L1.

Where the application refers to a particular type of cancer, such as breast cancer, this refers to a malignant transformation of the relevant tissue, in this case a breast tissue. A cancer which originates from malignant transformation of a different tissue, e.g. ovarian tissue, may result in metastatic lesions in another location in the body, such as the breast, but is not thereby a breast cancer as referred to herein but an ovarian cancer.

The cancer may be a primary or secondary cancer. Thus, the specific binding member of the present invention may be for use in a method of treating cancer in a patient, wherein the cancer is a primary tumour and/or a tumour metastasis.

The specific binding members of the invention are designed to be used in methods of treatment of patients, preferably human patients. Specific binding members will usually be administered in the form of a pharmaceutical composition, which may comprise at least one component in addition to the specific binding member, such as a pharmaceutically acceptable excipient. For example, a pharmaceutical composition of the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be by injection, e.g. intravenous or subcutaneous. The specific binding member may be administered intravenously, or subcutaneously.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the specific binding member, or pharmaceutical composition comprising the specific binding member, is preferably in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition comprising a specific binding members according to the present invention may be administered alone or in combination with other treatments, concurrently or sequentially or as a combined preparation with another therapeutic agent or agents, dependent upon the condition to be treated. For example, a specific binding member of the invention may be administered in combination with an existing therapeutic agent for the disease to be treated, e.g. a cancer as mentioned above. For example, a specific binding member of the present invention may be administered to the patient in combination with a second anti-cancer therapy, such as chemotherapy, anti-tumour vaccination (also referred to as a cancer vaccination), radiotherapy, immunotherapy, an oncolytic virus, chimeric antigen receptor (CAR) T-cell therapy, or hormone therapy.

It is expected that the specific binding member of the invention may act as an adjuvant in anti-cancer therapy, such as chemotherapy, anti-tumour vaccination, or radiotherapy. Without wishing to be bound by theory, it is thought that administration of the specific binding member to the patient as part of chemotherapy, anti-tumour vaccination, or radiotherapy will trigger a greater immune response against the cancer associated antigen LAG-3, than is achieved with chemotherapy, anti-tumour vaccination, or radiotherapy alone. For example, anti-LAG-3 therapies have shown good efficacy in treating viral based pathologies in mice (Blackburn S D, et al., 2009, Nature Immunology 10 (1): 29-37).

A method of treating cancer in a patient may thus comprise administering to the patient a therapeutically effective amount of a specific binding member according to the present invention in combination with a chemotherapeutic agent, anti-tumour vaccine, radionuclide, immunotherapeutic agent, oncolytic virus. CAR-T cell, or agent for hormone therapy. The chemotherapeutic agent, anti-tumour vaccine, radionuclide, immunotherapeutic agent, oncolytic virus, CAR-T cell, or agent for hormone therapy is preferably a chemotherapeutic agent, anti-tumour vaccine, radionuclide, immunotherapeutic agent, oncolytic virus, CAR-T cell, or agent for hormone therapy for the cancer in question, i.e. a chemotherapeutic agent, anti-tumour vaccine, radionuclide, immunotherapeutic agent, oncolytic virus, CAR-T cell, or agent for hormone therapy which has been shown to be effective in the treatment of the cancer in question. The selection of a suitable chemotherapeutic agent, anti-tumour vaccine, radionuclide, immunotherapeutic agent, oncolytic virus, CAR-T cell, or agent for hormone therapy which have been shown to be effective for the cancer in question is well within the capabilities of the skilled practitioner.

For example, where the method comprises administering to the patient a therapeutically effective amount of a specific binding member according to the present invention in combination with a chemotherapeutic agent, the chemotherapeutic agent may be selected from the group consisting of: taxanes, cyctotoxic antibiotics, tyrosine kinase inhibitors, PARP inhibitors, B_RAF enzyme inhibitors, alkylating agents, platinum analogs, nucleoside analogs, thalidomide derivatives, antineoplastic chemotherapeutic agents and others. Taxanes include docetaxel, paclitaxel and nab-paclitaxel; cytotoxic antibiotics include actinomycin, bleomycin, anthracyclines, doxorubicin and vairubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide, temozolomide; platinum analogs include carboplatin, cisplatin and oxaliplatin; nucleoside analogs include gemcitabine and azacitidine; antineoplastics include fludarabine. Other chemotherapeutic agents suitable for use in the present invention include methotrexate, defactinib, entinostat, pemetrexed, capecitabine; eribulin, irinotecan, fluorouracil, and vinblastine.

Vaccination strategies for the treatment of cancers has been both implemented in the clinic and discussed in detail within scientific literature (such as Rosenberg, S. 2000 Development of Cancer Vaccines). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

Administration may be in a "therapeutically effective amount", this being sufficient to show benefit to a patient. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of specific binding member, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of specific binding members are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for a specific binding member being administered, may be used. A therapeutically effective amount or suitable dose of a specific binding member can be determined by comparing it's in vitro activity and in vivo activity in an animal model. Methods for extrapolation of effective dosages in mice and other test animals to humans are known. The precise dose will depend upon a number of factors, including whether the size and location of the area to be treated, and the precise nature of the specific binding member. Treatments may be repeated at daily, twice-weekly, weekly or monthly intervals, at the discretion of the physician. Treatment may be given before, and/or after surgery, and may be administered or applied directly at the anatomical site of surgical treatment.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1 Selection and Characterisation of Fcab Molecules 1.1 Naïve Selection and Affinity Maturation of Anti-Human LAG-3 Fcabs 1.1.1 Naïve Selection Naïve phage libraries displaying the CH3 domain of human IgG1 (IMGT numbering 1.4-130) with randomisation within the AB (residues 14-18) and EF (residues 92-101) loops were used for selection with recombinant Fc-tagged human LAG-3 (LAG-3 Fc) antigen (R&D systems, 2319-L3-050). The libraries were selected in three rounds using antigen captured on Protein A (Life Technologies, 10002D) or Protein G (Life Technologies, 10004D) beads. The outputs were screened by ELISA and positive binders sub-cloned and expressed as soluble Fcabs (containing a truncated hinge) in *Pichia pastoris* using EasySelect *Pichia* Expression Kit (Life Technologies, K1740-01). The Fcabs were then screened for binding to recombinant human LAG-3 Fc on the Biacore 3000 (GE Healthcare). Briefly, LAG-3 Fc (R&D systems, 2319-L3-050) was coupled at a density of 7200 RU to a CM5 chip (GE Healthcare, BR-100012) using amine coupling (GE Healthcare, BR-1000-50). Fcabs were diluted in HBS-P (GE Healthcare, BR100368) buffer and injected at 250 nM, 500 nM and 1000 nM for 3 min and then allowed to dissociate in buffer for 5 min. Reference subtracted data (LAG-3 Fc flow cell 2—blank flow cell) was analyzed using BIAevaluation 3.2 software to identify binding. Fcabs were then tested for binding to HEK cell-expressed human LAG-3 (LAG-3 cloned into pcDNA5FRT vector [Life Technologies, V6010-20] [See section 1.4.5 for methodology]). Briefly, HEK 293 cells overexpressing human LAG-3 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014) and seeded in V-bottom 96-well plates at $2\times10^5$ cells/well. Fcabs were incubated with the cells at 5 µM in a 100 µl volume for 1 h at 4° C. The plates were washed the secondary antibody (Anti-human Fc-488, Jackson ImmunoResearch, 109-546-098) was diluted 1:1000 in PBS and 100 µl was added to the cells and incubated for 30 min at 4° C. The plates were washed and the cells were resuspended in 100 µl PBS containing 1 µg/ml DAPI (Biotium, 40043). The plate was read on a BD FACSCanto II cytometer (BD Biosciences) and the data analysed using FlowJoX. The Fcabs were then expressed in mammalian cells by transformation using lipofectamine (Life Technologies, 11668-019) into FIp-in T-Rex 293 cells (Life Technologies, R780-07). The LAG-3 binding Fcabs were tested for inhibition of binding of human MHC class II on A375 cells (ATCC, CRL-1619) to recombinant LAG-3 Fc (using the methodology in example 1.6). 54 unique Fcab sequences were identified from three rounds of phage selection, and 12 of these Fcabs were determined to bind to LAG-3 Fc by BIAcore analysis and/or bind to LAG-3 expressing HEK cells. Three of the selected Fcabs were also able to inhibit the interaction of LAG-3 with MHC class II and were selected for affinity maturation. The three Fcabs were termed FS18-3, FS18-7 and FS18-21.

1.1.2 Affinity Maturation

First Affinity Maturation

Six phage display affinity maturation libraries were constructed by randomising five residues in the AB loop (residues 14-18) and either five (residues 92-94 and 97-98) or eight (residues 92-94 and 97-101) residues in the EF loop of each of the three Fcabs identified using the naïve selection process described above.

The affinity maturation libraries were selected using recombinant human LAG-3 Fc (R&D systems, 2319-L3-050) and HEK cells expressing human LAG-3 (as described above). The outputs were screened by phage ELISA, the positive binders were subcloned and expressed as soluble Fcabs (containing a truncated hinge) in HEK Expi293 cells (Fcabs cloned into pTT5 vector [National Research Council of Canada] transfected using ExpiFectamine 293 Transfection kit [Life Technologies, A14524] into Expi293F cells [Life technologies, A14527]). The HEK expressed soluble Fcabs were then screened for binding to cell expressed human LAG-3, binding to cell expressed cynomolgus LAG-3 (methodology as example 1.4.3), and the ability to block MHC class II binding to recombinant LAG-3 Fc (methodology as in example 1.6). The blocking Fcabs were further tested to determine whether they were able to reverse LAG-3 induced inhibition of IL-2 secretion in a T cell activation assay (methodology as in example 2.1). 61 unique anti-LAG-3 Fcabs were identified from the six affinity maturation libraries using these screening methods. Affinity matured Fcabs from the FS18-7 lineage were shown to have the highest level of cross—reactivity with cynomolgus monkey LAG-3. The three Fcabs from this lineage with the strongest binding to cynomolgus monkey LAG-3 Fc and the highest activity in the T cell activation assay (termed FS18-7-7, FS18-7-9, and FS18-7-11) were selected for further affinity maturation. These three Fcabs were also shown to block the interaction of LAG-3 Fc with cell expressed MHC class II.

Second Affinity Maturation

A pool of the three Fcabs (FS18-7-7, FS18-7-9, and FS18-7-11) from the first affinity maturation was used to create further affinity maturation libraries. The CD loop was hard randomized using randomized primers from ELLA Biotech. A portion of amino acid positions in the CD loop (residues 45.1-78) was randomized using an equimolar distribution of amino acids excluding cysteine. Error prone PCR was also carried out across the entire CH3 domain sequence to introduce additional mutations that might enhance binding.

The affinity maturation libraries were generated in phage and selections performed against biotinylated recombinant LAG-3 avi-Fc (BPS Bioscience, 71147) and HEK hLAG-3 cells and screened for binding to recombinant LAG-3 Fc (R&D systems, 2319-L3-050) by phage ELISA. 86 unique Fcabs (containing a truncated hinge) were expressed in HEK293F cells. Selected Fcabs were also screened for activity in a T cell activation assay as described above. The nine Fcabs identified during the second affinity maturation with the highest activity in the T cell activation assay (FS18-7-32; FS18-7-33; FS18-7-36; FS18-7-58; FS18-7-62; FS18-7-65; FS18-7-78; FS18-7-88; and FS18-7-95), as well as the parental Fcab clone, FS18-7-9, were then further characterised as described below. A sequence alignment of these nine Fcabs against the parental Fcab clone, FS18-7-9, is shown in FIG. 1A. FIG. 1B details the percentage sequence identity of each of the nine Fcab clones to the parental Fcab clone, FS18-7-9. Fcabs originating from affinity maturation of the two other parental Fcab clones, FS18-7-7 and FS18-7-11, were not as promising candidates as those originating from affinity maturation of FS18-7-9 and were therefore not pursued further.

1.2 Selection of Surrogate Fcab Specific for Mouse LAG-3

Fcab FS18-7, which was selected using the naïve selection protocol described above, was used to generate phage libraries to select against mouse LAG-3. Two rounds of affinity maturation were performed, and Fcab clones FS18-7-108-29 and FS18-7-108-35, which showed high-affinity, specific binding to mouse LAG-3 were selected following affinity maturation. The ability of FS18-7-108-29 and FS18-7-108-35 to inhibit mouse LAG-3 in a T cell activation assay was confirmed. Epitope mapping using the Octet (Forteo Bio) showed that the anti-mouse LAG-3 Fcabs compete with the anti-human LAG-3 Fcabs (selected following the second affinity maturation as described above) for binding to human LAG-3. There are between 4 and 8 residue differences between the anti-human LAG-3 and anti-mouse LAG-3 Fcabs. It is therefore expected that the anti-mouse LAG-3 Fcabs represent suitable surrogates for the binding and function of the anti-human LAG-3 Fcabs in mice.

1.3 Construction and Expression of Mock mAb$^2$

"mock" mAb$^2$ comprising the lead anti-human LAG-3 and anti-mouse LAG-3 Fcabs identified in 1.1 and 1.2 above were prepared in order to allow the characterisation of these Fcabs in mAb$^2$ format. These mock mAb$^2$ were prepared from the anti-LAG-3 Fcabs and the variable regions of anti-FITC antibody 4420 (see SEQ ID NO: 83, SEQ ID NO: 84, and SEQ ID NO: 85 for details) (Bedzyk, W. D., et al. 1989 and Bedzyk, W. D., et al. 1990). The mock mAb$^2$ were prepared both with (SEQ ID NO: 63, 65, 67, 69, 71, 73, 75, 77, 79, and 81) and without (SEQ ID NO: 64, 66, 68, 70, 72, 74, 76, 78, 80, and 82) the LALA mutation in the CH2 domain of the heavy chain (see section 1.5 below for details) and further comprised the light chain of the anti-FITC mAb 4420 (SEQ ID NO: 85). The mock mAb$^2$ were produced by transient expression in HEK293-6E cells and purified using mAb Select SuRe protein A columns.

1.4 Binding Affinity of Fcabs to LAG-3

1.4.1 Binding Affinity of Fcabs to Human LAG-3 as Determined by Surface Plasmon Resonance (SPR)

A BIAcore T200 (GE Healthcare) was used to measure the affinity of the anti-human LAG-3 Fcabs in the mock mAb$^2$ format for human LAG-3. Flow cell 4 of a CMS sensor chip (GE Healthcare, BR1005-30) was immobilised with human LAG-3-Fc (R&D Systems, 2319-L3-050), and flow cell 3 was immobilised with buffer for reference using the amine coupling kit (GE Healthcare, BR-1000-50). LAG-3-Fc was diluted to 5 µg/ml in sodium acetate pH5 (Forteo-Bio, 18-1069) and injected at a flow rate of 10 µl/min for 12 seconds followed by deactivation of the surface by injection of ethanolamine for 420 sec. The Immobilisation level was 158 RU. The mock mAb$^2$ (or control anti-human LAG-3 mAb, 25F7) were diluted in HBS-P buffer (GE Healthcare, BR-1003-68) in a 2-fold dilution series from 4 µg/ml. The control mAb/mock mAb$^2$ were injected with an association time of 240 seconds at 30 µl/min, and a dissociation time 300 seconds at 30 µl/min. The surface was regenerated using 25 mM NaOH for 30 seconds at 100 µl/min. The data was double reference subtracted and analysed using the BIAevaluation 3.2 software to calculate kinetic constants. The Fcabs in mock mAb$^2$ format had affinities for human LAG-3 in the range of 0.8-1.1 nM (Table 1), which is similar to the affinity of the benchmark anti-human LAG-3 mAb 25F7. This was surprising because Fcabs have a smaller binding interface than monoclonal antibodies as the binding sites of Fcabs form a relatively compact antibody fragment with two binding sites situated in close proximity. In contrast, the Fab arms of a typical mAb are separated by a flexible hinge region. Based on this smaller binding interface and the associated reduced flexibility of the two binding sites in the Fc region, it was unexpected that the anti-LAG-3 Fcabs were able to bind to and inhibit LAG-3 with similar affinity and potency as the benchmark antibody 25F7.

TABLE 1

Binding affinity of LAG-3 specific Fcabs in mock mAb² format to human LAG-3

| Anti-human LAG-3 Fcab in mock mAb² format and benchmark anti-human LAG-3 mAb, 25F7 | $K_D$ (M) |
| --- | --- |
| FS18-7-9 | $8.3 \times 10^{-10}$ |
| FS18-7-62 | $9.5 \times 10^{-10}$ |
| FS18-7-78 | $8.4 \times 10^{-10}$ |
| FS18-7-32 | $8.6 \times 10^{-10}$ |
| FS18-7-36 | $8.9 \times 10^{-10}$ |
| FS18-7-65 | $1.1 \times 10^{-9}$ |
| 25F7 | $3.2 \times 10^{-10}$ |

1.4.2 Binding Affinity of Surrogate Fcab Specific for Mouse LAG-3 to Mouse LAG-3 as Determined by SPR A Biacore 3000 (GE Healthcare) was used to measure the affinity of the surrogate Fcabs specific for mouse LAG-3 to mouse LAG-3. Amine coupling (amine coupling kit, GE Healthcare, BR-1000-50) was used to coat mLAG-3 Fc (R&D Systems, 3328-L3-050) diluted in 10 mM sodium acetate pH 5.0 (ForteBio, 18-1069) directly to a CM5 chip (GE Healthcare, BR-1000-12). Flow cell 1 was coated with Mouse Fc (SinoBiological, 51094-MNAH), and flow cell 2 was coated with mLAG-3 Fc at 950 RU. Fcabs were diluted in HBS-P buffer (GE Healthcare, BR-1003-68) and injected at various concentrations (fourfold dilutions from 100 nM) for 3 min at 20 µl/min and then allowed to dissociate in buffer for 12 min. The chip was regenerated by injection of 10 mM glycine pH 2.5 for 30 s at 30 µl/min. Data was double reference subtracted and analyzed using BIAevaluation 3.2 software to calculate kinetic constants. The tested surrogate Fcabs bound to mouse LAG-3 with single digit nanomolar affinity as set out in Table 2.

TABLE 2

Binding affinity ($K_D$) of surrogate LAG-3 specific Fcabs to mouse LAG-3

| Surrogate Fcabs specific for mouse LAG-3 | Affinity $K_D$ (nM) |
| --- | --- |
| FS18-7-108-29 | 1.5 |
| FS18-7-108-35 | 2.1 |

1.4.3 Binding Affinity of Fcabs to Human LAG-3 Expressed on Cells as Determined by Flow Cytometry Production of Cell Lines Over-Expressing LAG-3

Lentiviral transduction methodology was used to generate DO11.10 cells (National Jewish Health) over-expressing human, cynomolgus or mouse LAG-3 using the Lenti-X HTX Packaging System (Clontech, Cat. No 631249). Lenti-X expression vector (pLVX) (Clontech, Cat. No 631253), containing the mouse LAG-3 cDNA (SEQ ID NO: 96), human LAG-3 cDNA (SEQ ID NO: 95) or cynomolgus LAG-3 cDNA (SEQ ID NO: 97), was co-transfected with a Lenti-X HTX Packaging Mix into the Lenti-X 293T Cell Line (Clontech, Cat. No 632180) to generate virus. The DO11.10 cell line was transduced using the lentiviral vectors produced with the Lenti-X HTX Packaging System.

The affinity of the anti-human LAG-3 Fcabs in mock mAb² format to cells expressing human LAG-3 (DO11.10 cell line transfected with human LAG-3) was measured using flow cytometry. mAb² and control mAb dilutions (2× final concentration) were prepared in triplicate in 1×DPBS (Gibco, 14190-094). DO11.10:LAG-3 cell suspensions were prepared in PBS+2% BSA (Sigma, A7906) and seeded at $4 \times 10^{-6}$ cell/ml with 50 µl/well in V-bottomed 96-well plates (Costar, 3897). 50 µl of the mAb² or control mAb (anti human LAG-3 mAb, 25F7) dilutions were added to the wells containing cells (final volume 100 µl) and incubated at 4° C. for 1 hour. The plates were washed and 100 µl/well of secondary antibody (anti-human Fc-488 antibody, Jackson ImmunoResearch, 109-546-098) diluted 1:1000 in PBS+2% BSA was then added and incubated for 30 mins at 4° C. in the dark. The plates were washed and resuspended in 100 µl of PBS containing DAPI (Biotium, 40043) at 1 mg/ml. The plates were read using Canto II flow cytometer (BD Bioscience). Dead cells were excluded and the fluorescence in the FITC channel (488 nm/530/30) was measured. The data was fitted using log (agonist) vs response in GraphPad Prism Software. All tested Fcabs in mock mAb² format and the benchmark anti-human LAG-3 mAb, 25F7, bound human LAG-3 with similar affinity ($EC_{50}$), in the range of 1.2-2.1 nM as set out in Table 3.

TABLE 3

Binding affinity of anti-human LAG-3 Fcabs in mock mAb² format to DO11.10 cells expressing human LAG-3 as determined by flow cytometry

| Anti-human LAG-3 Fcab in mock mAb² format and benchmark anti-human LAG-3 mAb, 25F7 | $EC_{50}$ (nM) |
| --- | --- |
| FS18-7-9 | 1.2 |
| FS18-7-32 | 1.6 |
| FS18-7-33 | 1.5 |
| FS18-7-36 | 1.5 |
| FS18-7-62 | 2.1 |
| FS18-7-65 | 1.6 |
| FS18-7-78 | 1.7 |
| 25F7 | 2.1 |

1.4.4 Binding Affinity of Fcabs to Cynomolgus LAG-3 Expressed on Cells as Determined by Flow Cytometry The affinity of the anti-human LAG-3 Fcabs in mock mAb² format to cells expressing cynomolgus LAG-3 (DO11.10 cell line transfected with cynomolgus LAG-3) was measured using flow cytometry. mAb² and control mAb dilutions (2× final concentration) were prepared in triplicate in 1×DPBS (Gibco, 14190-094). DO11.10:LAG-3 cell suspensions were prepared in PBS+2% BSA (Sigma, A7906) and seeded at $4 \times 10^{-6}$ cell/ml with 50 µl/well in V-bottomed 96-well plates (Costar, 3897). 50 µl of the mAb² or control mAb (anti human LAG-3 mAb, 25F7) dilutions were added to the wells containing cells (final volume 100 µl) and incubated at 4° C. for 1 hour. The plates were washed and 100 µl/well of secondary antibody (anti-human Fc-488 antibody, Jackson ImmunoResearch, 109-546-098) diluted 1:1000 in PBS+2% BSA was then added and incubated for 30 mins at 4° C. in the dark. The plates were washed and resuspended in 100 µl of PBS containing DAPI (Biotium, 40043) at 1 mg/ml. The plates were read using Canto II flow cytometer (BD Bioscience). The dead cells were excluded and the fluorescence in the FITC channel (488 nm/530/30) was measured. The data was fit using log (agonist) vs response in GraphPad Prism Software. The tested Fcabs in mock mAb$^2$ format bound to cynomolgus LAG-3 with 0.5-0.6 nM affinity indicating that toxicology studies in cynomolgus monkeys would be expected to be predictive of effects seen in humans (see Table 4). The benchmark anti-human LAG-3 mAb, 25F7, binds cynomolgus LAG-3 with a 15-fold poorer affinity ($EC_{50}$) (Table 4).

TABLE 4

Binding affinity of anti-LAG-3 Fcabs to DO11.10 cells expressing cynomolgus LAG-3 by flow cytometry

| Anti-human LAG-3 Fcab in mock mAb$^2$ format and benchmark anti-human LAG-3 mAb, 25F7 | $EC_{50}$ (nM) |
|---|---|
| FS18-7-9 | 0.6 |
| FS18-7-62 | 0.5 |
| FS18-7-78 | 0.5 |
| 25F7 | 9.0 |

1.4.5 Binding Affinity of Surrogate Anti-Mouse LAG-3 Fcabs and Anti-Human LAG-3 Fcab to Mouse LAG-3 Expressed on Cells as Determined by Flow Cytometry Production of HEK Cells Over-Expressing mLAG-3

The mouse LAG-3 sequence (SEQ ID NO: 96) was subcloned into pcDNA5FRT vector (Life Technologies, V6010-20) using Kpnl (NEB, R0142) and Notl (NEB, R0146) restriction digestion. The vector was then transformed into Flp-In T-REx 293 HEK cell line (Life Technologies, R780-07) using Lipofectamine 2000 (Life Technologies, 11668-019). Transformed Flp-In T-REx 293 cells were grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) for 3-4 weeks until colonies of stably transformed cells were apparent. These colonies were amplified in the presence of 1 µg/ml Doxycyclin (Sigma, D9891) and tested for mouse LAG-3 expression using PE conjugated anti-mouse LAG-3 (clone C9B7W, BD Biosciences, 552380).

The affinity of the surrogate anti-mouse LAG-3 Fcabs (containing the truncated hinge) to cell-expressed mouse LAG-3 was determined using flow cytometry. HEK cells expressing mLAG-3 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014) and seeded in V-bottom 96-well plates (Costar, 3897) at 2×10$^5$ cells/well. The plates were centrifuged at 1500 rpm for 3 min at 4° C. to pellet the cells. A dilution series of the Fcabs (or control mAb) were incubated with the cells in a 100 µl volume for 1 h at 4° C. The plates were washed and secondary antibody (Anti-human Fc-488, Jackson ImmunoResearch, 109-546-098 for Fcabs or Anti-Rat IgG (H+L), Alexa Fluor 488 Conjugate, ThermoFisher, A-11006 for C9B7W) was diluted 1:1000 in PBS and 100 µl was added to the cells for 30 min at 4° C. (plates were kept in the dark). The plates were then washed and the cells resuspended in 100 µl PBS containing 1 µg/ml DAPI (Biotium, 40043). The plates were read using Canto II flow cytometer (BD Bioscience). Dead cells were excluded and the fluorescence in the FITC channel (488 nm530/30) was measured. The data was fit using log (agonist) vs response in GraphPad Prism Software. The tested Fcabs bound to mouse LAG-3 with similar affinity (see Table 5). The benchmark LAG-3 mAb, C9B7W (2B Scientific, BE0174-50 MG), binds mouse LAG-3 with 17-fold poorer affinity ($EC_{50}$) than the Fcabs (Table 5).

TABLE 5

Binding affinity of surrogate anti-mouse LAG-3 Fcabs to HEK cells expressing mouse LAG-3 by flow cytometry

| Anti-mouse LAG-3 Fcabs and benchmark anti-mouse LAG-3 mAb, C9B7W | $EC_{50}$ (nM) |
|---|---|
| FS18-7-108-29 | 4.5 |
| FS18-7-108-35 | 4.5 |
| C9B7W | 79 |

The affinity of the anti-human LAG-3 Fcab FS18-7-9 in mock mAb$^2$ format to cell-expressed mouse LAG-3 was determined using flow cytometry. HEK cells expressing mLAG-3 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014). Cells were collected by centrifuged at 1500 rpm for 3 min at 4° C. to pellet the cells and then resuspended in 1×DPBS then seeded in V-bottom 96-well plates (Costar, 3897) at 1.2×10$^5$ cells/well in 30 µl. A 1:1 volume of a dilution series of the mAb$^2$ (or control mAb) was added and incubated with the cells for 1 h at 4° C. The plates were washed and secondary antibody (Anti-human Fc-488, Jackson ImmunoResearch, 109-546-098) was diluted 1:1000 in PBS and 60 µl was added to the cells for 30 min at 4° C. (plates were kept in the dark). The plates were then washed and the cells resuspended in 60 µl PBS containing 1 µg/ml DAPI (Biotium, 40043). The plates were read using Canto II flow cytometer (BD Bioscience). Dead cells were excluded and the fluorescence in the FITC channel (488 nm/530/30) was measured. The data was fitted using log (agonist) vs response in GraphPad Prism Software.

The anti-human LAG-3 Fcab FS18-7-9 in mock mAb$^2$ format bound to mouse LAG-3 with an $EC_{50}$ of 19 nM compared to an $EC_{50}$ of 2.6 nM for the surrogate anti-mouse LAG-3 Fcab FS18-7-9-108 (Table 6). The human mAb, 25F7 does not show any detectable binding to mouse LAG-3, indicating that the human LAG-3 Fcab, FS18-7-9, has a different binding epitope on LAG-3 than that of 25F7.

TABLE 6

Binding affinity of human anti-LAG-3 Fcab FS18-7-9 to HEK cells expressing mouse LAG-3 by flow cytometry

| Anti-human LAG-3 Fcab, anti-mouse LAG-3 Fcab and benchmark anti-human LAG-3 mAb, 25F7 | $EC_{50}$ (nM) |
|---|---|
| FS18-7-108-29 | 2.6 |
| FS18-7-9 | 19 |
| 25F7 | No binding |

1.5 Binding Affinity of Fcabs to Fc Receptors

The introduction of the LALA mutation in the CH2 domain of human IgG1 is known to reduce Fcγ receptor binding (Bruhns, P., et al. (2009) and Xu, D, et al. (2000)). BIAcore was used to confirm that the LALA mutation had reduced the binding affinity of the Fcabs (in mock mAb$^2$ format) to Fcγ receptors. The human FcγR binding assay was performed on a Biacore T200 instrument (GE Healthcare) using the Fcabs in the mock mAb$^2$ format. Human FcγRs (R&D Systems. 1257-FC, 1330-CD, 1875-CD, 4325-FC) were immobilized using amine coupling (amine coupling kit, GE Healthcare, BR-1000-50) onto a Series S CM5 chip (GE Healthcare, BR-1005-30) to a surface density of 370 RU for FcγRI, 264 RU for FcγRIII (high affinity human FcγRs) and 500 RU for FcγRIIa and FcγRIIb (low affinity human FcγRs). For each immobilized chip a flow cell was left blank for background subtraction. FcγR were immobilized using a concentration of 5 μg/ml in sodium acetate pH5 (ForteBio, 18-1069) and injected at a flow rate of 10 μl/min in 15 second cycles until the required immobilization level was reached.

For the high affinity FcγRI and FcγRIII, 200 μg/ml of mAbs or mock mAb$^2$ were flowed across the chip for 3 min at a flow rate of 30 μl/min and the dissociation was followed for 5 min. Running buffer was HBS-P (0.01 M HEPES pH 7.4, 0.15 M NaCl, 0.005% v/v Surfactant P20, GE Healthcare, BR-1003-68). For the low affinity FcγRIIa and FcvRIIb the concentration of mock mAb$^2$ was increased to 500 μg/ml.

The positive control was a wild type IgG1 isotype mAb, which was compared to controls LALA IgG1 mAb and monoclonal IgG2 and IgG4 isotype mAbs to irrelevant targets. The flow cells were regenerated by injecting 10 mM sodium hydroxide (VWR, 28244.262) at a flow rate of 100 μl/min for 30 seconds. The data analysis was performed with BiaEvaluation software version 3.2 RC1 by double referencing against the blank flow cell (without immobilized FcγR) and subtracting a buffer cycle from test mAb$^2$. The results are shown in Table 7.

TABLE 7

Binding response of anti-human LAG-3 Fcabs in mock mAb$^2$ format (comprising LALA mutation as detailed above) to human Fcγ receptors by SPR

| mAb/mock mAb$^2$ | Binding response at end of association (RU) | | | |
|---|---|---|---|---|
| | FcγRI | FcγRIII | FcγRIIa | FcγRIIb |
| FS18-7-9 | 1.4 | 6.6 | −9.8 | −8.5 |
| FS18-7-62 | −0.9 | 0.7 | −10 | −8.5 |
| FS18-7-78 | −0.3 | 4.0 | −10.7 | −9.2 |
| mock mAb LALA | 2 | 8.0 | −12.7 | −9.6 |
| IgG2 | 0 | 1.9 | 9.7 | 7.4 |
| IgG4 | 9 | 3.1 | 4.3 | 15.1 |
| mock mAb IgG1 | 26 | 44 | 13 | 17.7 |

All mock mAb$^2$ tested (all comprising the LALA mutation as set out above) showed significantly reduced binding to the tested Fcγ receptors compared to the control antibody (mock mAb IgG1) without the LALA mutation, indicating that the LALA mutation has reduced Fcγ receptor binding by these mock mAb$^2$ and therefore is expected to reduce ADCC activity of the mAb$^2$.

1.6 Blocking of MHC Class II Binding to LAG-3

The ability of the Fcabs (containing the truncated hinge; SEQ ID NO: 58) to block the interaction between recombinant human or mouse LAG-3 Fc and human MHC Class II was studied by measuring binding of LAG-3 Fc to A375 cells, a melanoma cell line that expresses human MHC Class II. A375 (ATCC, CRL-1619) cells grown in DMEM (Life Technologies, 61965-026) containing 10% FBS (Life Technologies, 10270-106) were detached from cell culture flasks using cell dissociation buffer (Life Technologies, 13151-014) and seeded in V-bottom 96-well plates (Costar, 3897) at 2×10$^5$ cells/well. The plates were centrifuged at 1500 rpm for 3 min at 4° C. to pellet the cells. The relevant concentrations of Fcab or control mAb were incubated with 1 μg/ml LAG-3 Fc (human LAG-3-Fc R&D Systems, 2319-L3-050 or mouse LAG-3 Fc R&D Systems, 3328-L3-050) in 100 μl DMEM containing 10% FBS for 1 h at 4° C. LAG-3/Fcab mix was added to the A375 cells and incubated for 1 h at 4° C. Cells were washed. Secondary antibody (Alexa Fluor 488 conjugated goat anti-human Fc F(ab')$_2$, Jackson Immunoresearch, 109-546-098 or Goat anti-mouse IgG (H+L) 488 conjugate, Life Technologies, A-1101) was diluted 1:1000 in PBS and 100 μl was added to the cells for 30 min at 4° C. (plates were kept in the dark). Cells were washed once in PBS and resuspended in 100 μl PBS+1 μg/ml DAPI (Biotium, 40043). The plates were read on a BD FACSCanto II cytometer (BD Biosciences) and the data analysed using FlowJo software.

Both anti-mouse LAG-3 Fcabs were able to inhibit the interaction of human MHC class II with mouse LAG-3, whereas the control anti-mouse LAG-3 mAb (C9B7W, 2B Scientific, BE0174-50MG) was not (see Table 8).

TABLE 8

Surrogate anti-mouse LAG-3 Fcabs inhibit binding of mouse LAG-3 to MHC class II

| Surrogate anti-mouse LAG-3 Fcabs and control anti-mouse LAG-3 mAb C9B7W | IC$_{50}$ (nM) |
|---|---|
| FS18-7-108-29 | 0.6 |
| FS18-7-108-35 | 0.7 |
| C9B7W | No blocking |

The anti-human LAG-3 Fcabs tested were also able to inhibit the interaction of human MHC class II with human LAG-3 with a similar potency as the control anti-human LAG-3 mAb (25F7).

TABLE 9

Anti-human LAG-3 Fcabs inhibit binding of human LAG-3 to MHC class II

| Anti-human LAG-3 Fcabs and control anti-human LAG-3 mAb 25F7 | IC$_{50}$ (nM) |
|---|---|
| FS18-7-108-33 | 2.6 |
| FS18-7-108-78 | 2.4 |
| 25F7 | 3.6 |

Example 2 Activity of Fcab Molecules in DO11.10 T Cell Activation Assays 2.1 Activity of Lead Fcabs in a Human LAG-3 DO11.10 T Cell Activation Assay The panel of lead Fcabs (with a truncated hinge; SEG ID NO: 58) containing the LALA mutation were tested in a DO11.10 based T cell activation assay.

Cell Culture Media and Peptide:
  DO11.10 Cell culture medium: DMEM (Gibco, 61965-026) 10% FBS (Gibco, 10270-106), 1 mM Sodium Pyruvate (Gibco, 11360-070), 1 μg/ml puromycin (Gibco, A11138-03)
  Experimental medium: complete DO11.10 culture medium without puromycin.
  A20 Cell culture media: RPMI (Gibco, 61870-010) 10% FBS (Gibco, 10270-106), 1 mM Sodium Pyruvate (Gibco, 11360-070)
  OVA peptide (MW=1773.9 Da): H-ISQAVHAA-HAEINEAGR-OH (Pepscan)
Cells:
  DO11.10 hLAG-3: DO11.10 T cells transduced with a lentiviral vector to overexpress human LAG-3 (as above)
  A20: BALB/c B cell lymphoma line expressing MHC Class II (ATCC, TIB-208)

Dilutions of Fcabs or benchmark mAb were prepared in 200 μl experimental media. Fcabs were mixed 1:1 (170 μl+170 μl) with $4\times10^5$/ml DO11.10 LAG-3 cells in experimental media and incubated at 37° C., 5% $CO_2$ for 1 hour. $2\times10^5$ A20 cells/ml experimental media were incubated with 1 μM OVA peptide for 30 min. 360 μl of the A20 cells+OVA mixture were added to 360 μl of the DO11.10 LAG-3 cell/Fcab mix. The cells were then mixed in a deep well plate and cultured in a 96-round bottom plate with 200 μl of the mix/well. The assay was run in triplicate. Cell were incubated at 37° C. 5% $CO_2$ for 24 hours. Supernatants were collected and assayed with mouse IL-2 ELISA kit (eBioscience, 88-7024-88 or R&D systems, SM2000) following the manufacturer's instructions. Plates were read at 450 nm using the plate reader with the Gen5 Software, BioTek. Absorbance values of 570 nm were subtracted from those of 450 nm (Correction). The standard curve for calculation of cytokine concentration was based on four parameter logistic curve fit (Gen5 Software, BioTek). The concentration of mIL-2 was plotted vs the log concentration of Fcab or benchmark mAb and the resulting curves were fitted using the log (agonist) vs response equation in GraphPad Prism. The results are shown in Table 10.

TABLE 10

$EC_{50}$ values of anti-human LAG-3 Fcabs in DO11.10 T cell activation assay

| Anti-human LAG-3 Fcabs (with LALA mutation) and benchmark anti-human LAG-3 mab, 25F7 | $EC_{50}$ (nM) |
|---|---|
| FS18-7-95 | 0.8 |
| FS18-7-78 | 1.0 |
| FS18-7-62 | 1.1 |
| FS18-7-33 | 1.1 |
| FS18-7-65 | 1.1 |
| FS18-7-9 | 1.2 |
| FS18-7-36 | 1.3 |
| FS18-7-58 | 1.3 |
| FS18-7-88 | 1.3 |
| FS18-7-32 | 1.7 |
| 25F7 | 2.2 |

The human lead Fcabs show significant activity in the T cell activation assay with potencies in the range of 1-2 nM. The Fcabs have slightly improved potency than the benchmark anti human-LAG-3 mAb 25F7. Improved potency in the T cell activation assay is expected to be predictive of improved efficacy in human patients through enhanced inhibition of LAG-3.

2.2 Activity of Surrogate Anti-Mouse LAG-3 Fcabs in a Mouse LAG-3 DO11.10 T Cell Activation Assay The surrogate anti-mouse LAG-3 Fcabs (with a truncated hinge; SEQ ID NO: 58) containing the LALA mutation were tested in a DO11.10 based T cell activation assay.
Cell Culture Media and Peptide:
  DO11.10 Cell culture medium: DMEM (Gibco, 61965-026) 10% FBS (Gibco, 10270-106), 1 mM Sodium Pyruvate (Gibco, 11360-070), 1 μg/ml puromycin (Gibco, A11138-03)
  Experimental medium: complete DO11.10 culture medium without puromycin.
  A20 Cell culture media: RPM (Gibco, 61870-010) 10% FBS (Gibco, 10270-106), 1 mM Sodium Pyruvate (Gibco, 11360-070)
  OVA peptide (MW=1773.9 Da): H-ISQAVHAA-HAEINEAGR-OH (Pepscan)
Cells:
  DO11.10 mLAG-3: DO11.10 T cells transduced with a lentiviral vector to overexpress mouse LAG-3 (as above)
  A20: BALB/c B cell lymphoma line expressing MHC Class II (ATCC, TIB-208)

Dilutions of Fcabs or benchmark mAb were prepared in 200 μl experimental media. Fcabs were mixed 1:1 (170 μl+170 μl) with $4\times10^5$ ml DO11.10 LAG-3 cells in experimental media and incubated at 37° C., 5% CO2 for 1 hour. $2\times10^5$ A20 cells/ml experimental media were incubated with 1 μM OVA peptide for 30 min. 360 μl of the A20 cells+OVA mixture were added to 360 μl of the DO11.10 LAG-3 cell/Fcab mix. The cells were then mixed in a deep well plate and cultured in a 96-round bottom plate with 200 μl of the mix/well. The screen was assayed in triplicates. Cell were incubated at 37° C., 5% $CO_2$ for 24 hours. Supernatants were collected and assayed with mouse 1L-2 ELISA kit (eBioscience, 88-7024-88 or R&D systems, SM2000) following the manufacturer's instructions. Plates were read at 450 nm using the plate reader with the Gen5 Software, BioTek. Absorbance values of 570 nm were subtracted from those of 450 nm (Correction). The standard curve for calculation of cytokine concentration was based on four parameter logistic curve fit (Gen5 Software, BioTek). The concentration of mIL-2 was plotted vs the log concentration of Fcab or benchmark mAb and the resulting curves were fitted using the log (agonist) vs response equation in GraphPad Prism. The results are shown in Table 11 and FIG. 2.

TABLE 11

$EC_{50}$ values and maximal IL-2 release of surrogate anti-LAG-3 Fcabs in DO11.10 T cell activation assay

| Surrogate Fcabs specific for mouse LAG-3 (with LALA mutation) and benchmark anti-mouse LAG-3 mAb, C9B7W | $EC_{50}$ (nM) | Maximal IL-2 release (pg/ml) |
|---|---|---|
| FS18-7-108-29 | 1.9 | 205 |
| FS18-7-108-35 | 1.8 | 176 |
| C9B7W | 5.1 | 48 |

The mouse surrogate anti-mouse LAG-3 Fcabs showed significant activity in the T cell activation assay with potencies in the range of 2 nM. The surrogate anti-mouse LAG-3 Fcabs had higher potency than the benchmark anti mouse-LAG-3 antibody as is evident from the improved $EC_{50}$ and the 4-fold higher maximal activation of IL-2 release.

Improved potency and maximal activation of these Fcabs compared to the benchmark is expected to result in improved activity in murine efficacy studies compared to the benchmark through improved inhibition of LAG-3.

2.3 Activity of FS18-7-9 in Mock mAb² Format in a Cynomolgus LAG-3 DO11.10 T cell Activation Assay One of the lead Fcabs, FS18-7-9 was tested in a cynomolgus LAG-3 DO11.10 based T cell activation assay in the mock mAb² format comprising the LALA mutation described above.

Cell Culture Media and Peptide:
DO11.10 Cell culture medium: DMEM (Gibco, 61965-026) 10% FBS (Gibco, 10270-106), 1 mM Sodium Pyruvate (Gibco, 11360-070), 1 µg/ml puromycin (Gibco, A11138-03)
Experimental medium: complete DO11.10 culture medium without puromycin.
A20 Cell culture media: DMEM (Gibco, 61965-026) 10% FBS (Gibco, 10270-106), 1 mM Sodium Pyruvate (Gibco, 11360-070), 1 µg/ml puromycin (Gibco, A11138-03)
OVA peptide (MW=1773.9 Da): H-ISQAVHAA-HAEINEAGR-OH (Pepscan)

Figure 3:
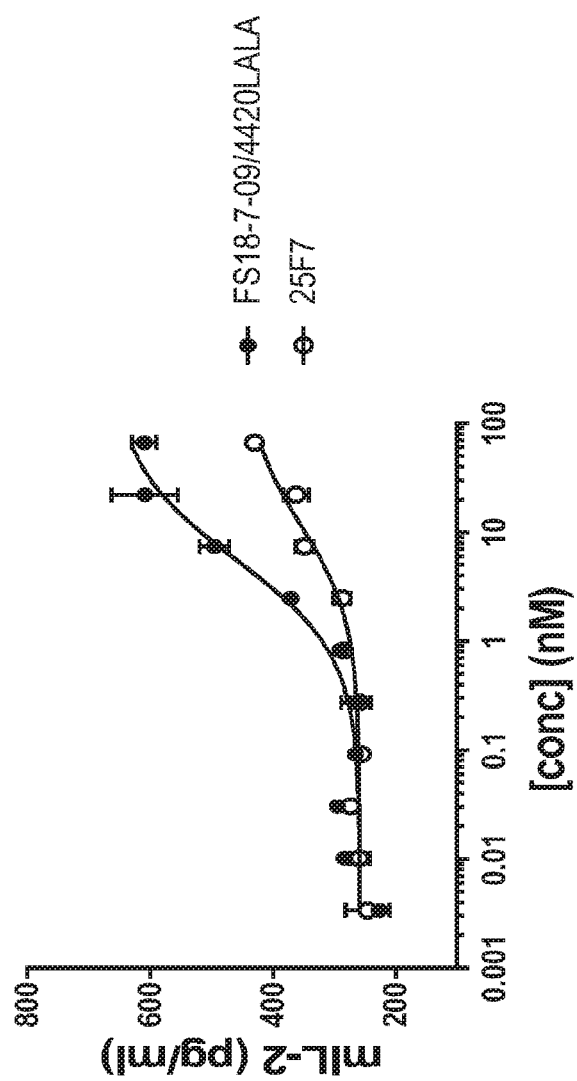
FIG. 3 shows that the anti-LAG-3 Fcab, FS18-7-9, in mock mAb$^2$ format inhibits cynomolgus monkey LAG-3 leading to release of mIL-2 in a DO11.10 T-cell activation assay. The benchmark anti-LAG-3 mAb, 25F7, showed an increase in mIL-2 release, however the maximal release was approximately two thirds that of the Fcab in mock mAb$^2$ format.

Cells:
DO11.10 cynoLAG-3: DO11.10 T cells transduced with a lentiviral vector to overexpress cynomolgus LAG-3 (as above)
LK 35.2 PLVX: B cell hybridoma transduced with an empty lentiviral (pLVX) vector;

Dilutions of the FS18-7-9 Fcab in mock mAb² format (FS18-7-9/4420LALA) or benchmark mAb were prepared in experimental media. DO11.10 cells ($0.3 \times 10^6$ cells/ml) were mixed at a 1:1 ratio with antibodies at 3× final concentration. Antibodies and cells were incubated at 37° C., 5% $CO_2$ for 1 hour. LK 35.2 cells were incubated at $3 \times 10^5$ cells/ml experimental media with the OVA peptide at 1.5 µM for 30 min. 70 µl of LK 35.2 cells+OVA were added to 140 µl of the DO11.10/antibody. Cells were incubated at 37° C., 5% $CO_2$ for 24 hours. Supernatants were collected and assayed with mouse IL-2 ELISA kit (eBioscience, 88-7024-88 or R&D systems, SM2000) following the manufacturer's instructions. Plates were read at 450 nm using the plate reader with the Gen5 Software, BioTek. Absorbance values of 570 nm were subtracted from those of 450 nm (Correction). The standard curve for calculation of cytokine concentration was based on four parameter logistic curve fit (Gen5 Software, BioTek). The concentration of mIL-2 was plotted vs the log concentration of Fcab in mock mAb² format or benchmark mAb and the resulting curves were fitted using the log (agonist) vs response equation in Graph-Pad Prism. The results are shown in Table 12 and FIG. 3.

TABLE 12

$EC_{50}$ values and maximal IL-2 release of anti-LAG-3 Fcabs in cynomolgus DO11.10 T cell activation assay

| FS18-7-9 Fcab in mock mAb² format or benchmark anti-human LAG-3 mAb | $EC_{50}$ (nM) | Maximal IL-2 release (pg/ml) |
|---|---|---|
| FS18-7-9/4420LALA | 5.6 | 608 |
| 25F7 | 11.4 | 430 |

The FS18-7-9 Fcab in mock mAb² format showed significant activity in the T cell activation assay with a potency of 5.6 nM. Specifically, the FS18-7-9 Fcab in mock mAb² format had higher potency against cynomolgus LAG-3 than the benchmark anti human-LAG-3 antibody, as is evident from the improved $EC_{50}$ and the higher maximal activation of IL-2 release. Compared with the benchmark, the $EC_{50}$ and maximal activation of the Fcab in mock mAb² format on human and cyno-LAG-3, as determined using a T cell activation assay, is more similar (the benchmark has lower $EC_{50}$ on cyno-LAG-3 than the Fcab but has a similar $EC_{50}$ on human-LAG-3 in T-cell activation assay). It is therefore expected that the results of studies in cynomolgus monkeys using the Fcabs, e.g. in mock mAb² format, will be more predictive of the response in human patients. For example, if higher potency resulted in higher toxicity, it is expected that this would be seen when conducting testing in a cynomolgus monkey model, whereas a molecule with lower potency in cynomolgus monkeys than humans would not see this ahead of commencing trials in human patients.

Example 3—In Vivo Anti-Tumour Efficacy of Fcabs in mAb² Format

3.1 Preparation of mAb² for In Vivo Testing in Mice mAb² molecules comprising the surrogate anti-mouse LAG-3 Fcab, FS18-7-108-29, were prepared. The mAb² molecules comprised a Fab region specific for murine CD73 (TY11.8), murine TIM-3 (RMT3-23), murine CSF-1R (AFS98) or murine CLTA-4 (9D9), and were tested for in vivo anti-tumour activity using a MC38 syngeneic mouse tumour growth model. The Fab sequences were sourced as follows:

Rat Anti-Mouse TIM-3 Antibody
Clone name—RMT3-23
Reference—Nakayama, M et. al, 2009
Mouse Anti-Mouse CTLA-4 Antibody
Clone name—9D9
Reference—Patent application US 2011/0044953 A1
Rat Anti-Mouse CSF-1R Antibody
Clone name—AFS98
Reference—Sudo T, et al 1995
Rat Anti-Mouse CD73 Antibody
Clone name—TY 11.8
Reference—Yamashita, Y, et al 1998

In order to produce the control antibodies for the in vivo experiments, the variable heavy regions from each of the above sources were joined to the human IgG1 (G1m17) constant regions, the variable light regions from each of the above sources was joined to the human constant region (Km1) via human kappa J-region 1 (except 9D9 where mouse kappa J-region 1 was used). The mAb² for the in vivo studies were generated by substituting the CH3 domains of the reformatted constructs described above with FS18-7-108-29.

3.2 Activity of mAb² in a MC38 Syngeneic Tumour Model

The MC38 syngeneic tumour model was used in this experiment as MC38 tumours are known to be highly immunogenic resulting in increased LAG-3 expression on immune cells in the tumour environment and tumour periphery.

C57BL/6 female mice (Charles River) aged 8-10 weeks and weighing 20-25 g each were rested for one week prior to the study start. All animals were micro-chipped and given a unique identifier. Each cohort had 10 mice. The MC38 colon carcinoma cell line (S. Rosenberg, NIH) was initially expanded, stored, and then pre-screened by IDEXX Bicresearch for pathogens using the IMPACT I protocol and shown to be pathogen free. MC38 cells were thawed from −150° C. storage and added to 20 ml DMEM (Gibco, 61965-026) with 10% FCS (Gibco, 10270-106) in a T175 tissue culture flask. Each animal received 2×10$^6$ cells injected subcutaneously in the left flank. 7-8 days following tumour cell inoculation, mice which did not have tumours at this point were removed from the study. All of the mAb$^2$ molecules and the control antibody were analysed within 24 hours prior to injection by SEC-HPLC profiling and checked for impurities.

The mAb$^2$ molecules and the control antibody were injected into mice at a final concentration of 10 mg/kg in PBS. Each mouse received mAb$^2$ or control antibody mixture by intraperitoneal (IP) injection on days 8, 11, and 14 following tumour inoculation. Accurate measurements of tumours were taken, any drug dosing due on the day in question was performed, and the mice subjected to close observation for the remainder of the trial. Tumour volume measurements were taken with callipers to determine the longest axis and the shortest axis of the tumour. The following formula was used to calculate the tumour volume:

$$L \times (S^2)/2$$

Where L=longest axis; S=shortest axis

The trial was halted at day 25 when tumour burden was considered close to restrictions.

Figure 4:
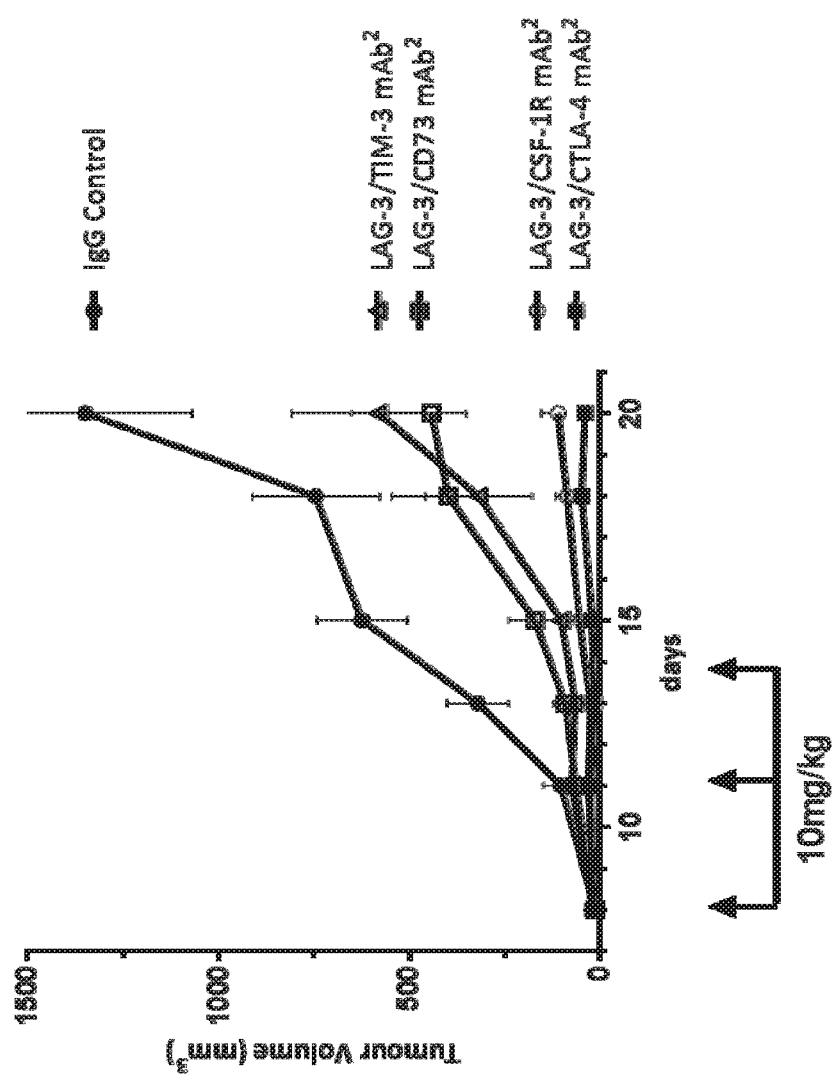
FIG. 4 shows that mAb$^2$ molecules comprising the surrogate anti-mouse LAG-3 Fcab, FS18-7-108-29 and a Fab region specific for murine TIM-3, CD73, CSF-1R or CTLA-4 are able to significantly reduce tumour growth in a MC38 syngeneic tumour model compared to IgG control treated mice.

As shown in FIG. 4, all of the tested mAb$^2$ molecules showed significant tumour growth inhibition compared to mice treated with the IgG control. The study shows that in mice with a fully functioning immune system, inhibition of LAG-3 in combination with inhibition with TIM-3, CSF-1R, CTLA-4 or CD73 leads to a reduction in tumour growth, presumably through increased activity of the immune system. Syngeneic mouse models are accepted as appropriate murine systems for testing the anti-tumour effect of inhibiting therapeutic targets and have been used extensively to validate development of human therapeutics. It has been shown that CTLA-4 inhibition results in increased T cell priming in the lymph nodes. Once primed, the T cell migrates to the tumour microenvironment where blockade of the PD-1/PD-L1 axis enhances activation of the primed T cell, resulting in synergistic anti-tumour effects of the anti-CTLA-4 and anti-PD-1/PD-L1 combination. This is reflected in the increased efficacy of the PD-1 and CTLA-4 combination in the clinic. It is hypothesised that the profound tumour inhibition caused by LAG-3/CTLA-4 mAb$^2$ in the syngeneic MC38 tumour model is through a similar synergy; inhibition of CTLA-4 increasing T cell priming and inhibition of LAG-3 increasing T cell activation at the tumour site. The more modest effect of dual inhibition of LAG-3 and TIM-3 may be ascribed to LAG-3 and TIM-3 suppressing exhausted T cells with a similar mode of action. These are secondary signals that are expressed after PD-1 is on T cells. With PD-1 inhibition still retained, inhibiting TIM-3 and LAG-3 can only achieve mild results.

Macrophages are critical in maintaining an immunosuppressive tumour environment. Targeting of CSF-1R results in a decrease in tumour associated macrophages due to inhibition of macrophage differentiation and elimination of survival signals. It is hypothesised that the profound tumour inhibition caused by LAG-3/CSF-1R mAb$^2$ in the syngeneic MC38 tumour model is through synergy resulting from a release of the macrophage-induced immmunosupression in the tumour environment that allows LAG-3 antibodies to increase T cell activation at the tumour site. Combinations of CSF-1R and checkpoint inhibitors are already being evaluated in the clinic, which will help inform the viability of combining CSF-1R with LAG-3 inhibition. Blockade of CD73 also results in inhibition of macrophages however the intermediate tumour suppressive effect of CD73/LAG-3 mAb$^2$ suggests that anti-CD73 may be a less potent macrophage inhibitor. Since the surrogate anti-mouse LAG-3 Fcabs are so closely related in sequence to those of the anti-human Fcabs (and were derived from the same parental anti-human LAG-3 Fcab), they both bind to a very similar epitope of LAG-3 (mouse and human, respectively) despite the difference in homology between human and murine LAG-3. Consequently, it is expected that the results observed in mice following their treatment with mAb$^2$ comprising the surrogate anti-mouse LAG-3 Fcab are predictive of treatment of human patients with mAb$^2$ comprising the anti-human LAG-3 Fcab.

Example 5: Effect of Fcab Treatment on T Cell LAG-3 Expression

The effect of the LAG-3/mock mAb$^2$, FS18-7-108-29/4420 containing the LALA mutation (SEQ ID NOs: 132 and 85), referred to as FS18-29/4420, the benchmark PD-L1 mAb S1 containing the LALA mutation (SEQ ID NOs: 122 and 119) and a combination of FS18-29/4420 and S1, on TIL LAG-3 expression was tested.

On the day of implant, cultured MC38.OVA cells were harvested during log phase growth (Confluency~75%) and resuspended in PBS at a concentration of 1×10$^7$ cells/mL. Tumours were initiated by first anesthetizing each animal with isoflurane, then subcutaneously implanting 1×10$^6$ MC38.OVA cells (0.1 mL suspension) into the left flank of each test animal. Eleven days after tumour cell implantation animals were randomised, using a deterministic randomisation method, into five groups with individual tumour volumes of 32 to 62.5 mm$^3$. Animals were dosed at 10 mg/kg antibody or mAb$^2$ on day 12, 14 and 16 after tumour inoculation, and tumours collected from three animals/group at days 19 and 23 after tumour inoculation. GentleMACS™ Dissociator was used to dissociate the tumour with cells subsequently sieved through a 70 μm cell strainer to obtain a single cell suspension. 1×10$^6$ cells/well on a 96-well plate were resuspended in FACS buffer with 1:3000 viability stain and Fc block (anti-CD16/32 antibody). Cells for FACS analysis were stained using a Master Mix that included labelled antibodies against CD43, CD8a, CD4, FoxP3, and LAG-3. For the FoxP3 intracellular staining cells were fixed and permeabilized prior to staining with the FoxP3 antibody. Samples were run on the Canto II flow cytometer with a compensation matrix and a minimum of 500,000 events counted.

Figure 5:
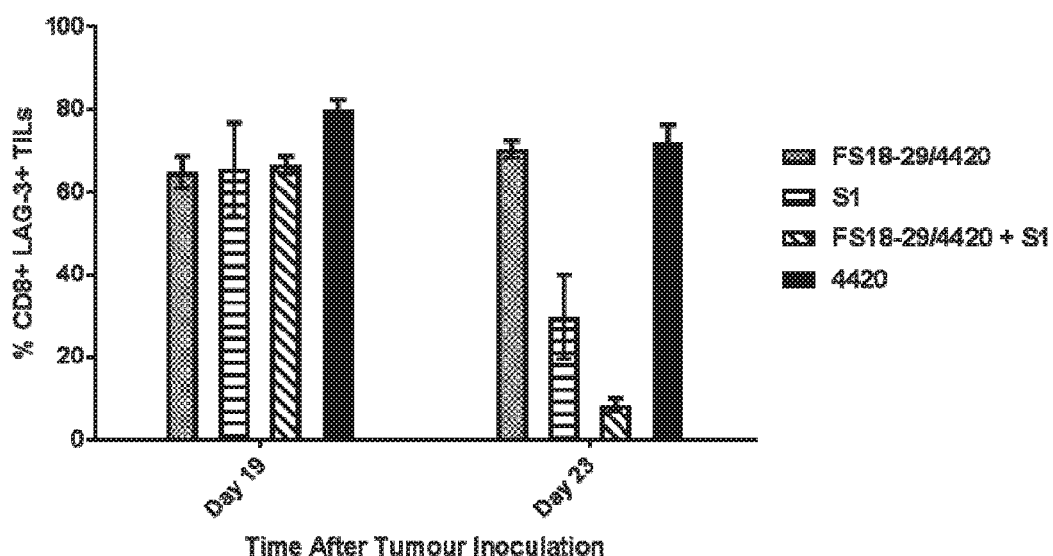
FIG. 5 shows the effect of antibody treatment on T cell LAG-3 expression. LAG-3 expression on CD8 (A), CD4 (B) and FoxP3 (C) tumour infiltrating lymphocytes (TILs) treated with FS18-29/4420, S1, FS18-29/4420 and S1, or control antibody 4420 is shown at day 19 and 23 after tumour inoculation, corresponding to days 3 and 7 after the last mAb$^2$/antibody dosing, respectively. LAG-3 expression was decreased after treatment with a combination of FS18-29/4420 and S1 on day 23, while FS18-29/4420 or S1 administered individually resulted in little to no decrease in LAG-3 expression.
Figure 5:
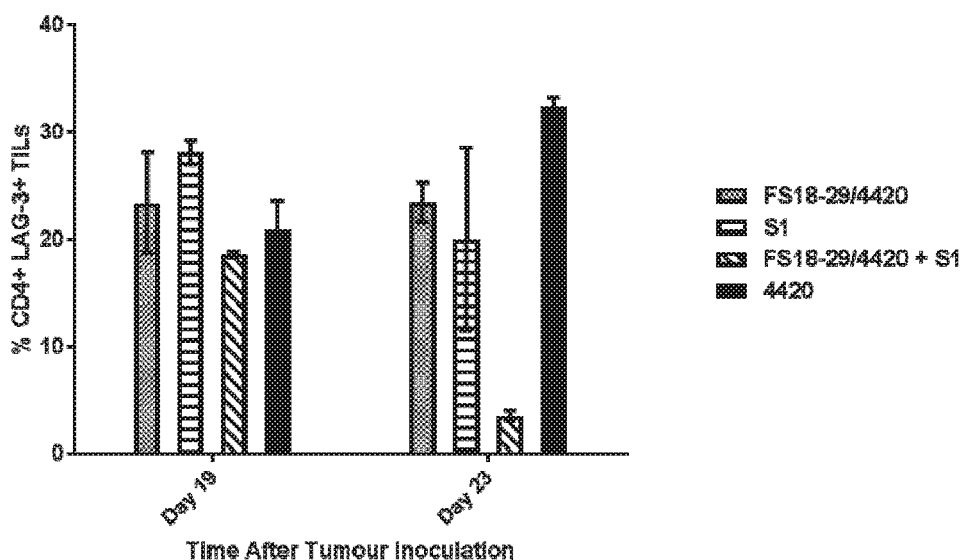
Figure 5:
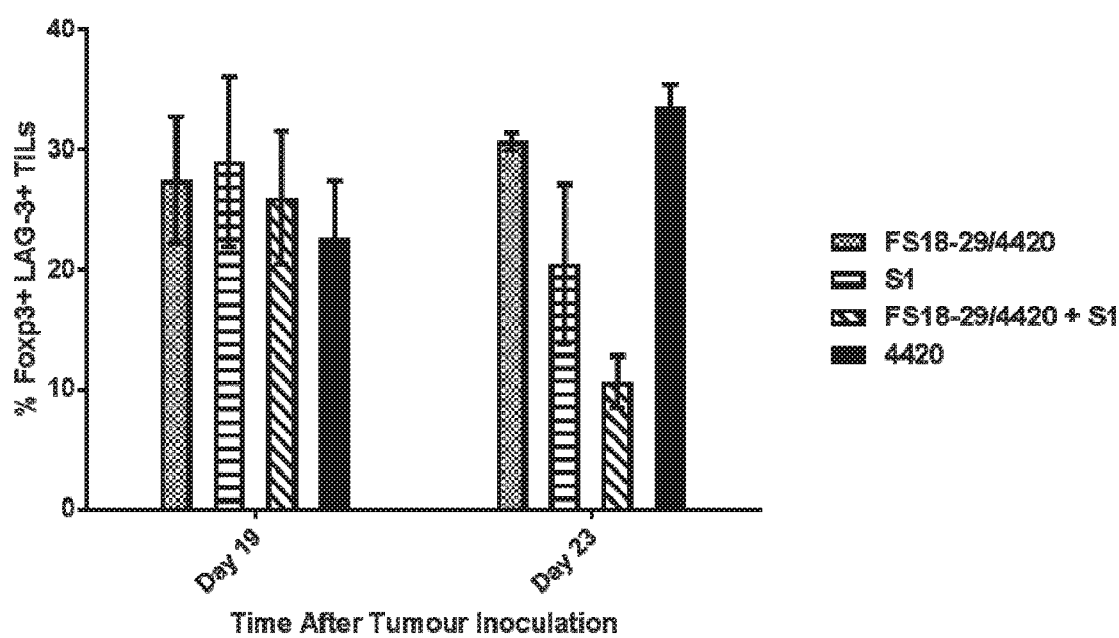

In this experiment, TILs were examined for LAG-3 expression after the third dose of antibody/mock mAb$^2$ had been administered, when a separation in the growth of the tumour between control and non-control treatments is seen but before there is a large difference between tumour sizes which might skew results. At this time point, LAG-3 expression on TILs was found to be markedly decreased in animals treated with the combination of FS18-29/4420 and S1. Specifically, as shown in FIG. 5, LAG-3 expression on CD8, CD4 and FoxP3 tumour infiltrating lymphocytes (TILs) was decreased after treatment with a combination of FS18-29/

4420 and S1 by day 23, while treatment with FS18-29/4420 or S1 administered individually had little to no effect on LAG-3 expression on TILs.

These results show that dual inhibition of LAG-3 and PD-L1 is required for a decrease in LAG-3 expression by TILs, as this phenomenon was not seen in animals treated with single agents against LAG-3 or PD-L1. Without wishing to be bound by theory, it is thought that dual anti-LAG-3 and anti-PD-L1 treatment leads to a decrease in LAG-3 expression on TILS, thereby reducing the inhibitory effect of LAG-3 and allowing the TILs to overcome exhaustion. Once the TILs become activated, it is expected that they will be able to recognise neo-antigens expressed by the tumour and mount a response against it, and thereby reduce the tumour burden.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~208 kb), which was created on Dec. 11, 2018, which is incorporated by reference herein.

| Sequence Listing |
|---|
| Amino acid sequences of Fcab FS18-7-9 loop regions<br>FS18-7-9 AB loop-WDEPWGED (SEQ ID NO: 1) |
| FS18-7-9 CD loop-SNGQPENNY (SEQ ID NO: 2) |
| FS18-7-9 EF loop-PYDRWVWPDE (SEQ ID NO: 3) |
| Nucleotide sequence of Fcab FS18-7-9 CH3 domain (SEQ ID NO: 4)<br>GGCCAGCCTCGAGAACCACAGGTGTACACCCTGCCCCCATCCTGGGATGAGCCGTGGGGTGAA<br>GACGTCAGCCTGACCTGCCIGGTCAAAGGCTTCTATCCCAGCGACATCGCCGTGGAGTGGGAG<br>AGCAATGGGCAGCCGGAGAACAACTACAAGACCACGCCTCCCGTGCTGGACTCCGACGGCTCC<br>TTCTTCCTCTACAGCAAGCTCACCGTGCCGTATGATAGGTGGGTTTGGCCGGATGAGTTCTCATG<br>CTCCGTGATGCATGAGGCTCTGCACAACCACTACACACAGAAGAGCCTCTCCCTGTCTCCGGGT |
| CHO codon optimised nucleotide sequence of Fcab FS18-7-9 CH3<br>domain (SEQ ID NO: 136)<br>GGCCAGCCCCGGGAACCCCAGGTGTACACACTGCCTCCATCCTGGGATGAGCCCTGGGGCGA<br>GGATGTGTCTCTGACCTGTCTCGTGAAAGGCTTCTACCCCTCCGATATCGCCGTGGAATGGGAG<br>AGCAACGGCCAGCCCGAGAACAACTACAAGACCACCCCCCCTGTGCTGGACTCCGACGGCTCA<br>TTCTTCCTGTACAGCAAGCTGACAGTGCCCTACGACAGATGGGTGTGGCCCGACGAGTTCTCCT<br>GCTCCGTGATGCACGAGGCCCTGCACAACCACTACACCCAGAAGTCCCTGTCCCTGAGCCCCG<br>GC |
| Amino acid sequence of Fcab FS18-7-9 CH3 domain (SEQ ID NO: 5)<br>GQPREPQVYTLPPSWDEPWGEDVSLTCLVKGFYPSDIAVEWESNGQPENNYKTTPPVLDSDGSFFL<br>YSKLTVPYDRWVWPDEFSCSVMHEALHNHYTQKSLSLSPG |
| Amino acid seauence of Fcab FS18-7-9 CH2 and CH3 domains, comprising<br>LALA mutation (underlined) (SEQ ID NO: 6)<br>APEAAGGPSVFLFPPKPKDTLMISRTPEVTCVVVDVSHEDPEVKFNWYVDGVEVHNAKTKPREEQY<br>NSTYMNSVLTVLHQDWLNGKEYKCKVSNKALPAPIEKTISKAKGQPREPQVYTLPPSWDEPWGED<br>VSLTCLVKGFYPSDIAVEWESNGQPENNYKTTPPVLDSDGSFFLYSKLTVPYDRWVWPDEFSCSVM<br>HEALHNHYTQKSLSLSPG |
| Amino acid seauence of Fcab FS18-7-9 CH2 and CH3 domains without LALA<br>mutation (SEQ ID NO: 7)<br>APELLGGPSVFLFPPKPKDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQVYTLPPSWDEPWGEDVS<br>LTCLVKGFYPSDIAVEWESNGQPENNYKTTPPVLDSDGSFFLYSKLTVPYDRWVWPDEFSCSVMHE<br>ALHNHYTQKSLSLSPG |
| Amino acid sequences of Fcab FS18-7-32 loop regions<br>FS18-7-32 AB loop-WDEPWGED (SEQ ID NO: 1) |
| FS18-7-32 CD loop-SNGQPENNY (SEQ ID NO: 8) |
| FS18-7-32 EF loop-PYDRWVWPDE (SEQ ID NO: 3) |
| Nucleotide sequence of Fcab FS18-7-32 CH3 domain (SEQ ID NO: 9)<br>GGCCAGCCTCGAGAACCACAGGTGTACACCCTGCCCCCATCCTGGGATGAGCCGTGGGGTGAA<br>GACGTCAGCCTGACCTGCCTGGTCAAAGGCTTCTATCCCAGCGAAATCGCCGTGGAGTGGGAG<br>AGCAATGGGCAGCCGGAGAACAACTACAAGACCACGCCTCCCGTGCTGGACTCCGACGGCTCC<br>TTCTTCCTCTACAGCAAGCTCACCGTGCCGTATGATAGGTGGGTTTGGCCGGATGAGTTCTCATG<br>CTCCGTGATGCATGAGGCTCTGCACAACCACTACACACAGAAGAGCCTCTCCCTGTCTCCGGGT |
| Amino acid seauence of Fcab FS18-7-32 CH3 domain (SEQ ID NO: 10)<br>GQPREPQVYTLPPSWDEPWGEDVSLTCLVKGFYPSEIAVEWESNGQPENNYKTTPPVLDSDGSFFL<br>YSKLTVPYDRWVWPDEFSCSVMHEALHNHYTQKSLKSPG |

Sequence Listing

Amino acid sequence of Fcab FS18-7-32 CH2 and CH3 domains, comprising LALA, mutation (underlined) (SEC ID NO: 11)
APE<u>AA</u>GGPSVFLFPPKPKDTLMISRTPEVTCVVVDVSHEDPEVKFNWWDGVEVHNAKTKPREEQY
NSTYRWSVLTVLHQDWLNGKEYKCKVSNKALPAPIEKTISKAKGQPREPQVYTLPPSWDEPWGED
VSLTCLVKGFYPSEIAVEWESNGQPENNYKTTPPVLDSDGSFFLYSKLTVPYDRWVWPDEFSCSVM
HEALHNHYTQKSLSLSPG Amino acid seauence of Fcab FS18-7-32 CH2 and CH3 domains without LALA mutation (SEQ ID NO: 12)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSEIAVEWESNGQPENNYKTTPPVLDSDGSFFLYSKLTVPYDRWVWPDEFSCSVMHE
ALHNHYTQKSLSLSPG Amino acid sequences of Fcab FS18-7-33 loop regions
FS18-7-33 AB loop-WDEPWGED (SEQ ID NO: 1)

FS18-7-33 CD loop-SNGQPEDNY (SEQ ID NO: 13)

FS18-7-33 EF loop-PYDRONWPDE (SEQ ID NO: 3)

Nucleotide sequence of Fcab FS18-7-33 CH3 domain (SEQ ID NO: 14)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGCAGCCGGAGGACAACTACAAGACCACGCCTCCCGTGCTGGACTCCGACGGCTCC
TTCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-33 CH3 domain (SEQ ID NO: 15)
GQPREPQVYTLPPSWDEPWGEDVSLTCLVKGFYPSDIAVEWESNGQPEDNYKTTPPVLDSDGSFFL
YSKLTVPYDRWVWPDEFSCSVMHEALHNHYTQKSLSLSPG Amino acid sequence of Fcab FS18-7-33 CH2 and CH3 domains, comprising LALA mutation (underlined) (SEQ ID NO: 16)
APE<u>AA</u>GGPSVFLFPPKPKDTLMISRTPEVTCVVVDVSHEDPEVKFNWYVDGVEVHNAKTKPREEQY
NSTYRWSVLTVLHQDWLNGKEYKCKVSNKALPAPIEKTISKAKGQPREPQVYTLPPSWDEPWGED
VSLTCLVKGFYPSDIAVEWESNGQPEDNYKTTPPVLDSDGSFFLYSKLTVPYDRWVWPDEFSCSVM
HEALHNHYTQKSLSLSPG Amino acid sequence of Fcab FS18-7-33 CH2 and CH3 domains without LALA mutation SEQ ID NO: 17)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGQPEDNYKTTPPVLDSDGSFFLYSKLTVPYDRWVWPDEFSCSVMHE
ALHNHYTQKSLSLSPG Amino acid sequences of Fcab FS18-7-36 loop regions
FS18-7-36 AB loop-WDEPWGED (SEQ ID NO: 1)

FS18-7-36 CD loop-SNGQPENNY (SEQ ID NO: 18)

FS18-7-36 EF loop-PYDRVWVPDE (SEQ ID NO: 3)

Nucleotide sequence of Fcab FS18-7-36 CH3 domain (SEQ ID NO: 19)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGCTCC
TACTTCCTCTACAGCAAGCTCACCGTGCCGTATGATAGGTGGGTTTGGCCGGATGAGTTCTCAT
GCTCCGTGATGCATGAGGCTCTGCACAACCACTACACACAGAAGAGCCTCTCCCTGTCTCCGGG
T Amino acid sequence of Fcab FS18-7-36 CH3 domain (SEQ ID NO: 20)
GQPREPQVYTLPPSWDEPWGEDVSLTCLVKGFYPSDIAVEWESNGQPENNYKTTPPVLDSDGSYFL
YSKLTVPYDRWVWPDEFSCSVMHEALHNHYTQKSLSLSPG Amino acid seauence of CH2 + CH3 of Fcab FS18-7-36 CH2 and CH3 domains, comprising LALA mutation (underlined) (SEQ ID NO: 21)
APE<u>AA</u>GGPSVFLFPPKPKDTLMISRTPEVTCVVVDVSHEDPEVKFNWYVDGVEVHNAKTKPREEQY
NSTYRWSVLTVLHQDWLNGKEYKCKVSNKALPAPIEKTISKAKGQPREPQVYTLPPSWDEPWGED
VSLTCLVKGFYPSDIAVEWESNGQPENNYKTTPPVLDSDGSYFLYSKLTVPYDRWVWPDEFSCSVM
HEALHNHYTQKSLSLSPG

Sequence Listing

Amino acid sequence of Fcab FS18-7-36 CH2 and CH3 domains without LALA mutation (SEQ ID NO: 22)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGQPENNYKTTPPVLDSDGSYFLYSKLTVPYDRWVWPDEFSCSVMHE
ALHNHYTQKSLSLSPG Amino acid sequences of Fcab FS18-7-58 loop regions
FS18-7-58 AB loop-WDEPWGED (SEQ ID NO: 1)

FS18-7-58 CD loop-SNGYPEIEF (SEQ ID NO: 23)

FS18-7-58 EF loop-PYDRWVWPDE (SEQ ID NO: 3)

Nucleotide sequence of Fcab FS18-7-58 CH3 domain (SEQ ID NO: 24)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATCCAGAAATCGAATTCAAGACCACGCCTCCCGTGCTGGACTCCGACGGCTCCT
TCTTCCTCTACAGCAAGCTCACCGTGCCTTATGATAGGTGGGTTTGGCCGGATGAGTTCTCATGC
TCCGTGATGCATGAGGCTCTGCACAACCACTACACACAGAAGAGCCTCTCCCTGTCTCCGGGT Amino acid sequence of Fcab FS18-7-58 CH3 domain (SEQ ID NO: 25)
GQPREPQVYTLPPSWDEPWGEDVSLTCLVKGFYPSDIAVEWESNGYPEIEFKTTPPVLDSDGSFFLY
SKLTVPYDRWVWPDEFSCSVMHEALHNHYTQKSLSLSPG Amino acid sequence of Fcab FS18-7-58 CH2 and CH3 domains, comprising LALA mutation (underlined) (SEQ ID NO: 26)
APEAAGGPSVFLFPPKPKDTLMISRTPEVTCVVVDVSHEDPEVKFNWYVDGVEVHNAKTKPREEQY
NSTYRWSVLTVLHQDWLNGKEYKCKVSNKALPAPIEKTISKAKGQPREPQVYTLPPSWDEPWGED
VSLTCLVKGFYPSDIAVEWESNGYPEIEFKTTPPVLDSDGSFFLYSKLTVPYDRWVWFDEFSCSVMH
EALHNHYTQKSLSLSPG Amino acid sequence of Fcab FS18-7-58 CH2 and CH3 domains without LALA mutation (SEQ ID NO: 27)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGYPEIEFKTTPPVLDSDGSFFLYSKLTVPYDRWVWPDEFSCSVMHEA
LHNHYTQKSLSLSPG Amino acid sequences of Fcab FS18-7-62 loop regions
FS18-7-62 AB loop-WDEPWGED (SEQ ID NO: 1)

FS18-7-62 CD loop-SNGIPEWNY (SEQ ID NO: 28)

FS18-7-62 EF loop-PYDRWVWPDE (SEQ ID NO: 3)

Nucleotide sequence of Fcab FS18-7-62 CH3 domain (SEQ ID NO: 29)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGATCCCAGAATGGAACTATAAGACCACGCCTCCCGTGCTGGACTCCGACGGCTCCT
TCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-62 CH3 domain (SEQ ID NO: 30)
GQPREPQVYTLPPSWDEPWGEDVSLTCLVKGFYPSDIAVEWESNGIPEWNYKTTPPVLDSDGSFFL
YSKLTVPYDRAWVWPDEFSCSVMHEALHNHYTQKSLSLSPG Amino acid sequence of Fcab FS18-7-62 CH2 and CH3 domains, comprising LALA mutation (underlined) (SEQ ID NO: 31)
APEAAGGPSVFLFPPKPKDTLMISRTPEVTCVVVDVSHEDPEVKFNWYVDGVEVHNAKTKPREEQY
NSTYRWSVLTVLHQDWLNGKEYKCKVSNKALPAPIEKTISKAKGQPREPQVYTLPPSWDEPWGED
VSLTCLVKGFYPSDIAVEWESNGIPEWNYKTTPPVLDSDGSFFLYSKLTVPYDRWVWPDEFSCSVMH
EALHNHYTQKSLSLSPG Amino acid sequence of Fcab FS18-7-62 CH2 and CH3 domains without LALA mutation (SEQ ID NO: 32)
APELLGGPSVFLFPPKPKDTLMISRTPEVTCVVVDVSHEDPEVKFNWYVDGVEVHNAKTKPREEQYN
STYRWSVLTVLHQDWLNGKEYKCKVSNKALPAPIEKTISKAKGQPREPQVYTLPPSWDEPWGEDVS
LTCLVKGFYPSDIAVEWESNGIPEWNYKTTPPVLDSDGSFFLYSKLTVPYDRWVWPDEFSCSVMHEA
LHNHYTQKSLSLSPG Amino acid sequences of Fcab FS18-7-65 loop regions
FS18-7-65 AB loop-WDEPWGED (SEQ ID NO: 1)

FS18-7-65 CD loop-SNGYAEYNY (SEQ ID NO: 33)

FS18-7-65 EF loop-PYDRWVWPDE (SEQ ID NO: 3)

Nucleotide sequence of Fcab FS18-7-65 CH3 domain (SEQ ID NO: 34)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATGCAGAATATAACTATAAGACCACGCCTCCCGTGCTGGACTCCGACGGCTCCT
TCTTCCTCTACAGCAAGCTCACCGTGCCGATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-65 CH3 domain (SEQ ID NO: 35)
GQPREPQVYTLPPSWDEPWGEDVSLTCLVKGFYPSDIAVEWESNGYAEYNYKTTPPVLDSDGSFFL
YSKLTVPYDRWVWPDEFSCSVMHEALHNHYTQKSLSLSPG Amino acid sequence of Fcab FS18-7-65 CH2 and CH3 domains, comprising
LALA mutation (underlined) (SEQ ID NO: 36)
APEAAGGPSVFLFPPKPKDTLMISRTPEVTCVVVDVSHEDPEVKFNWYVDGVEVHNAKTKPREEQY
NSTYRWSVLTVLHQDWLNGKEYKCKVSNKALPAPIEKTISKAKGQPREPQVYTLPPSWDEPWGED
VSLTCLVKGFYPSDIAVEWESNGYAEYNYKTTPPVLDSCGSFFLYSKLTVPYDRWVWPDEFSCSVM
HEALHNHYTQKSLSLSPG Amino acid sequence of Fcab FS18-7-65 CH2 and CH3 domains without LALA
mutation (SEQ ID NO: 37)
APELLGGPSVFLFPPKPKDTLMISRTPEVTCVVVDVSHEDPEVKFNWYVDGVEVHNAKTKPREEQYN
STYRWSVLTVLHQDWLNGKEYKCKVSNKALPAPIEKTISKAKGQPREPQVYTLPPSWDEPWGEDVS
LTCLVKGFYPSDIAVEWESNGYAEYNYKTTPPVLDSDGSFFLYSKLTVPYDRWVWPDEFSCSVMHE
ALHNHYTQKSLSLSPG Amino acid sequences of Fcab FS18-7-78 loop regions
FS18-7-78 AB loop-WDEPWGED (SEQ ID NO: 1)

FS18-7-78 CD loop-SNGYKEENY (SEQ ID NO: 38)

FS18-7-78 EF loop-PYDRWVWPDE (SEQ ID NO: 3)

Nucleotide sequence of Fcab FS18-7-78 CH3 domain (SEQ ID NO: 39)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATAAAGAAGAAAACTATAAGACCACGCCTCCCGTGCTGGACTCCGACGGCTCCT
TCTTCCTCTACAGCAAGCTCACCGTGCCGATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-78 CH3 domain (SEQ ID NO: 40)
GQPREPQVYTLPPSWDEPWGEDVSLTCLVKGFYPSDIAVEWESNGYKEENYKTTPPVLDSDGSFFL
YSKLTVPYDRWVWPDEFSCSVMHEALHNHYTQKSLSLSPG Amino acid sequence of Fcab FS18-7-78 CH2 and CH3 domains, comprising
LALA mutation (underlined) (SEQ ID NO: 41)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGYKEENYKTTPPVLDSDGSFFLYSKLTVPYDRWVWPDEFSCSVM
HEALHNHYTQKSLSLSPG Amino acid sequence of Fcab FS18-7-78 CH2 and CH3 domains without LALA
mutation (SEQ ID NO: 42)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGYKEENYKTTPPVLDSDGSFFLYSKLTVPYDRWVWPDEFSCSVMHE
ALHNHYTQKSLSLSPG Amino acid sequences of Fcab FS18-7-88 loop regions
FS18-7-88 AB loop-WDEPWGED (SEQ ID NO: 1)

FS18-7-88 CD loop-SNGVPELNV (SEQ ID NO: 43)

FS18-7-88 EF loop-PYDRWVWPDE (SEQ ID NO: 3)

Nucleotide sequence of Fcab FS18-7-88 CH3 domain (SEQ ID NO: 44)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGGTTCCAGAACTGAACGTTAAGACCACGCCTCCCGTGCTGGACTCCGACGGCTCCT
TCTTCCTCTACAGCAAGCTCACCGTGCCGATGATAGGTGGGTTTGGCCGGATGAGTTCTCATG
CTCCGTGATGCATGAGGCTCTGCACAACCACTACACACAGAAGAGCCTCTCCCTGTCTCCGGGT Amine acid sequence of Fcab F818-7-88 CH3 domain (SEQ ID NO: 45)
GQPREPQVYTLPPSWDEPWGEDVSLTCLVKGFYPSDIAVEWESNGVPELNVKTTPPVLDSDGSFFL
YSKLTVPYDRWVWPDEFSCSVMHEALHNHYTQKSLSLSPG

Sequence Listing

Amino acid sequence of Fcab FS18-7-88 CH2 and CH3 domains, comprising LALA mutation (underlined) (SEQ ID NO: 46)
APE<u>AA</u>GGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGVPELNVKTTPPVLDSDGSFFLYSKLTVPYDRWVWFDEFSCSVMH
EALHNHYTQKSLSLSPG Amino acid sequence of Fcab FS18-7-88 CH2 and CH3 domains without LALA mutation (SEQ ID NO: 47)
APELLGGPSVFLFPPKPKDTLMISRTPEVTCVVVDVSHEDPEVKFNWYVDGVEVHNAKTKPREEQYN
STYMNSVLTVLHQDWLNGKEYKCKVSNKALPAPIEKTISKAKGQPREPQVYTLPPSWDEPWGEDVS
LTCLVKGFYPSDIAVEWESNGVPELNVKTTPPVLDSDGSFFLYSKLTVPYDRWVWFDEFSCSVMHEA
LHNHYTQKSLSLSPG Amino acid sequences of Fcab FS18-7-95 loop regions
FS18-7-95 AB loop-WDEPWGED (SEQ ID NO: 1)

FS18-7-95 CD loop-SNGYQEDNY (SEQ ID NO: 48)

FS18-7-95 EF loop-PYDRWVWPDE (SEQ ID NO: 3)

Nucleotide sequence of Fcab FS18-7-95 CH3 domain (SEQ ID NO: 49)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATCAGGAAGATAACTATAAGACCACGCCTCCCGTGCTGGACTCCGACGGCTCCT
TCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-95 CH3 domain (SEQ ID NO: 50)
GQPREPQVYTLPPSWDEPWGEDVSLTCLVKGFYPSDIAVEWESNGYQEDNYKTTPPVLDSDGSFFL
YSKLIWYDRWVWPDEFSCSVMHEALHNHYTQKSLSLSPG Amino acid sequence of Fcab FS18-7-95 CH2 and CH3 domains, comprising LALA mutation (underlined) (SEQ ID NO: 51)
APE<u>A</u>AGGPSVFLFPFKPKDTLMISRTPEVTCVVVDVSHEDPEVKFNWYVDGVEVHNAKTKPREEQY
NSTYMNSVLTVLHQDWLNGKEYKCKVSNKALPAPIEKTISKAKGQPREPQVYTLPPSWDEPWGED
VSLTCLVKGFYPSDIAVEWESNGYQEDNYKTTPPVLDSDGSFFLYSKLTVPYDRWVWPDEFSCSVM
HEALHNHYTQKSLSLSPG Amino acid sequence of Fcab FS18-7-95 CH2 and CH3 domainswithout LALA mutation (SEQ ID NO: 52)
APELLGGPSVFLFPPKPKDTLMISRTPEVTCVVVDVSHEDPEVKFNWYVDGVEVHNAKTKPREEQYN
STYMNSVLTVLHQDWLNGKEYKCKVSNKALPAPIEKTISKAKGQPREPQVYTLPPSWDEPWGEDVS
LTCLVKGFYPSDIAVEWESNGYQEDNYKTTPPVLDSDGSFFLYSKLTVPYDRWVWPDEFSCSVMHE
ALHNHYTQKSLSLSPG Amino acid sequence of the wild-type human IgG1 CH2 domain (SEG ID NO: 53)
APELLGGPSVFLFPPKPKOTLMISRTPEVTCVVVDVSHEDPEVKFNWYVDGVEVHNAKTKPREEQYN
STYRVVSVLTVLHQDWLNGKEYKCKVSNKALPAPIEKTISKAK Amino acid sequence of the human IgG1 CH2 domain comprising the "LALA mutation" (underlined) (SEQ ID NO: 54)
APE<u>AA</u>GGPSVFLFPPKPKDTLMISRTPEVTMANDVSHEDPEVKFNVMDGVEVHNAKTKPREEQY
NSTYRWSVLTVLHQDWLNGKEYKCKVSNKALPAPIEKTISKAK Amino acid sequence of "wild-type" Fcab CH2 and CH3 domains without LALA mutation (SEQ ID NO: 55).
APELLGGPSVFLFPPKPKDTLMISRTPEVTCVVVDVSHEDPEVKFNWYVDGVEVHNAKTKPREEQYN
STYRWSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEA
LHNHYTQKSLSLSPG Amino acid sequence of "wild-type" Fcab CH2 and CH3 domains, comprising LALA mutation (underlined) (SEQ ID NO: 56)
APE<u>AA</u>GGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFSCSVMH
EALHNHYTQKSLSLSPG Amino acid sequence of the human IgG1 hinue region (SEQ ID NO: 57)
EPKSCDKTHTCPPCP Amino acid secuence of the human IgG1 truncated hinge reuion (SEQ ID NO: 58)
TCPPCP -continued Sequence Listing Amino acid sequence anti-mouse LAG-3 Fcab FS18-7-108-29, comprising LALA mutation
(underlined) (SEC ID NO: 59)
The CH3 domain is shown in italics. The AB, CD and EF loops of the CH3 domain are
shown in bold and underlined.
TCPPCPAPE<u>AA</u>GGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK*GQPREPQVYTLPPS**WDEP*
*WGEDVSLTCLVKGFYPSDIVVEWESNGQPENNYKTTPPVLDSDGSFFLYSKLTVPFERWMWPDEFS*
*CSVMHEALHNHYTCKSLSLSPG*

Amino acid sequence of the anti-mouse LAG-3 Fcab FS18-7-108-29 without
LALA mutation (SEQ ID NO: 60)
The CH3 domain is shown in italics. The AB, CD and EF loops of the CH3 domain
are shown in bold and underlined.
TCPPCPAPELLGGPSVFLEPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK*GQPREPCNYTLPPS**WDEP*
*WGEDVSLTCLVKGFYPSDIVVEWESNGQPENNYKTTPPVLDSDGSFFLYSKLTVPFERWMWPDEFS*
*CSVMHEALHNHYTQKSLSLSPG*

Amino acid sequence of the anti-mouse LAG-3 Fcab FS18-7-108-35. comprising
LALA mutation (underlined) (SEQ ID NO: 61)
The CH3 domain is shown in italics. The AB, CD and EF loop regions are shown
in bold and underlined.
TCPPCPAPE<u>AA</u>GGPSVFLFPPKPKDTLMISRTPEVTCVVVDVSHEDPEVKFNWYVDGVEVHNAKTKP
REEQYNSTYRWSVLTVLHQDWLNGKEYKCKVSNKALPAPIEKTISKAK*GQPREPQVYTLPPS**WDEP*
*WGEDVSLTCLVKGFYPSDISVEWESNGQPENNYKTTPPVLDSDGSFFLYSKLTVPFERWMWPDEFS*
*CSVMHEALHNHYTQKSLSLSPG*

Amino acid sequence of the anti-mouse LAG-3 Fcab FS18-7-108-35 without LALA
mutation (SEQ ID NO: 62)
The GH3 domain is shown in italics. The AB, CD and EF loop regions are shown in
bold and underlined.
TCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK*GQPREPQVYTLPPS**WDEP*
*WGEDVSLTCLVKGEYPSDISVEWESNGQPENNYKTTPPVLDSDGSFFLYSKLTVPFERWMWPDEFS*
*CSVMHEALHNHYTQKSLSLSPG*

Amino acid sequence of the heavy chain of anti-human LAG-3/FITC mAb[2] FS18-7-9/4420
comprising LALA mutation (SEQ ID NO: 63)
Position of the CDRs are underlined, and the AB, CD, and EF loop sequences are in
bold and underlined. Position of LALA mutation is in bold.
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
KSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHWDWLNGKEYKCKVSNKALP
APIEKTISKAKGQPREPQVYTLPPSWDEPWGEDVSLTCLVKGFYPSDIAVEWESNGQPENNYKTTPP
VLDSDGSFFLYSKLTVPYDRWVWPDEFSCSVMHEALHNHYTQKSLSLSPG Amino acid sequence of the heavy chain of anti-human LAG-3/FITC mAb[2] FS18-7-9/4420
without LALA mutation (SEQ ID NO: 64)
Position of the CDRs are underlined, and the AB, CD, and EF loop sequences are
in bold and underlined.
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVD
VSHEDPEVKFNWYDGVEVHNAKTKPREEQYNSTYRWSVLTVLHQDWLNGKEYKCKVSNKALPAP
IEKTISKAKGQPREPQVYTLPPSWDEPWGEDVSLTCLVKGFYPSDIAVEWESNGQPENNYKTTPPVL
DSDGSFFLYSKLTVPYDRWVWPDEFSCSVMHEALHNHYTQKSLSLSPG Amino acid sequence of the heavy chain of anti-human LAG-3/FITC mAb[2]
FS18-7-32/4420 comprising LALA mutation (SEQ ID NO: 65)
Position of the CDRs are underlined, and the AB, CD, and EF loop sequences are
in bold and underlined, Position of LALA mutation is in bold,
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPECTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSEIAVEWESNGQPENNYKTTPP
VLDSDGSFFLYSKLTVPYDRWMPDEFSCSVMHEALHNHYTQKSLKSPG

| Sequence Listing |
|---|

Amino acid sequence of the heavy chain of anti-human LAG-3/FITC mAb² FS18-7-32/without LALA mutation (SEQ ID NO: 66)
Position of the CDRs are underlined, and the AB, CD, and EF loop sequences are in bold and underlined,
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPS<u>WDEPWGED</u>VSLTCLVKGFYPSEIAVEWE<u>SNGQPENNY</u>KTTPPVL
DSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-33/4420 comprising LALA mutation (SEQ ID NO: 67)
Position of the CDRs are underlined, and the AB, CD, and EF loop sequences are in bold and underlined. Position of LALA mutation is in bold.
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDEMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDIAVEWE<u>SNGQPEDNY</u>KTTPP
VLDSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-33/4420 without LALA mutation (SEQ ID NO: 68)
Position of the CDRs are underlined, and the AB, CD, and EF loop sequences are in bold and underlined.
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYMNSVLTVLHQDWLNGKEYKCKVSNKALPAP
IEKTISKAKGQPREPQVYTLPPS<u>WDEPWGED</u>VSLTCLVKGFYPSDIAVEWE<u>SNGQPEDNY</u>KTTPPVL
DSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-36/4420 comprising LALA mutation (SEQ ID NO: 69)
Position of the CDRs are underlined, and the AB, CD, and EF loop sequences are in bold and underlined. Position of LALA mutation is in bold.
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
VICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDIAVEWE<u>SNGQPENNY</u>KTTPP
VLDSDGSYFLYSKLTV<u>PYDRWVWPDE</u>FSCSVMHEALHNHYTQKSLSLSPG Amino acid sequence of the heavy chain of anti-human LAG-3/FITC mAb² FS18-7-36/4420 without LALA mutation (SEQ ID NO: 70)
Position of the CDRs are underlined, and the AB, CD, and EF loop sequences are bold and underlined.
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHICPPCPAPELLGGPSVFLFPPKPKDTLMISRIPEVTCVVD
VSHEDPEVKFNWYVDGVEVHNAKTKPREEQYNSTYRWSVLTVLHQDWLNGKEYKCKVSNKALPAP
IEKTISKAKGQPREPQVYTLPPS<u>WDEPWGED</u>VSLTCLVKGFYPSDIAVEWE<u>SNGQPENNY</u>KTTPPVL
DSDGSYFLYSKLTV<u>PYDRWVWPDE</u>FSCSVMHEALHNHYMKSLSLSPG Amino acid sequence of the heavy chain of anti-human LAG-3/FITC mAb² FS18-7-58/4420 comprising LALA mutation (SEQ ID NO: 71)
Position of the CDRs are underlined, and the AB. CD, and EF loop sequences are in bold and underlined. Position of LALA mutation is in bold.
EVKLDETGGGLVQPGRPMKLSCVAS<u>GFTFSDYW</u>MNWVRQSPEKGLEWVAQ<u>IRNKPYNYET</u>YYSDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDIAVEWE<u>SNGYPEIEF</u>KTTPPV
LDSDGSFFLYSKLTV<u>PYDRWVWPDE</u>FSCSVMHEALHNHYTQKSLSLSPG

Sequence Listing

Amino acid sequence of the heavy chain of anti-human LAG-3/FITC mAb² FS18-7-58/4420 without LALA mutation (SEQ ID NO: 72)
Position of the CDRs are underlined, and the AB, CD, and EF loop sequences are in bold and underlined.
EVKLDETGGGLVQPGRPMKLSCVASGFTFSDYWMNWVRQSPEKGLEVWAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDAVEWESNGYPEIEFKTTPPVLD
SDGSFFLYSKLTVPYDRWVWPDEFSCSVMHEALHNHYTQKSLSLSPG Amino acid sequence of the heavy chain of anti-human LAG-3/FITC mAb² FS18-7-62/4420 comprising LALA mutation (SEQ ID NO: 73)
Position of the CDRs are underlined, and the AB, CD, and EF loop sequences are in bold and underlined. Position of LALA mutation is in bold.
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGIPEWNYKTTPP
VLDSDGSFFLYSKLTVPYDRWVWPDEFSCSVMHEALHNHYTQKSLSLSPG Amino acid sequence of the heavy chain of anti-human LAG-3/FITC mAb² FS18-7-62/4420 without LALA mutation (SEQ ID NO: 74)
Position of the CDRs are underlined, and the AB, CD, and EF loop sequences are in bold and underlined.
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YIGNVNHKPSNKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRWSVLTVLHQDWLNGKEYKCKVSNKALPAP
IEKTISKAKGQPREPQVYTLPPSWDEPWGEDVSLTCLVKGFYPSDIAVEWESNGIPEWNYKTTPPVL
DSDGSFFLYSKLTVPYDRWVWPDEFSCSVMHEALHNHYTQKSLSLSPG Amino acid sequence of the heavy chain of anti-human LAG-3/FITC mAb² FS18-7-65/4420 comprising LALA mutation (SEQ ID NO: 75)
Position of the CDRs are underlined, and the AB, CD, and EF loop sequences are in bold and underlined. Position of LALA mutation is in bold.
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDRAGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGYAEYNYKTTPP
VLDSDGSFFLYSKLTVPYDRWVWPDEFSCSVMHEALHNHYTQKSLSLSPG Amino acid sequence of the heavy chain of anti-human LAG-3/FI10 mAb² FS18-7-65/4420 without LALA mutation (SEQ ID NO: 76)
Position of the CDRs are underlined, and the AB, CD, and EF loop sequences are in bold and underlined.
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDAVEWESNGYAEYNYKTTPPVL
DSDGSFFLYSKLTVPYDRWVWPDEFSCSVMHEALHNHYTQKSLSLSPG Amino acid sequence of the heavy chain of anti-human LAG-3/FITC mAb² FS18-7-78/4420 comprising LALA mutation (SEQ ID NO: 77)
Position of the CDRs are underlined, and the AB, CD, and EF loop sequences are in bold and underlined. Position of LALA mutation is in bold.
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGYKEENYKTTPP
VLDSDGSFFLYSKLTVPYDRWVWPDEFSCSVMHEALHNHYTQKSLSLSPG

Sequence Listing

Amino acid sequence of the heavy chain of anti-human LAG-3/FITC mAb² FS18-7-78/4420 without LALA mutation (SEQ ID NO: 78)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDRAGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPS<u>WDEPWGED</u>VSLTCLVKGFYPSDAVEWE<u>SNGYKEENY</u>KTTPPVL
DSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-88/4420 comprising LALA mutation (SEQ ID NO: 79)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDIAVEWE<u>SNWPELNV</u>KTTPP
VLDSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-88/4420 without LALA mutation (SEQ ID NO: 80)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRWSVLTVLHQDWLNGKEYKCKVSNKALPAP
IEKTISKAKGQPREPQVYTTPPS<u>WDEPWGED</u>VSLTCLVKGFYPSDIAVEWE<u>SNGVPELNV</u>KTTPPVL
DSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-95/4420 comprising LALA mutation (SEQ ID NO: 81)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDRAGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRWSVLTVLHQDWLNGKEYKCKVSNKALP
APIEKTISKAKGQPREPQVYTLPPS<u>WDEPWGED</u>VSLTCLVKGFYPSDIAVENE<u>SNGYQEDNY</u>KTTPP
VLDSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-95/4420 without LALA mutation (SEQ ID NO: 82)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPS<u>WDEPWGED</u>VSLTCLVKGFYPSDAVEWE<u>SNGYQEDNY</u>KTTPPVL
DSDGSFFLYSKLTV<u>PYDRWVWPDE</u>FSCSVMHEALHNHYTQKSLSLSPG Amino acid sequence of the heavy chain of anti-FITC mAb 4420 comprising LALA mutation (SEQ ID NO: 83)
Position of the CDRs are underlined. Position of LALA mutation is in bold.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>ANGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRWSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Amino acid sequence of the heavy chain of anti-FITC mAb 4420 without LALA mutation (SEQ ID NO: 84)
Position of the CDRs are underlined.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT YICNVNHKFSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of the anti-FITC mAb 4420 light chain (SEQ ID NO: 85)
Position of the CDRs are underlined.
DVVMTQTPLSLPVSLGDQASSCRSSQSLVHSNGNTYLRWYLQKPGQSPKVLIYKVSNRFSGVPDRF
SGSGSGTDFTLKISRVEAEDLGVYFCSQSTHVPWTFGGGTKLEIKRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC Amino acid sequence of the heavy chain of anti-mouse LAG-3/PD-L1 mAb$^2$ FS18-7-108-
29/S1 with LALA mutation (SEQ ID NO: 86)
Position of the CDRs are underlined, and the AB, CD, and EF loop sequences are in
bold and underlined. Position of LALA mutation is in bold.
EVQLVESGGGLVQPGGSLRLSCAASGFTFSDSWIHWVRQAPGKGLEWVAWISPYGGSTYYADSVK
GRFTISADTSKNTAYLQMNSLRAEDTANNYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRWSVLTVLHQDWLNGKEYKCKVSNKALP
APIEKTISKAKGQPREPQVYTLPPSWDEPWGEDVSLTCLVKGFYPSDIVVEWESNGQPENNYKTTPP
VLDSDGSFFLYSKLTVPFERWMWPDEFSCSVMHEALHNHYMKSLSLSPG Amino acid sequence of the heavy chain of anti-mouse LAG-3/PD-L1 mAb$^2$
FS18-7-108-29/S1 without LALA mutation (SEQ ID NO: 87)
Position of the CDRs are underlined, and the AB, CD, and EF loop sequences
are in bold and underlined.
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDILMISRTPEVTCVVVD
VSHEDPEVKFNWYVDGVEVHNAKTKPREEQYNSTYRWSVLTVLHQDWLNGKEYKCKVSNKALPAP
IEKTISKAKGQPREPQVYTTPPSWDEPWGEDVSLYCLVKGFYPSDIVVEWESNGQPENNYKTTPPVL
DSDGSFFLYSKLTVPFERWMWPDEFSCSVMHEALHNHYTQKSLSLSPG Amino acid sequence of the heavy chain of anti-mouse LAG-3/PD-L1 mAb$^2$
FS18-7-108-35/S1 with LALA mutation (SEQ ID NO: 88)
Position of the CDRs are underlined, and the AB, CD, and EF loop sequences are
in bold and underlined. Position of LALA mutation is in bold.
EVQLVESGGGLVQPGGSLRLSCAASGFTFSDSWIHVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRWSVLTVLHQDWLNGKEYKCKVSNKALP
APIEKTISKAKGQPREPQVYTLPPSWDEPWGEDVSLTCLVKGFYPSDISVEWESNGQPENNYKTTPP
VLDSDGSFFLYSKLTVPFERWMWPDEFSCSVMHEALHNHYTQKSLSLSPG Amino acid sequence of the heavy chain of anti-mouse LAG-3/PD-L1 mAb$^2$ FS18-7-08-
35/S1 without LALA mutation (SEQ ID NO: 89)
Position of the CDRs are underlined, and the AB, CD, and EF loop sequences are in
bold and underlined.
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDSVEWESNGQPENNYKTTPPVL
DSDGSFFLYSKLTVPFERWMWPDEFSCSVMHEALHNHYTQKSLSLSPG Amino acid sequence of the anti-mouse PD-L1 mAb S1 heavy chain with LALA mutation
(SEQ ID NO: 90)
Position of the CDRs are underlined. Position of LALA nutation is in bold.
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Amino acid sequence of the anti-mouse PD-L1 mAb S1 heavy chain without LALA mutation
(SEQ ID NO: 91)
Position of the CDRs are underlined.
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of the anti-mouse PD-L1 mAb S1 lighthain (SEQ ID NO: 92)
Position of the CDRs are underlined.
DIQMTQSPSSLSASVGDRVTITCRASQDVSTAVAWYQQKPGKAPKWYSASFLYSGVPSRFSGSGS
GTDFTLTISSLQPEDFATYYCQQYLFTPPTFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Amino acid sequence of the anti-human LAG-3 mAb 25F7 heavy chain (SEQ ID NO: 93)
Position of the CDRs are underlined.
QVQLQQWGAGLLKPSETLSLTCAVYGGSFSDYYWNWIRQPPGKGLEWIGEINHRGSTNSNPSLKSR
VTLSLDTSKNQFSLKLRSVTAADTAVYYCAFGYSDYEYNWFDPWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of the anti-human LAG-3 mAb 25F7 light chain (SEQ ID NO: 94)
Position of the CDRs are underlined.
EIVLTQSPATLSLSPGERATLSCRASQSISSYLAWYQQKPGQAPRLLIYDASNRATGIPARFSGSGSG
TDFTLTISSLEPEDFAVYYCQQRSNWPLTFGQGTNLEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSS
PVTKSFNRGEC Amino acid sequence of human LAG-3 (SEQ ID NO: 95)
MWEAQFLGLLFLQPLWVAPVKPLQPGAEVVWAQEGAPAQLPCSPTIPLQDLSLLRRAGVTWQHQ
PDSGPPAAAPGHPLAPGPHPAAPSSWGPRPRRYTVLSVGPGGLRSGRLPLQPRVQLDERGRQRGD
FSLWLRPARRADAGEYRAAVHLRDRALSCRLRLRLGQASMTASPPGSLRASDWVILNCSFSRPDRP
ASVHWFRNRGQGRVPVRESPHHHLAESFLFLPQVSPMDSGPWGCILTYRDGFNVSIMYNLTVLGLE
PPTPLTVYAGAGSRVGLPCRLPAGVGTRSFLTAKWTPPGGGPDLLVTGDNGDFTLRLEDVSQAQAG
TYTCHIHLQEQQLNATVTLAIITVTPKSFGSPGSLGKLLCEVTPVSGQERFVWSSLDTPSQRSFSGPW
LEAQEAQLLSQPWQCQLYQGERLLGAAVYFTELSSPGAQRSGRAPGALPAGHLLLFLILGVLSLLLLV
TGAFGFHLWRRQWRPRRFSALEQGIHPPQAQSKIEELEQEPEPEPEPEPEPEPEPEPEPEQL Amino acid sequence of mouse LAG-3 (SEQ ID NO: 96)
MREDLLLGFLLLGLLWEAPVVSSGPGKELPVVWAQEGAPVHLPCSLKSPNLDPNFLRRGGVIWQHQ
PDSGQPTPIPALDLHQGMPSPRQPAPGRYTVLSVAPGGLRSGRQPLHPHVQLEERGLQRGDFSDNL
RPALRTDAGEYHATVRLPNRALSCSLRLRVGQASMIASPSGVLKLSDWVLLNCSFSRPDRPVSVHW
FQGQNRVPVYNSPRHFLAETFLLLPQVSPLDSGTWGCVLTYRDGFNVSITYNLKVLGLEPVAPLTVYA
AEGSRVELPCHLPPGVGTPSLLIAKWTPPGGGPELPVAGKSGNFTLHLEAVGLAQAGTYTCSIHLQG
QQLNATVTLAVITVTPKSFGLPGSRGKLLCEVTPASGKERFVWRPLNNLSRSCPGPVLEIQEARLLAE
RWQCQLYEGQRLLGATVYAAESSSGAHSARRISGDLKGGHLVLVLILGALSLFLLVAGAFGFHWWRK
QLLLRRFSALEHGIQPFPAQRKIEELERELETEMGQEPEPEPEPQLEPEPRQL Amino acid sequence of cynomolqus LAG-3 (SEQ ID NO: 97)
MWEAQFLGLLFLQPLWVAPVKPPQPGAEISVVWAQEGAPAQLPCSPTIPLQDLSLLRRAGVTWQHQ
PDSGPPAAAPGHPPVPGHRPAAPYSWGPRPRRYTVLSVGPGGLRSGRLPLQPRVQLDERGRQRG
DFSLWLRPARRADAGEYRATVHLRDRALSCRLRLRVGQASMTASPPGSLRTSDWVILNCSFSRPDR
PASVHWFRSRGQGRVPVQGSPHHHLAESFLFLPHVGPMDSGLWGCILTYRDGFNVSIMYNLTVLGL
EPATPLTVYAGAGSRVELPCRLPPAVGTQSFLTAKWAPPGGGPDLLVAGDNGDFTLRLEDVSQAQA
GTYICHIRLQGQQLNATVTLAIITVTPKSFGSPGSLGKLLCEVTPASGQEHFVWSPLNTPSQRSFSGP
WLEAQEAQLLSQPWQCQLHQGERLLGAAVYFTELSSPGAQRSGRAPGALRAGHLPLFLILGVLFLLL
LVTGAFGFHLWRRQWRPRRFSALEQGIHPPQAQSKIEELEQEPELEPEPELERELGPEPEPGPEPEP
EQL

REFERENCES

All documents mentioned in this specification are incorporated herein by reference in their entirety.

Bae J, Lee S J, Park C G, Lee Y S, Chun T. Trafficking of LAG-3 to the surface on activated T cells via its cytoplasmic domain and protein kinase C signaling. J Immunol. 193(6), 3101-12 (2014).

Baecher-Allan C, Wolf E, Hafler D A. MHC class II expression identifies functionally distinct human regulatory T cells. J Immunol. 176(8), 4622-31 (2006).

Bedzyk W D, Johnson L S, Riordan G S, Voss E W Jr. Comparison of Variable Region Primary Structures within an Anti-Fluorescein Idiotype Family. Biol. Chem. 264, 1565-1569 (1989).

Bedzyk W D, Herron J N, Edmundson A B, Voss E W Jr. Active site structure and antigen binding properties of idiotypically cross-reactive anti-fluorescein monoclonal antibodies, J Biol Chem, 265(1), 133-8 (1990).

Bruhns P, Iannascoli B, England P, Mancardi D A, Fernandez N, Jorieux S, Daëron M. Specificity and affinity of human Fcγ receptors and their polymorphic variants for human IgG subclasses, Blood, 113, 3716-25, (2009).

Camisaschi C, Casati C, Rini F, Perego M, De Filippo A, Triebel F, Parmiani G, Belli F, Rivoltini L, Castelli C. LAG-3 expression defines a subset of CD4(+)CD25(high) Foxp3(+) regulatory T cells that are expanded at tumor sites. J Immunol. 184(11), 6545-51 (2010).

Demeure, C. E., Wolfers, J., Martin-Garcia, N., Gaulard, P. & Triebel, F. T Lymphocytes infiltrating various tumour types express the MHC class II ligand lymphocyte activation gene-3 (LAG-3): role of LAG-3/MHC class II interactions in cell-cell contacts. European Journal of Cancer 37, 1709-1718 (2001).

Durham N M, Nirschl C J, Jackson C M, Elias J, Kochel C M, Anders R A, Drake C G. Lymphocyte Activation Gene 3 (LAG-3) modulates the ability of CD4 T cells to be suppressed in vivo. PLoS One. 9(11), e109080 (2015).

Gandhi M K, Lambley E, Duraiswamy J, Dua U, Smith C, Elliott S, Gill D, Marlton P, Seymour J, Khanna R. Expression of LAG-3 by tumor-infiltrating lymphocytes is coincident with the suppression of latent membrane antigen-specific CD8+ T cell function in Hodgkin lymphoma patients. Blood 108(7), 2280-9 (2006).

Huard B, Mastrangeli R, Prigent P, et al. Characterization of the major histocompatibility complex class II binding site on LAG-3 protein. Proc Natl Acad Sci USA 94, 5744-9 (1997).

Liang B, Workman C, Lee J, Chew C, Dale B M, Colonna L, Flores M, Li N, Schweighoffer E, Greenberg S, Tybulewicz V, Vignali D, Clynes R. Regulatory T cells inhibit dendritic cells by lymphocyte activation gene-3 engagement of MHC class I I. J Immunol. 180(9), 5916-26 (2008).

Nakayama M, Akiba H, Takeda K, Kojima Y, Hashiguchi M, Azuma M, Yagita H, Okumura K. Tim-3 mediates phagocytosis of apoptotic, cells and cross-presentation, Blood. 113(16). 3821-3 (2009).

Sega E I, Leveson-Gower D B, Florek M, Schneidawind D, Luong R H, Negrin R S. Role of lymphocyte activation gene-3 (Lag-3) in conventional and regulatory T cell function in allogeneic transplantation. PLoS One. 9(1), e86551 (2014).

Sudo T, Nishikawa S, Ogawa M, Kataoka H, Ohno N, Izawa A, Hayashi S, Nishikawa S. Functional hierarchy of c-kit and c-fms in intramarrow production of CFU-M. Oncogene. 11(12), 2469-76 (1995).

Wherry E J. T cell exhaustion. Nat Immmunol. 12(6), 492-9 (2011).

Wolchok J et al; Nivolumab plus ipilimumab in advanced melanoma. N Engl J Med. 369(2), 122-33 (2013)

Woo S R, Turnis M E, Goldberg M V, Bankoti J, Selby M, Nirschl C J, Bettini M L, Gravano D M, Vogel P, Liu C L, Tangsombatvisit S, Grosso J F, Netto G, Smelizer M P, Chaux A, Utz P J, Workman C J, Pardoll D M, Korman A J, Drake C G, Vignali D A. Immune inhibitory molecules LAG-3 and PD-1 synergistically regulate T cell function to promote tumoral immune escape. Cancer Res. 72(4), 917-2 (2012).

Workman C J, Vignali D A. Negative regulation of T cell homeostasis by lymphocyte activation gene-3 (CD223). J Immunol, 174(2), 688-95 (2005).

Workman C J, Vignali D A. The CD4-related molecule, LAG-3 (CD223), regulates the expansion of activated T cells. EurJ Immunol. 33(4), 970-9 (2003).

Xu D, Alegre M L, Varga S S, Rothermel A L, Collins A M, Pulito V L, Hanna L S, Dolan K P, Parren P W, Bluestone J A, Jolliffe L K, Zivin R A. In vitro characterization of five humanized OKT3 effector function variant antibodies. Cell. Immunol. 200, 16-26 (2000)

Yamashita Y, Hooker S W, Jiang H, Laurent A B, Resta R, Khare K, Coe A, Kincade P W, Thompson L F. CD73 expression and fyn-dependent signaling on murine lymphocytes. Eur J Immunol. 28(10), 2981-90 (1998).

---

The invention claimed is:

1. A specific binding member which binds to lymphocyte-activation gene 3 (LAG-3), comprising a LAG-3 antigen-binding site located in a CH3 domain of the specific binding member, wherein the LAG-3 binding site comprises the amino acid sequences WDEPWGED (SEQ ID NO: 1) and PYDRWVWPDE (SEQ ID NO: 3), and wherein the amino acid sequence WDEPWGED is located in a first structural loop of the CH3 domain and the amino acid sequence PYDRWVWPDE is located in a second structural loop of the CH3 domain wherein the specific binding member does not comprise a CDR-based antigen binding site for PD-L1.

2. A specific binding member according to claim 1, wherein the LAG-3 antigen-binding site comprises the amino acid sequence set forth in SEQ ID NO: 1 in the AB loop, and the amino acid sequence set forth in SEQ ID NO: 3 in the EF loop of the CH3 domain.

3. A specific binding member according to claim 1, wherein the LAG-3 antigen-binding site further comprises one of the following sequences:

```
                              (SEQ ID NOS 2, 8 and 18)
(i)   SNGQPENNY;

(SEQ ID NO: 13)
(ii)  SNGQPEDNY;

(SEQ ID NO: 23)
(iii) SNGYPEIEF;

(SEQ ID NO: 28)
(iv)  SNGIPEWNY;

(SEQ ID NO: 33)
(v)   SNGYAEYNY;

(SEQ ID NO: 38)
(vi)  SNGYKEENY;

(SEQ ID NO: 43)
(vii) SNGVPELNV;
or (SEQ ID NO: 48)
(viii) SNGYQEDNY.
```

4. A specific binding member according to claim 3, wherein the LAG-3 antigen-binding site comprises the amino acid sequence set forth in SEQ ID NO: 2, 8, 13, 18, 23, 28, 33, 38, 43, or 48 in the CD loop of the CH3 domain.

5. A specific binding member according to claim 1, wherein the specific binding member comprises the CH3 domain set forth in SEQ ID NO: 5, 10, 15, 20, 25, 30, 35, 40, 45, or 50.

6. A specific binding member according to claim 1, wherein the specific binding member further comprises a CH2 domain.

7. A specific binding member according to claim 1, wherein the specific binding member comprises the sequence set forth in SEQ ID NO: 6, 7, 11, 12, 16, 17, 21, 22, 26, 27, 31, 32, 36, 37, 41, 42, 46, 47, 51, or 52.

8. A specific binding member according to claim 6 further comprising an immunoglobulin hinge region, or part thereof, at the N-terminus of the CH2 domain.

9. A specific binding member according to claim 1, wherein the specific binding member further comprises a second antigen-binding site.

10. A specific binding member according to claim 9, wherein the specific binding member is an antibody molecule.

11. A specific binding member according to claim 10, wherein the second antigen-binding site binds to a molecule which is an immune system modulator.

12. A specific binding member according to claim 1, wherein the specific binding member is conjugated to an immune system modulator, cytotoxic molecule, radioisotope, or detectable label.

13. A nucleic acid encoding a specific binding member according to claim 1.

14. A vector comprising the nucleic acid of claim 13.

15. A recombinant host cell comprising the nucleic acid of claim 13.

16. A method of producing a specific binding member, comprising culturing the recombinant host cell of claim 15 under conditions for production of the specific binding member.

17. A pharmaceutical composition comprising a specific binding member according to claim 1 and a pharmaceutically acceptable excipient.

18. A method of treating cancer in a patient, wherein the method comprises administering to the patient a therapeutically effective amount of a specific binding member according to claim 1.

19. A method according to claim 18, wherein the cancer is selected from the group consisting of: Hodgkin's lymphoma, non-Hodgkin's lymphoma, ovarian cancer, prostate cancer, colorectal cancer, fibrosarcoma, renal cell carcinoma, melanoma, pancreatic cancer, breast cancer, glioblastoma multiforme, lung cancer, head and neck cancer, stomach cancer, bladder cancer, cervical cancer, uterine cancer, vulvar cancer, testicular cancer, penile cancer, leukemia, multiple myeloma, squamous cell cancer, testicular cancer, esophageal cancer, Kaposi's sarcoma, and central nervous system (CNS) lymphoma, hepatocellular carcinoma, nasopharyngeal cancer, Merkel cell carcinoma, and mesothelioma.

20. An antibody molecule which binds to an immune system modulator and lymphocyte-activation gene 3 (LAG-3), wherein the antibody molecule comprises:
  (i) a CDR-based antigen binding site for the immune system modulator, wherein the CDR-based antigen-binding site is not a binding site for PD-L1; and
  (ii) a LAG-3 antigen binding site located in a CH3 domain of the antibody molecule, wherein the LAG-3 binding site comprises the amino acid sequences WDEPWGED (SEQ ID NO: 1) and PYDRWVWPDE (SEQ ID NO: 3), and wherein the amino acid sequence WDEPWGED is located in a first structural loop of the CH3 domain and the amino acid sequence PYDRWVWPDE is located in a second structural loop of the CH3 domain.

* * * * *

UNITED STATES PATENT AND TRADEMARK OFFICE
CERTIFICATE OF CORRECTION

Page 1 of 1

PATENT NO. : 11,214,618 B2
APPLICATION NO. : 16/311596
DATED : January 4, 2022
INVENTOR(S) : Tuna et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this
Eighteenth Day of February, 2025

Coke Morgan Stewart
*Acting Director of the United States Patent and Trademark Office*

SEQUENCE LISTING

```
<160> NUMBER OF SEQ ID NOS: 99

<210> SEQ ID NO 1
<211> LENGTH: 8
<212> TYPE: PRT
<213> ORGANISM: Artificial Sequence
<220> FEATURE:
<223> OTHER INFORMATION: FS18-7-9 AB loop

<400> SEQUENCE: 1

Trp Asp Glu Pro Trp Gly Glu Asp
1               5

<210> SEQ ID NO 2
<211> LENGTH: 9
<212> TYPE: PRT
```

```
<213> ORGANISM: Artificial Sequence
<220> FEATURE:
<223> OTHER INFORMATION: FS18-7-9 CD loop

<400> SEQUENCE: 2

Ser Asn Gly Gln Pro Glu Asn Asn Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: FS18-7-9 EF loop

<400> SEQUENCE: 3

Pro Tyr Asp Arg Trp Val Trp Pro Asp Glu
1               5                   10

<210> SEQ ID NO 4
<211> LENGTH: 318
<212> TYPE: DNA
<213> ORGANISM: Artificial Sequence
<220> FEATURE:
<223> OTHER INFORMATION: Nucleotide sequence of Fcab FS18-7-9 CH3 domain

<400> SEQUENCE: 4
ggccagcctc gagaaccaca ggtgtacacc ctgcccccat cctgggatga gccgtggggt      60
gaagacgtca gcctgacctg cctggtcaaa ggcttctatc ccagcgaaat cgccgtggag     120
tgggagagca atgggcagcc ggagaacaac tacaagacca cgcctcccgt gctggactcc     180
gacggctcct tcttcctcta cagcaagctc accgtgccgt atgataggtg ggtttggccg     240
gatgagttct catgctccgt gatgcatgag gctctgcaca accactacac acagaagagc     300
ctctccctgt ctccgggt                                                   318

<210> SEQ ID NO 5
<211> LENGTH: 106
<212> TYPE: PRT
<213> ORGANISM: Artificial Sequence
<220> FEATURE:
<223> OTHER INFORMATION: Amino acid sequence of Fcab FS18-7-9 CH3 domain

<400> SEQUENCE: 5

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 6
<211> LENGTH: 216
<212> TYPE: PRT
```

```
<213> ORGANISM: Artificial Sequence
<220> FEATURE:
<223> OTHER INFORMATION: Amino acid sequence of Fcab FS18-7-9 CH2 and
      CH3 domains, comprising LALA mutation

<400> SEQUENCE: 6

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 7
<211> LENGTH: 216
<212> TYPE: PRT
<213> ORGANISM: Artificial Sequence
<220> FEATURE:
<223> OTHER INFORMATION: Amino acid sequence of Fcab FS18-7-9 CH2 and
      CH3 domains without LALA mutation

<400> SEQUENCE: 7

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
```

```
                     100                 105                 110
Pro Arg Glu Pro Gln Val Tyr Thr Leu Pro Pro Ser Trp Asp Glu Pro
            115                 120                 125

Trp Gly Glu Asp Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
        210                 215

<210> SEQ ID NO 8
<211> LENGTH: 9
<212> TYPE: PRT
<213> ORGANISM: Artificial Sequence
<220> FEATURE:
<223> OTHER INFORMATION: FS18-7-32 CD loop

<400> SEQUENCE: 8

Ser Asn Gly Gln Pro Glu Asn Asn Tyr
1               5

<210> SEQ ID NO 9
<211> LENGTH: 318
<212> TYPE: DNA
<213> ORGANISM: Artificial Sequence
<220> FEATURE:
<223> OTHER INFORMATION: Nucleotide sequence of Fcab FS18-7-32 CH3
      domain

<400> SEQUENCE: 9
ggccagcctc gagaaccaca ggtgtacacc ctgcccccat cctgggatga gccgtggggt     60
gaagacgtca gcctgacctg cctggtcaaa ggcttctatc ccagcgaaat cgccgtggag    120
tgggagagca atgggcagcc ggagaacaac tacaagacca cgcctcccgt gctggactcc    180
gacggctcct tcttcctcta cagcaagctc accgtgccgt atgataggtg ggtttggccg    240
gatgagttct catgctccgt gatgcatgag gctctgcaca accactacac acagaagagc    300
ctctccctgt ctccgggt                                                   318

<210> SEQ ID NO 10
<211> LENGTH: 106
<212> TYPE: PRT
<213> ORGANISM: Artificial Sequence
<220> FEATURE:
<223> OTHER INFORMATION: Amino acid sequence of Fcab FS18-7-32 CH3
      domain

<400> SEQUENCE: 10

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Glu Ile Ala Val Glu Trp Glu Ser Asn Gly Gln Pro Glu
        35                  40                  45
```

```
Asn Asn Tyr Lys Thr Thr Pro Val Leu Asp Ser Asp Gly Ser Phe
 50                  55                  60

Phe Leu Tyr Ser Lys Leu Thr Val Pro Tyr Asp Arg Trp Val Trp Pro
 65                  70                  75                  80

Asp Glu Phe Ser Cys Ser Val Met His Glu Ala Leu His Asn His Tyr
                 85                  90                  95

Thr Gln Lys Ser Leu Ser Leu Ser Pro Gly
                100                 105
```

<210> SEQ ID NO 11
<211> LENGTH: 216
<212> TYPE: PRT
<213> ORGANISM: Artificial Sequence
<220> FEATURE:
<223> OTHER INFORMATION: Amino acid sequence of Fcab FS18-7-32 CH2 and
      CH3 domains, comprising LALA mutation

<400> SEQUENCE: 11

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Trp Asp Glu Pro
            115                 120                 125

Trp Gly Glu Asp Val Ser Leu Thr Cys Leu Val Lys Gly Phe Tyr Pro
130                 135                 140

Ser Glu Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
        210                 215
```

<210> SEQ ID NO 12
<211> LENGTH: 216
<212> TYPE: PRT
<213> ORGANISM: Artificial Sequence
<220> FEATURE:
<223> OTHER INFORMATION: Amino acid sequence of Fcab FS18-7-32 CH2 and
      CH3 domains without LALA mutation

<400> SEQUENCE: 12

```
Ala Pro Glu Leu Leu Gly Gly Pro Ser Val Phe Leu Phe Pro Pro Lys
 1               5                  10                  15
```

```
Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Glu Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 13
<211> LENGTH: 9
<212> TYPE: PRT
<213> ORGANISM: Artificial Sequence
<220> FEATURE:
<223> OTHER INFORMATION: FS18-7-33 CD loop

<400> SEQUENCE: 13

Ser Asn Gly Gln Pro Glu Asp Asn Tyr
1               5

<210> SEQ ID NO 14
<211> LENGTH: 318
<212> TYPE: DNA
<213> ORGANISM: Artificial Sequence
<220> FEATURE:
<223> OTHER INFORMATION: Nucleotide sequence of Fcab FS18-7-33 CH3
      domain

<400> SEQUENCE: 14
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca atgggcagcc ggaggacaac tacaagacca cgcctcccgt gctggactcc     180
gacggctcct tcttcctcta cagcaagctc accgtgccgt atgataggtg gtttggccg      240 gatgagttct catgctccgt gatgcatgag gctctgcaca accactacac acagaagagc     300 ctctcccctgt ctccgggt                                                  318

<210> SEQ ID NO 15
<211> LENGTH: 106
<212> TYPE: PRT
```

```
<213> ORGANISM: Artificial Sequence
<220> FEATURE:
<223> OTHER INFORMATION: Amino acid sequence of Fcab FS18-7-33 CH3
      domain

<400> SEQUENCE: 15

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asp Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 16
<211> LENGTH: 216
<212> TYPE: PRT
<213> ORGANISM: Artificial Sequence
<220> FEATURE:
<223> OTHER INFORMATION: Amino acid sequence of Fcab FS18-7-33 CH2 and
      CH3 domains, comprising LALA mutation

<400> SEQUENCE: 16

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 17
<211> LENGTH: 216
<212> TYPE: PRT
<213> ORGANISM: Artificial Sequence
<220> FEATURE:
<223> OTHER INFORMATION: Amino acid sequence of Fcab FS18-7-33 CH2 and
      CH3 domains without LALA mutation

<400> SEQUENCE: 17

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Trp Asp Glu Pro
        115                 120                 125
Trp Gly Glu Asp Val Ser Leu Thr Cys Leu Val Lys Gly Phe Tyr Pro
    130                 135                 140
Ser Asp Ile Ala Val Glu Trp Glu Ser Asn Gly Gln Pro Glu Asp Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Pro Tyr Asp Arg Trp Val Trp Pro Asp Glu
            180                 185                 190
Phe Ser Cys Ser Val Met His Glu Ala Leu His Asn His Tyr Thr Gln
        195                 200                 205
Lys Ser Leu Ser Leu Ser Pro Gly
    210                 215
```

<210> SEQ ID NO 18
<211> LENGTH: 9
<212> TYPE: PRT
<213> ORGANISM: Artificial Sequence
<220> FEATURE:
<223> OTHER INFORMATION: FS18-7-36 CD loop

<400> SEQUENCE: 18

```
Ser Asn Gly Gln Pro Glu Asn Asn Tyr
1               5
```

<210> SEQ ID NO 19
<211> LENGTH: 318
<212> TYPE: DNA
<213> ORGANISM: Artificial Sequence
<220> FEATURE:
<223> OTHER INFORMATION: Nucleotide sequence of Fcab FS18-7-36 CH3
      domain

<400> SEQUENCE: 19

```
ggccagcctc gagaaccaca ggtgtacacc ctgcccccat cctgggatga gccgtggggt      60
gaagacgtca gcctgacctg cctggtcaaa ggcttctatc ccagcgacat cgccgtggag    120
tgggagagca atgggcagcc ggagaacaac tacaagacca cgcctcccgt gctggactcc    180
gacggctcct acttcctcta cagcaagctc accgtgccgt atgataggtg ggtttggccg    240
gatgagttct catgctccgt gatgcatgag gctctgcaca accactacac acagaagagc    300 ctctcccctgt ctccgggt                                                  318
```

```
<210> SEQ ID NO 20
<211> LENGTH: 106
<212> TYPE: PRT
<213> ORGANISM: Artificial Sequence
<220> FEATURE:
<223> OTHER INFORMATION: Amino acid sequence of Fcab FS18-7-36 CH3
      domain

<400> SEQUENCE: 20

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Tyr
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105
```

```
<210> SEQ ID NO 21
<211> LENGTH: 216
<212> TYPE: PRT
<213> ORGANISM: Artificial Sequence
<220> FEATURE:
<223> OTHER INFORMATION: Amino acid sequence of CH2+CH3 of Fcab
      FS18-7-36 CH2 and CH3 domains, comprising LALA mutation

<400> SEQUENCE: 21

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125
```

```
Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Tyr Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
            195                 200                 205

Lys Ser Leu Ser Leu Ser Pro Gly
210                 215

<210> SEQ ID NO 22
<211> LENGTH: 216
<212> TYPE: PRT
<213> ORGANISM: Artificial Sequence
<220> FEATURE:
<223> OTHER INFORMATION: Amino acid sequence of Fcab FS18-7-36 CH2 and
      CH3 domains without LALA mutation

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Tyr Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
            195                 200                 205

Lys Ser Leu Ser Leu Ser Pro Gly
210                 215

<210> SEQ ID NO 23
<211> LENGTH: 9
<212> TYPE: PRT
<213> ORGANISM: Artificial Sequence
<220> FEATURE:
<223> OTHER INFORMATION: FS18-7-58 CD loop
```

```
<400> SEQUENCE: 23

Ser Asn Gly Tyr Pro Glu Ile Glu Phe
1               5

<210> SEQ ID NO 24
<211> LENGTH: 318
<212> TYPE: DNA
<213> ORGANISM: Artificial Sequence
<220> FEATURE:
<223> OTHER INFORMATION: Nucleotide sequence of Fcab FS18-7-58 CH3
      domain

<400> SEQUENCE: 24
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca atgggtatcc agaaatcgaa ttcaagacca cgcctcccgt gctggactcc     180
gacggctcct tcttcctcta cagcaagctc accgtgcctt atgataggtg ggtttggccg     240
gatgagttct catgctccgt gatgcatgag gctctgcaca accactacac acagaagagc     300 ctctcccctgt ctccgggt                                                  318

<210> SEQ ID NO 25
<211> LENGTH: 106
<212> TYPE: PRT
<213> ORGANISM: Artificial Sequence
<220> FEATURE:
<223> OTHER INFORMATION: Amino acid sequence of Fcab FS18-7-58 CH3
      domain

<400> SEQUENCE: 25

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Tyr Pro Glu
        35                  40                  45

Ile Glu Phe Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 26
<211> LENGTH: 216
<212> TYPE: PRT
<213> ORGANISM: Artificial Sequence
<220> FEATURE:
<223> OTHER INFORMATION: Amino acid sequence of Fcab FS18-7-58 CH2 and
      CH3 domains, comprising LALA mutation

<400> SEQUENCE: 26

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Pro Glu Ile Glu
145                 150                 155                 160

Phe Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 27
<211> LENGTH: 216
<212> TYPE: PRT
<213> ORGANISM: Artificial Sequence
<220> FEATURE:
<223> OTHER INFORMATION: Amino acid sequence of Fcab FS18-7-58 CH2 and
      CH3 domains without LALA mutation

<400> SEQUENCE: 27

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Pro Glu Ile Glu
145                 150                 155                 160

Phe Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu

```
                180               185               190
Phe Ser Cys Ser Val Met His Glu Ala Leu His Asn His Tyr Thr Gln
            195               200               205
Lys Ser Leu Ser Leu Ser Pro Gly
    210               215

<210> SEQ ID NO 28
<211> LENGTH: 9
<212> TYPE: PRT
<213> ORGANISM: Artificial Sequence
<220> FEATURE:
<223> OTHER INFORMATION: FS18-7-62 CD loop

<400> SEQUENCE: 28

Ser Asn Gly Ile Pro Glu Trp Asn Tyr
1               5

<210> SEQ ID NO 29
<211> LENGTH: 318
<212> TYPE: DNA
<213> ORGANISM: Artificial Sequence
<220> FEATURE:
<223> OTHER INFORMATION: Nucleotide sequence of Fcab FS18-7-62 CH3
      domain

<400> SEQUENCE: 29
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca atgggatccc agaatggaac tataagacca cgcctccgt gctggactcc      180 gacggctcct tcttcctcta cagcaagctc accgtgccgt atgataggtg ggtttggccg     240
gatgagttct catgctccgt gatgcatgag gctctgcaca accactacac acagaagagc     300 ctctcccctgt ctccgggt                                                  318

<210> SEQ ID NO 30
<211> LENGTH: 106
<212> TYPE: PRT
<213> ORGANISM: Artificial Sequence
<220> FEATURE:
<223> OTHER INFORMATION: Amino acid sequence of Fcab FS18-7-62 CH3
      domain

<400> SEQUENCE: 30

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Ile Pro Glu
        35                  40                  45

Trp Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 31
<211> LENGTH: 216
```

<212> TYPE: PRT
<213> ORGANISM: Artificial Sequence
<220> FEATURE:
<223> OTHER INFORMATION: Amino acid sequence of Fcab FS18-7-62 CH2 and
      CH3 domains, comprising LALA mutation

<400> SEQUENCE: 31

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Ile Pro Glu Trp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 32
<211> LENGTH: 216
<212> TYPE: PRT
<213> ORGANISM: Artificial Sequence
<220> FEATURE:
<223> OTHER INFORMATION: Amino acid sequence of Fcab FS18-7-62 CH2 and
      CH3 domains without LALA mutation

<400> SEQUENCE: 32

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

-continued

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Ile Pro Glu Trp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 33
<211> LENGTH: 9
<212> TYPE: PRT
<213> ORGANISM: Artificial Sequence
<220> FEATURE:
<223> OTHER INFORMATION: FS18-7-65 CD loop

<400> SEQUENCE: 33

```
Ser Asn Gly Tyr Ala Glu Tyr Asn Tyr
1               5
```

<210> SEQ ID NO 34
<211> LENGTH: 318
<212> TYPE: DNA
<213> ORGANISM: Artificial Sequence
<220> FEATURE:
<223> OTHER INFORMATION: Nucleotide sequence of Fcab FS18-7-65 CH3
      domain

<400> SEQUENCE: 34

```
ggccagcctc gagaaccaca ggtgtacacc ctgcccccat cctgggatga gccgtggggt    60
gaagacgtca gcctgacctg cctggtcaaa ggcttctatc ccagcgacat cgccgtggag   120
tgggagagca atgggtatgc agaatataac tataagacca cgcctcccgt gctggactcc   180
gacggctcct tcttcctcta cagcaagctc accgtgccgt atgataggtg ggtttggccg   240
gatgagttct catgctccgt gatgcatgag gctctgcaca accactacac acagaagagc   300
ctctcccTGT ctccgggt                                                  318
```

<210> SEQ ID NO 35
<211> LENGTH: 106
<212> TYPE: PRT
<213> ORGANISM: Artificial Sequence
<220> FEATURE:
<223> OTHER INFORMATION: Amino acid sequence of Fcab FS18-7-65 CH3
      domain

<400> SEQUENCE: 35

```
Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Tyr Ala Glu
        35                  40                  45
```

Tyr Asn Tyr Lys Thr Thr Pro Pro Val Leu Asp Ser Asp Gly Ser Phe
            50                  55                  60

Phe Leu Tyr Ser Lys Leu Thr Val Pro Tyr Asp Arg Trp Val Trp Pro
 65                  70                  75                  80

Asp Glu Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 36
<211> LENGTH: 216
<212> TYPE: PRT
<213> ORGANISM: Artificial Sequence
<220> FEATURE:
<223> OTHER INFORMATION: Amino acid sequence of Fcab FS18-7-65 CH2 and
      CH3 domains, comprising LALA mutation

<400> SEQUENCE: 36

Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Ala Glu Tyr Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 37
<211> LENGTH: 216
<212> TYPE: PRT
<213> ORGANISM: Artificial Sequence
<220> FEATURE:
<223> OTHER INFORMATION: Amino acid sequence of Fcab FS18-7-65 CH2 and
      CH3 domains without LALA mutation

<400> SEQUENCE: 37

Ala Pro Glu Leu Leu Gly Gly Pro Ser Val Phe Leu Phe Pro Pro Lys
 1               5                  10                  15

-continued

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
130                 135                 140

Ser Asp Ile Ala Val Glu Trp Glu Ser Asn Gly Tyr Ala Glu Tyr Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 38
<211> LENGTH: 9
<212> TYPE: PRT
<213> ORGANISM: Artificial Sequence
<220> FEATURE:
<223> OTHER INFORMATION: FS18-7-78 CD loop

<400> SEQUENCE: 38

```
Ser Asn Gly Tyr Lys Glu Glu Asn Tyr
1               5
```

<210> SEQ ID NO 39
<211> LENGTH: 318
<212> TYPE: DNA
<213> ORGANISM: Artificial Sequence
<220> FEATURE:
<223> OTHER INFORMATION: Nucleotide sequence of Fcab FS18-7-78 CH3 domain

<400> SEQUENCE: 39

```
ggccagcctc gagaaccaca ggtgtacacc ctgcccccat cctgggatga gccgtggggt    60
gaagacgtca gcctgacctg cctggtcaaa ggcttctatc ccagcgacat cgccgtggag   120
tgggagagca atgggtataa agaagaaaac tataagacca cgcctcccgt gctggactcc   180
gacggctcct tcttcctcta cagcaagctc accgtgccgt atgataggtg ggtttggccg   240
gatgagttct catgctccgt gatgcatgag gctctgcaca accactacac acagaagagc   300
ctctccctgt ctccgggt                                                318
```

<210> SEQ ID NO 40
<211> LENGTH: 106

```
<212> TYPE: PRT
<213> ORGANISM: Artificial Sequence
<220> FEATURE:
<223> OTHER INFORMATION: Amino acid sequence of Fcab FS18-7-78 CH3
      domain

<400> SEQUENCE: 40

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Tyr Lys Glu
        35                  40                  45

Glu Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 41
<211> LENGTH: 216
<212> TYPE: PRT
<213> ORGANISM: Artificial Sequence
<220> FEATURE:
<223> OTHER INFORMATION: Amino acid sequence of Fcab FS18-7-78 CH2 and
      CH3 domains, comprising LALA mutation

<400> SEQUENCE: 41

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Lys Glu Glu Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205
```

Lys Ser Leu Ser Leu Ser Pro Gly
    210                 215

<210> SEQ ID NO 42
<211> LENGTH: 216
<212> TYPE: PRT
<213> ORGANISM: Artificial Sequence
<220> FEATURE:
<223> OTHER INFORMATION: Amino acid sequence of Fcab FS18-7-78 CH2 and
      CH3 domains without LALA mutation

<400> SEQUENCE: 42

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Lys Glu Glu Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 43
<211> LENGTH: 9
<212> TYPE: PRT
<213> ORGANISM: Artificial Sequence
<220> FEATURE:
<223> OTHER INFORMATION: FS18-7-88 CD loop

<400> SEQUENCE: 43

Ser Asn Gly Val Pro Glu Leu Asn Val
1               5

<210> SEQ ID NO 44
<211> LENGTH: 318
<212> TYPE: DNA
<213> ORGANISM: Artificial Sequence
<220> FEATURE:
<223> OTHER INFORMATION: Nucleotide sequence of Fcab FS18-7-88 CH3
      domain

<400> SEQUENCE: 44

```
ggccagcctc gagaaccaca ggtgtacacc ctgcccccat cctgggatga gccgtggggt    60
gaagacgtca gcctgacctg cctggtcaaa ggcttctatc ccagcgacat cgccgtggag   120
tgggagagca atgggttcc agaactgaac gttaagacca cgcctcccgt gctggactcc   180
gacggctcct tcttcctcta cagcaagctc accgtgccgt atgataggtg ggtttggccg   240
gatgagttct catgctccgt gatgcatgag gctctgcaca accactacac acagaagagc   300 ctctcccctgt ctccgggt                                                318
```

<210> SEQ ID NO 45
<211> LENGTH: 106
<212> TYPE: PRT
<213> ORGANISM: Artificial Sequence
<220> FEATURE:
<223> OTHER INFORMATION: Amino acid sequence of Fcab FS18-7-88 CH3 domain

<400> SEQUENCE: 45

```
Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Val Pro Glu
        35                  40                  45

Leu Asn Val Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 46
<211> LENGTH: 216
<212> TYPE: PRT
<213> ORGANISM: Artificial Sequence
<220> FEATURE:
<223> OTHER INFORMATION: Amino acid sequence of Fcab FS18-7-88 CH2 and CH3 domains, comprising LALA mutation

<400> SEQUENCE: 46

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125
```

```
Trp Gly Glu Asp Val Ser Leu Thr Cys Leu Val Lys Gly Phe Tyr Pro
            130                 135                 140

Ser Asp Ile Ala Val Glu Trp Glu Ser Asn Gly Val Pro Glu Leu Asn
145                 150                 155                 160

Val Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
                195                 200                 205

Lys Ser Leu Ser Leu Ser Pro Gly
            210                 215

<210> SEQ ID NO 47
<211> LENGTH: 216
<212> TYPE: PRT
<213> ORGANISM: Artificial Sequence
<220> FEATURE:
<223> OTHER INFORMATION: Amino acid sequence of Fcab FS18-7-88 CH2 and
      CH3 domains without LALA mutation

<400> SEQUENCE: 47

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
            130                 135                 140

Ser Asp Ile Ala Val Glu Trp Glu Ser Asn Gly Val Pro Glu Leu Asn
145                 150                 155                 160

Val Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
                195                 200                 205

Lys Ser Leu Ser Leu Ser Pro Gly
            210                 215

<210> SEQ ID NO 48
<211> LENGTH: 9
<212> TYPE: PRT
<213> ORGANISM: Artificial Sequence
<220> FEATURE:
<223> OTHER INFORMATION: FS18-7-95 CD loop
```

<400> SEQUENCE: 48

Ser Asn Gly Tyr Gln Glu Asp Asn Tyr
1               5

<210> SEQ ID NO 49
<211> LENGTH: 318
<212> TYPE: DNA
<213> ORGANISM: Artificial Sequence
<220> FEATURE:
<223> OTHER INFORMATION: Nucleotide sequence of Fcab FS18-7-95 CH3
      domain

<400> SEQUENCE: 49

```
ggccagcctc gagaaccaca ggtgtacacc ctgcccccat cctgggatga gccgtggggt    60
gaagacgtca gcctgacctg cctggtcaaa ggcttctatc ccagcgacat cgccgtggag   120
tgggagagca atgggtatca ggaagataac tataagacca cgcctcccgt gctggactcc   180
gacggctcct tcttcctcta cagcaagctc accgtgccgt atgataggtg ggtttggccg   240
gatgagttct catgctccgt gatgcatgag gctctgcaca accactacac acagaagagc   300
ctctcccctgt ctccgggt                                                318
```

<210> SEQ ID NO 50
<211> LENGTH: 106
<212> TYPE: PRT
<213> ORGANISM: Artificial Sequence
<220> FEATURE:
<223> OTHER INFORMATION: Amino acid sequence of Fcab FS18-7-95 CH3
      domain

<400> SEQUENCE: 50

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Tyr Gln Glu
        35                  40                  45

Asp Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 51
<211> LENGTH: 216
<212> TYPE: PRT
<213> ORGANISM: Artificial Sequence
<220> FEATURE:
<223> OTHER INFORMATION: Amino acid sequence of Fcab FS18-7-95 CH2 and
      CH3 domains, comprising LALA mutation

<400> SEQUENCE: 51

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr

```
                35                  40                  45
Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Gln Glu Asp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 52
<211> LENGTH: 216
<212> TYPE: PRT
<213> ORGANISM: Artificial Sequence
<220> FEATURE:
<223> OTHER INFORMATION: Amino acid sequence of Fcab FS18-7-95 CH2 and
      CH3 domains without LALA mutation

<400> SEQUENCE: 52

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Gln Glu Asp Asn
145                 150                 155                 160

Tyr Lys Thr Thr Pro Pro Val Leu Asp Ser Asp Gly Ser Phe Phe Leu
                165                 170                 175
```

```
Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 53
<211> LENGTH: 110
<212> TYPE: PRT
<213> ORGANISM: Artificial Sequence
<220> FEATURE:
<223> OTHER INFORMATION: Amino acid sequence of the wild-type human IgG1
      CH2 domain

<400> SEQUENCE: 53

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 54
<211> LENGTH: 110
<212> TYPE: PRT
<213> ORGANISM: Artificial Sequence
<220> FEATURE:
<223> OTHER INFORMATION: Amino acid sequence of the human IgG1 CH2
      domain comprising the "LALA mutation"

<400> SEQUENCE: 54

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 55
<211> LENGTH: 216
<212> TYPE: PRT
<213> ORGANISM: Artificial Sequence
<220> FEATURE:
```

<223> OTHER INFORMATION: Amino acid sequence of "wild-type" Fcab CH2 and
      CH3 domains without LALA mutation

<400> SEQUENCE: 55

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 56
<211> LENGTH: 216
<212> TYPE: PRT
<213> ORGANISM: Artificial Sequence
<220> FEATURE:
<223> OTHER INFORMATION: Amino acid sequence of "wild-type" Fcab CH2 and
      CH3 domains, comprising LALA mutation

<400> SEQUENCE: 56

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 57
<211> LENGTH: 15
<212> TYPE: PRT
<213> ORGANISM: Artificial Sequence
<220> FEATURE:
<223> OTHER INFORMATION: Amino acid sequence of the human IgG1 hinge
      region

<400> SEQUENCE: 57

Glu Pro Lys Ser Cys Asp Lys Thr His Thr Cys Pro Pro Cys Pro
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: Amino acid sequence of the human IgG1 truncated
      hinge region

<400> SEQUENCE: 58

Thr Cys Pro Pro Cys Pro
1               5

<210> SEQ ID NO 59
<211> LENGTH: 222
<212> TYPE: PRT
<213> ORGANISM: Artificial Sequence
<220> FEATURE:
<223> OTHER INFORMATION: Amino acid sequence anti-mouse LAG-3 Fcab
      FS18-7-108-29, comprising LALA mutation

<400> SEQUENCE: 59

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
```

Ser Lys Ala Lys Gly Gln Pro Arg Glu Pro Gln Val Tyr Thr Leu Pro
            115                 120                 125

Pro Ser Trp Asp Glu Pro Trp Gly Glu Asp Val Ser Leu Thr Cys Leu
        130                 135                 140

Val Lys Gly Phe Tyr Pro Ser Asp Ile Val Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Pro Phe Glu Arg
            180                 185                 190

Trp Met Trp Pro Asp Glu Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 60
<211> LENGTH: 222
<212> TYPE: PRT
<213> ORGANISM: Artificial Sequence
<220> FEATURE:
<223> OTHER INFORMATION: Amino acid sequence of the anti-mouse LAG-3
      Fcab FS18-7-108-29 without LALA mutation

<400> SEQUENCE: 60

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Trp Asp Glu Pro Trp Gly Glu Asp Val Ser Leu Thr Cys Leu
        130                 135                 140

Val Lys Gly Phe Tyr Pro Ser Asp Ile Val Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Pro Phe Glu Arg
            180                 185                 190

Trp Met Trp Pro Asp Glu Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 61
<211> LENGTH: 222

```
<212> TYPE: PRT
<213> ORGANISM: Artificial Sequence
<220> FEATURE:
<223> OTHER INFORMATION: Amino acid sequence of the anti-mouse LAG-3
      Fcab FS18-7-108-35, comprising LALA mutation

<400> SEQUENCE: 61

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Trp Asp Glu Pro Trp Gly Glu Asp Val Ser Leu Thr Cys Leu
    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Pro Phe Glu Arg
            180                 185                 190

Trp Met Trp Pro Asp Glu Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 62
<211> LENGTH: 222
<212> TYPE: PRT
<213> ORGANISM: Artificial Sequence
<220> FEATURE:
<223> OTHER INFORMATION: Amino acid sequence of the anti-mouse LAG-3
      Fcab FS18-7-108-35 without LALA mutation

<400> SEQUENCE: 62

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

```
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Trp Asp Glu Pro Trp Gly Glu Asp Val Ser Leu Thr Cys Leu
    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Pro Phe Glu Arg
            180                 185                 190

Trp Met Trp Pro Asp Glu Phe Ser Cys Ser Val Met His Glu Ala Leu
        195                 200                 205

His Asn His Tyr Thr Gln Lys Ser Leu Ser Leu Ser Pro Gly
    210                 215                 220
```

<210> SEQ ID NO 63
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-9/4420 comprising LALA mutation

<400> SEQUENCE: 63

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 64
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-9/4420 without LALA mutation

<400> SEQUENCE: 64

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

Ser Gly Ala Leu Thr Ser Gly Val His Thr Phe Pro Ala Val Leu Gln
145                 150                 155                 160

Ser Ser Gly Leu Tyr Ser Leu Ser Ser Val Val Thr Val Pro Ser Ser
            165                 170                 175

Ser Leu Gly Thr Gln Thr Tyr Ile Cys Asn Val Asn His Lys Pro Ser
        180                 185                 190

Asn Thr Lys Val Asp Lys Lys Val Glu Pro Lys Ser Cys Asp Lys Thr
    195                 200                 205

His Thr Cys Pro Pro Cys Pro Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
            245                 250                 255

Glu Val Lys Phe Asn Trp Tyr Val Asp Gly Val Glu Val His Asn Ala
        260                 265                 270

Lys Thr Lys Pro Arg Glu Glu Gln Tyr Asn Ser Thr Tyr Arg Val Val
    275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
            325                 330                 335

Pro Pro Ser Trp Asp Glu Pro Trp Gly Glu Asp Val Ser Leu Thr Cys
        340                 345                 350

Leu Val Lys Gly Phe Tyr Pro Ser Asp Ile Ala Val Glu Trp Glu Ser
    355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Pro Tyr Asp
385                 390                 395                 400

Arg Trp Val Trp Pro Asp Glu Phe Ser Cys Ser Val Met His Glu Ala
            405                 410                 415

Leu His Asn His Tyr Thr Gln Lys Ser Leu Ser Leu Ser Pro Gly
        420                 425                 430
                                                        435
                                    440                 445

<210> SEQ ID NO 65
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-32/4420 comprising LALA mutation

<400> SEQUENCE: 65

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Glu Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 66
<211> LENGTH: 447
<212> TYPE: PRT
<213> ORGANISM: Artificial Sequence
<220> FEATURE:
<223> OTHER INFORMATION: Amino acid sequence of the heavy chain of anti-human LAG-3/FITC mAb2 FS18-7-32/without LALA mutation

<400> SEQUENCE: 66

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Glu Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 67
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-33/4420 comprising LALA mutation

<400> SEQUENCE: 67

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 68
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-33/4420 without LALA mutation

<400> SEQUENCE: 68

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
```

```
225                 230                 235                 240
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 69
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-36/4420 comprising LALA mutation

<400> SEQUENCE: 69

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Tyr Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 70
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-36/4420 without LALA mutation

<400> SEQUENCE: 70

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60
```

```
Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Gly Met Asp Tyr Trp Gly Gln Gly Thr
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Tyr Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 71
<211> LENGTH: 447
<212> TYPE: PRT
<213> ORGANISM: Artificial Sequence
<220> FEATURE:
```

<223> OTHER INFORMATION: Amino acid sequence of the heavy chain of anti-human LAG-3/FITC mAb2 FS18-7-58/4420 comprising LALA mutation

<400> SEQUENCE: 71

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Tyr Pro Glu Ile Glu Phe Lys Thr Thr Pro Pro Val Leu Asp
385                 390                 395                 400
```

Ser Asp Gly Ser Phe Phe Leu Tyr Ser Lys Leu Thr Val Pro Tyr Asp
            405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 72
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-58/4420 without LALA mutation

<400> SEQUENCE: 72

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr

```
305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Trp Asp Glu Pro Trp Gly Glu Asp Val Ser Leu Thr Cys
                355                 360                 365

Leu Val Lys Gly Phe Tyr Pro Ser Asp Ile Ala Val Glu Trp Glu Ser
                370                 375                 380

Asn Gly Tyr Pro Glu Ile Glu Phe Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 73
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-62/4420 comprising LALA mutation

<400> SEQUENCE: 73

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
                35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

```
His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
370                 375                 380

Asn Gly Ile Pro Glu Trp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 74
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-62/4420 without LALA mutation

<400> SEQUENCE: 74

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

-continued

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
370                 375                 380

Asn Gly Ile Pro Glu Trp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 75
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-65/4420 comprising LALA mutation

<400> SEQUENCE: 75

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp

```
                50              55              60
Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Gly Met Asp Tyr Trp Gly Gln Gly Thr
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
            370                 375                 380

Asn Gly Tyr Ala Glu Tyr Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 76
<211> LENGTH: 447
<212> TYPE: PRT
<213> ORGANISM: Artificial Sequence
```

<220> FEATURE:
<223> OTHER INFORMATION: Amino acid sequence of the heavy chain of
      anti-human LAG-3/FITC mAb2 FS18-7-65/4420 without LALA mutation

<400> SEQUENCE: 76

```
Glu Val Lys Leu Asp Glu Thr Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
370                 375                 380

Asn Gly Tyr Ala Glu Tyr Asn Tyr Lys Thr Thr Pro Pro Val Leu Asp
```

```
                385                 390                 395                 400
Ser Asp Gly Ser Phe Phe Leu Tyr Ser Lys Leu Thr Val Pro Tyr Asp
                    405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 77
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-78/4420 comprising LALA mutation

<400> SEQUENCE: 77

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
    370                 375                 380

Asn Gly Tyr Lys Glu Glu Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
            405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 78
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-78/4420 without LALA mutation

<400> SEQUENCE: 78

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Tyr Lys Glu Glu Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 79
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-88/4420 comprising LALA mutation

<400> SEQUENCE: 79

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

```
                130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Trp Asp Glu Pro Trp Gly Glu Asp Val Ser Leu Thr Cys
                355                 360                 365

Leu Val Lys Gly Phe Tyr Pro Ser Asp Ile Ala Val Glu Trp Glu Ser
                370                 375                 380

Asn Gly Val Pro Glu Leu Asn Val Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 80
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-88/4420 without LALA mutation

<400> SEQUENCE: 80

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
                35                  40                  45
```

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Val Pro Glu Leu Asn Val Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 81
<211> LENGTH: 447
<212> TYPE: PRT

<213> ORGANISM: Artificial Sequence
<220> FEATURE:
<223> OTHER INFORMATION: Amino acid sequence of the heavy chain of
     anti-human LAG-3/FITC mAb2 FS18-7-95/4420 comprising LALA mutation

<400> SEQUENCE: 81

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

```
Asn Gly Tyr Gln Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
            405                 410                 415

Arg Trp Val Trp Pro Asp Glu Phe Ser Cys Ser Val Met His Glu Ala
        420                 425                 430

Leu His Asn His Tyr Thr Gln Lys Ser Leu Ser Leu Ser Pro Gly
    435                 440                 445
```

<210> SEQ ID NO 82
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-95/4420 without LALA mutation

<400> SEQUENCE: 82

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Tyr Gln Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 83
<211> LENGTH: 447
<212> TYPE: PRT
<213> ORGANISM: Artificial Sequence
<220> FEATURE:
<223> OTHER INFORMATION: Amino acid sequence of the heavy chain of
      anti-FITC mAb 4420 comprising LALA mutation

<400> SEQUENCE: 83

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

```
                       210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 84
<211> LENGTH: 447
<212> TYPE: PRT
<213> ORGANISM: Artificial Sequence
<220> FEATURE:
<223> OTHER INFORMATION: Amino acid sequence of the heavy chain of
      anti-FITC mAb 4420 without LALA mutation

<400> SEQUENCE: 84

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125
```

Leu Ala Pro Ser Ser Lys Ser Thr Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 85
<211> LENGTH: 219
<212> TYPE: PRT
<213> ORGANISM: Artificial Sequence
<220> FEATURE:
<223> OTHER INFORMATION: Amino acid sequence of the anti-FITC mAb 4420
      light chain

<400> SEQUENCE: 85

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 86
<211> LENGTH: 447
<212> TYPE: PRT
<213> ORGANISM: Artificial Sequence
<220> FEATURE:
<223> OTHER INFORMATION: Amino acid sequence of the heavy chain of
      anti-mouse LAG-3/PD-L1 mAb2 FS18-7-108-29/S1 with LALA mutation

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser

```
            180              185              190
Ser Leu Gly Thr Gln Thr Tyr Ile Cys Asn Val Asn His Lys Pro Ser
        195                  200                  205
Asn Thr Lys Val Asp Lys Lys Val Glu Pro Lys Ser Cys Asp Lys Thr
        210                  215                  220
His Thr Cys Pro Pro Cys Pro Ala Pro Glu Ala Ala Gly Gly Pro Ser
225                  230                  235                  240
Val Phe Leu Phe Pro Pro Lys Pro Lys Asp Thr Leu Met Ile Ser Arg
                245                  250                  255
Thr Pro Glu Val Thr Cys Val Val Val Asp Val Ser His Glu Asp Pro
            260                  265                  270
Glu Val Lys Phe Asn Trp Tyr Val Asp Gly Val Glu Val His Asn Ala
        275                  280                  285
Lys Thr Lys Pro Arg Glu Glu Gln Tyr Asn Ser Thr Tyr Arg Val Val
        290                  295                  300
Ser Val Leu Thr Val Leu His Gln Asp Trp Leu Asn Gly Lys Glu Tyr
305                  310                  315                  320
Lys Cys Lys Val Ser Asn Lys Ala Leu Pro Ala Pro Ile Glu Lys Thr
                325                  330                  335
Ile Ser Lys Ala Lys Gly Gln Pro Arg Glu Pro Gln Val Tyr Thr Leu
            340                  345                  350
Pro Pro Ser Trp Asp Glu Pro Trp Gly Glu Asp Val Ser Leu Thr Cys
        355                  360                  365
Leu Val Lys Gly Phe Tyr Pro Ser Asp Ile Val Val Glu Trp Glu Ser
        370                  375                  380
Asn Gly Gln Pro Glu Asn Asn Tyr Lys Thr Thr Pro Pro Val Leu Asp
385                  390                  395                  400
Ser Asp Gly Ser Phe Phe Leu Tyr Ser Lys Leu Thr Val Pro Phe Glu
                405                  410                  415
Arg Trp Met Trp Pro Asp Glu Phe Ser Cys Ser Val Met His Glu Ala
            420                  425                  430
Leu His Asn His Tyr Thr Gln Lys Ser Leu Ser Leu Ser Pro Gly
        435                  440                  445

<210> SEQ ID NO 87
<211> LENGTH: 447
<212> TYPE: PRT
<213> ORGANISM: Artificial Sequence
<220> FEATURE:
<223> OTHER INFORMATION: Amino acid sequence of the heavy chain of
      anti-mouse LAG-3/PD-L1 mAb2 FS18-7-108-29/S1 without LALA mutation

<400> SEQUENCE: 87

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
```

```
Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Val Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                405                 410                 415

Arg Trp Met Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 88
<211> LENGTH: 447
<212> TYPE: PRT
<213> ORGANISM: Artificial Sequence
<220> FEATURE:
<223> OTHER INFORMATION: Amino acid sequence of the heavy chain of
      anti-mouse LAG-3/PD-L1 mAb2 FS18-7-108-35/S1 with LALA mutation

<400> SEQUENCE: 88

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Ser
             20                  25                  30

Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
             100                 105                 110

Leu Val Thr Val Ser Ala Ala Ser Thr Lys Gly Pro Ser Val Phe Pro
         115                 120                 125

Leu Ala Pro Ser Ser Lys Ser Thr Ser Gly Gly Thr Ala Ala Leu Gly
 130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
         195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser His Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Trp Asp Glu Pro Trp Gly Glu Asp Val Ser Leu Thr Cys
         355                 360                 365

Leu Val Lys Gly Phe Tyr Pro Ser Asp Ile Ser Val Glu Trp Glu Ser
 370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                 405                 410                 415

Arg Trp Met Trp Pro Asp Glu Phe Ser Cys Ser Val Met His Glu Ala
             420                 425                 430
```

Leu His Asn His Tyr Thr Gln Lys Ser Leu Ser Leu Ser Pro Gly
            435                 440                 445

<210> SEQ ID NO 89
<211> LENGTH: 447
<212> TYPE: PRT
<213> ORGANISM: Artificial Sequence
<220> FEATURE:
<223> OTHER INFORMATION: Amino acid sequence of the heavy chain of
      anti-mouse LAG-3/PD-L1 mAb2 FS18-7-108-35/S1 without LALA mutation

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Trp Asp Glu Pro Trp Gly Glu Asp Val Ser Leu Thr Cys
            355                 360                 365

Leu Val Lys Gly Phe Tyr Pro Ser Asp Ile Ser Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                405                 410                 415

Arg Trp Met Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 90
<211> LENGTH: 447
<212> TYPE: PRT
<213> ORGANISM: Artificial Sequence
<220> FEATURE:
<223> OTHER INFORMATION: Amino acid sequence of the anti-mouse PD-L1 mAb
      S1 heavy chain with LALA mutation

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
```

```
                    260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
                435                 440                 445

<210> SEQ ID NO 91
<211> LENGTH: 447
<212> TYPE: PRT
<213> ORGANISM: Artificial Sequence
<220> FEATURE:
<223> OTHER INFORMATION: Amino acid sequence of the anti-mouse PD-L1 mAb
      S1 heavy chain without LALA mutation

<400> SEQUENCE: 91

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ala Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
```

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445

```
<210> SEQ ID NO 92
<211> LENGTH: 214
<212> TYPE: PRT
<213> ORGANISM: Artificial Sequence
<220> FEATURE:
<223> OTHER INFORMATION: Amino acid sequence of the anti-mouse PD-L1 mAb
      S1 light chain

<400> SEQUENCE: 92
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 93
<211> LENGTH: 449
<212> TYPE: PRT
<213> ORGANISM: Artificial Sequence
<220> FEATURE:
<223> OTHER INFORMATION: Amino acid sequence of the anti-human LAG-3 mAb
      25F7 heavy chain

<400> SEQUENCE: 93

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly

```
                225                 230                 235                 240
Pro Ser Val Phe Leu Phe Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                    325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                    405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly

<210> SEQ ID NO 94
<211> LENGTH: 214
<212> TYPE: PRT
<213> ORGANISM: Artificial Sequence
<220> FEATURE:
<223> OTHER INFORMATION: Amino acid sequence of the anti-human LAG-3 mAb
      25F7 light chain

<400> SEQUENCE: 94

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Ile Ser Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Leu
                85                  90                  95
Thr Phe Gly Gln Gly Thr Asn Leu Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
```

```
             130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 95
<211> LENGTH: 525
<212> TYPE: PRT
<213> ORGANISM: Artificial Sequence
<220> FEATURE:
<223> OTHER INFORMATION: Amino acid sequence of human LAG-3

<400> SEQUENCE: 95

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
                35                  40                  45

Pro Leu Gln Asp Leu Ser Leu Leu Arg Arg Ala Gly Val Thr Trp Gln
50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
                115                 120                 125

Arg Gly Asp Phe Ser Leu Trp Leu Arg Pro Ala Arg Arg Ala Asp Ala
                130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
                195                 200                 205

Gly Arg Val Pro Val Arg Glu Ser Pro His His Leu Ala Glu Ser
                210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
```

```
                275                 280                 285
Gly Thr Arg Ser Phe Leu Thr Ala Lys Trp Thr Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
        370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Phe Leu Ile Leu Gly Val Leu Ser Leu Leu Leu Leu
        450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
        515                 520                 525

<210> SEQ ID NO 96
<211> LENGTH: 521
<212> TYPE: PRT
<213> ORGANISM: Artificial Sequence
<220> FEATURE:
<223> OTHER INFORMATION: Amino acid sequence of mouse LAG-3

<400> SEQUENCE: 96

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65              70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
```

```
            115                 120                 125
Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Val Leu Val Leu Ile Leu
        435                 440                 445

Gly Ala Leu Ser Leu Phe Leu Leu Val Ala Gly Ala Phe Gly Phe His
    450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
        515                 520

<210> SEQ ID NO 97
```

```
<211> LENGTH: 533
<212> TYPE: PRT
<213> ORGANISM: Artificial Sequence
<220> FEATURE:
<223> OTHER INFORMATION: Amino acid sequence of cynomolgus LAG-3

<400> SEQUENCE: 97

Met Trp Glu Ala Gln Phe Leu Gly Leu Leu Phe Leu Gln Pro Leu Trp
1               5                   10                  15

Val Ala Pro Val Lys Pro Pro Gln Pro Gly Ala Glu Ile Ser Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Pro
65                  70                  75                  80

Val Pro Gly His Arg Pro Ala Ala Pro Tyr Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Thr Val His Leu Arg Asp Arg Ala Leu Ser Cys
145                 150                 155                 160

Arg Leu Arg Leu Arg Val Gly Gln Ala Ser Met Thr Ala Ser Pro Pro
                165                 170                 175

Gly Ser Leu Arg Thr Ser Asp Trp Val Ile Leu Asn Cys Ser Phe Ser
            180                 185                 190

Arg Pro Asp Arg Pro Ala Ser Val His Trp Phe Arg Ser Arg Gly Gln
        195                 200                 205

Gly Arg Val Pro Val Gln Gly Ser Pro His His Leu Ala Glu Ser
    210                 215                 220

Phe Leu Phe Leu Pro His Val Gly Pro Met Asp Ser Gly Leu Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Ala Thr Pro Leu Thr Val Tyr Ala
            260                 265                 270

Gly Ala Gly Ser Arg Val Glu Leu Pro Cys Arg Leu Pro Pro Ala Val
        275                 280                 285

Gly Thr Gln Ser Phe Leu Thr Ala Lys Trp Ala Pro Pro Gly Gly Gly
    290                 295                 300

Pro Asp Leu Leu Val Ala Gly Asp Asn Gly Asp Phe Thr Leu Arg Leu
305                 310                 315                 320

Glu Asp Val Ser Gln Ala Gln Ala Gly Thr Tyr Ile Cys His Ile Arg
                325                 330                 335

Leu Gln Gly Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Ala Ser Gly Gln Glu His Phe Val Trp Ser Pro
    370                 375                 380
```

Leu Asn Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu His Gln
            405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Arg Ala Gly
            435                 440                 445

His Leu Pro Leu Phe Leu Ile Leu Gly Val Leu Phe Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Leu Glu Pro Glu Pro
            500                 505                 510

Glu Leu Glu Arg Glu Leu Gly Pro Glu Pro Glu Pro Gly Pro Glu Pro
            515                 520                 525

Glu Pro Glu Gln Leu
            530

<210> SEQ ID NO 98
<211> LENGTH: 107
<212> TYPE: PRT
<213> ORGANISM: Artificial Sequence
<220> FEATURE:
<223> OTHER INFORMATION: Amino acid sequence of Fcab FS18-7-9 CH3 Domain
      comprising C-terminal lysine

<400> SEQUENCE: 98

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
            85                  90                  95

Thr Gln Lys Ser Leu Ser Leu Ser Pro Gly Lys
            100                 105

<210> SEQ ID NO 99
<211> LENGTH: 318
<212> TYPE: DNA
<213> ORGANISM: Artificial Sequence
<220> FEATURE:
<223> OTHER INFORMATION: CHO codon optimised nucleotide sequence of Fcab
      FS18-7-9 CH3 domain

<400> SEQUENCE: 99
ggccagcccc gggaacccca ggtgtacaca ctgcctccat cctgggatga gccctggggc      60
gaggatgtgt ctctgacctg tctcgtgaaa ggcttctacc cctccgatat cgccgtggaa     120
tgggagagca acggccagcc cgagaacaac tacaagacca cccccccctgt gctggactcc    180

```
gacggctcat tcttcctgta cagcaagctg acagtgccct acgacagatg ggtgtggccc      240
gacgagttct cctgctccgt gatgcacgag gccctgcaca accactacac ccagaagtcc      300
ctgtccctga gccccggc                                                    318
```